United States Patent
Wheeler

(10) Patent No.: US 11,567,078 B2
(45) Date of Patent: Jan. 31, 2023

(54) BLOOD CELL BIOMARKER FOR LATE ONSET ALZHEIMER'S DISEASE

(71) Applicant: Cedars-Sinai Medical Center, Los Angeles, CA (US)

(72) Inventor: Christopher Wheeler, Newbury Park, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 412 days.

(21) Appl. No.: 15/754,997

(22) PCT Filed: Aug. 31, 2016

(86) PCT No.: PCT/US2016/049598
§ 371 (c)(1),
(2) Date: Feb. 23, 2018

(87) PCT Pub. No.: WO2017/040594
PCT Pub. Date: Mar. 9, 2017

(65) Prior Publication Data
US 2020/0333339 A1    Oct. 22, 2020

Related U.S. Application Data

(60) Provisional application No. 62/212,070, filed on Aug. 31, 2015.

(51) Int. Cl.
| | | |
|---|---|---|
| G01N 33/567 | (2006.01) | |
| G01N 33/569 | (2006.01) | |
| A61K 47/64 | (2017.01) | |
| A61P 25/28 | (2006.01) | |
| A61K 31/06 | (2006.01) | |
| A61K 31/585 | (2006.01) | |
| A61K 33/00 | (2006.01) | |
| A61K 33/04 | (2006.01) | |
| A61K 33/18 | (2006.01) | |
| A61K 33/42 | (2006.01) | |
| A61K 39/395 | (2006.01) | |
| C07K 14/47 | (2006.01) | |
| C07K 14/74 | (2006.01) | |
| G01N 33/50 | (2006.01) | |
| A61K 38/00 | (2006.01) | |

(52) U.S. Cl.
CPC ....... *G01N 33/56972* (2013.01); *A61K 31/06* (2013.01); *A61K 31/585* (2013.01); *A61K 33/00* (2013.01); *A61K 33/04* (2013.01); *A61K 33/18* (2013.01); *A61K 33/42* (2013.01); *A61K 39/3955* (2013.01); *A61K 47/641* (2017.08); *A61P 25/28* (2018.01); *C07K 14/4711* (2013.01); *C07K 14/70539* (2013.01); *G01N 33/5091* (2013.01); *A61K 38/00* (2013.01); *G01N 2333/4709* (2013.01); *G01N 2800/2821* (2013.01); *G01N 2800/50* (2013.01)

(58) Field of Classification Search
CPC ....... C07K 14/4711; G01N 2800/2821; G01N 2800/50; G01N 33/6896; A61K 38/1716
See application file for complete search history.

(56) References Cited

U.S. PATENT DOCUMENTS

2018/0180601 A1*  6/2018  Pedersen .......... G01N 33/56977

FOREIGN PATENT DOCUMENTS

| EP | 3345000 | 7/2018 |
|---|---|---|
| WO | 96/26962 A1 | 9/1996 |
| WO | 2004013172 A2 | 2/2004 |
| WO | 2015157117 A2 | 10/2015 |
| WO | 2017040594 A1 | 3/2017 |
| WO | 2017196432 A1 | 11/2017 |

OTHER PUBLICATIONS

Speciale et al, Neurobio Aging, 28:1163-1169, 2007.*
International Search Report and Written Opinion of PCT/US2016/049598, dated Feb. 7, 2017, 10 Pages.
Jonsson et al., A Mutation in APP Protects Against Alzheimer's Disease and Age-Related Cognitive Decline, 2012, Nature, vol. 488(7409), pp. 96-99.
Lambracht-Washington et al., Active DNA Aβ2 Vaccination as Immunotherapy for Alzheimer Disease, 2012, Translational Neuroscience, vol. 3(4), pp. 307-313.
Lueg et al., Clinical Relevance of Specific T-cell Activation in the Blood and Cerebrospinal Fluid of Patients with Mild Alzheimer's Disease, 2015, Neurobiology of Aging, 2015, vol. 36(1), pp. 81-89.
Peters et al., APLP2 Regulates the Expression of MHC Class I Molecules on Irradiated Ewing's Sarcoma Cells, 2013, OncoImmunology, vol. 2(10), pp. e26293-1 to e26293-9.
Schindowski et al., Increased T-cell Reactivity and Elevated Levels of CD8+ Memory T-cells in Alzheimer's Disease-patients and T-cell Hyporeactivity in an Alzheimer's Disease-mouse Model: Implications for Immunotherapy, 2007, Neuromolecular Med., vol. 9(4), pp. 340-354.
Velthuis et al., Simultaneous Detection of Circulating Autoreactive CD8 T-cells Specific for Different Islet Cell-Associated Epitopes Using Combination MHC Multimers, 2010, Diabetes, vol. 59(7), pp. 1721-1730.
Partial Supplementary European Search Report of EP 16842865.4, dated Feb. 12, 2019, 16 Pages.
Bakker et al., MHC Mutimer Technology: Current Status and Future Prospects, 2005, Current Opinion in Immunology, vol. 17(4), pp. 428-433.

(Continued)

*Primary Examiner* — Mark Halvorson
(74) *Attorney, Agent, or Firm* — Entralta P.C.; James F. Fleming; Peter D. Weinstein

(57) ABSTRACT

Described herein are compositions and methods for diagnosing late-onset Alzheimer's disease (LOAD), treating LOAD and assessing efficacy of therapeutic agents used to treat LOAD.

19 Claims, 28 Drawing Sheets
Specification includes a Sequence Listing.

(56) References Cited

OTHER PUBLICATIONS

EBI Database, Class II Amyloid Beta Epitope SEQ ID No. 5072, XP002788263, Jan. 11, 2018, Retrieved from EBI Accession No. GSP: BEQ63957, Database Accession No. BEQ63957, 1 Page.
EBI Database, N-Terminal Truncated Beta-Amyloid Peptide, SEQ ID No. 142, XP002788262, May 6, 2004, Retrieved from EBI Accession No. GSP: ADJ71479, Database Accession No. ADJ71479, 1 Page.
Lanuti et al., Amyloid-Specific T-Cells Differentiate Alzheimer's Disease from Lewy Body Dementia, 2012, Neurobiology of Aging, vol. 33, pp. 2599-2611.
Monsonego et al., Increased T Cell Reactivity to Amyloid β Protein in Older Humans and Patients with Alzheimer Disease, 2003, Journal of Clinical Investigation, vol. 112(3), pp. 415-422.

\* cited by examiner

D-J diversity & joints

Spleen TCR Vβ PCR          Brain TCR Vβ PCR

Brain WB

4G8 Burden

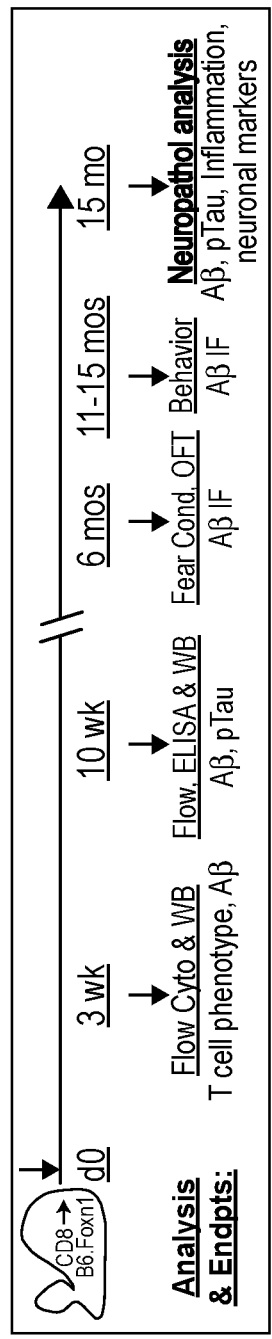
FIG. 6A
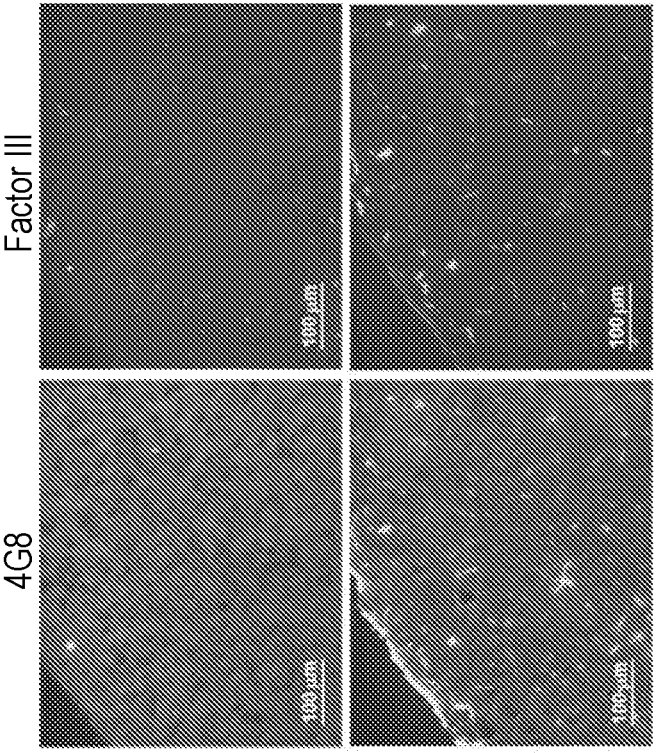
FIG. 6B
FIG. 6C
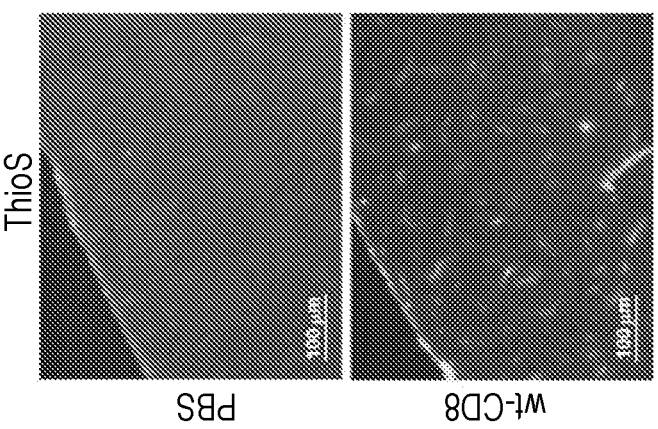

FIG. 11A
FIG. 11B
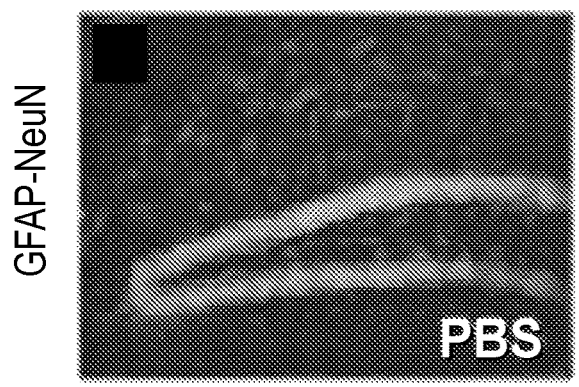
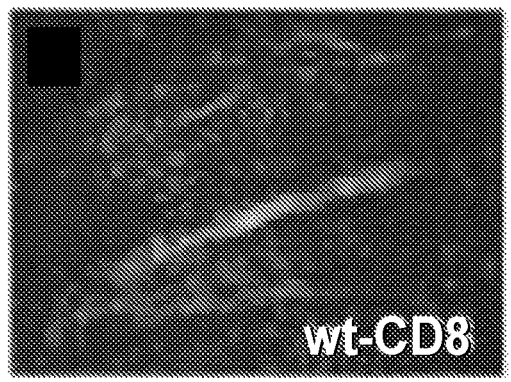
FIG. 11C
FIG. 11D
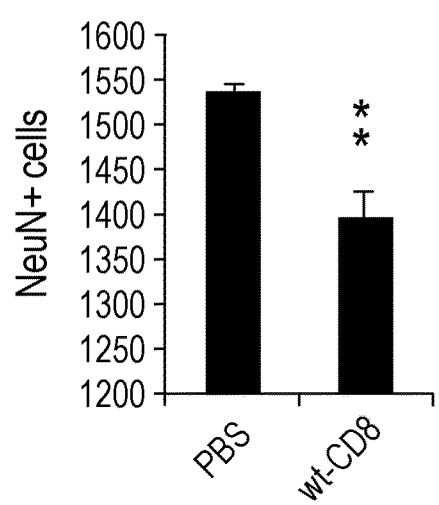
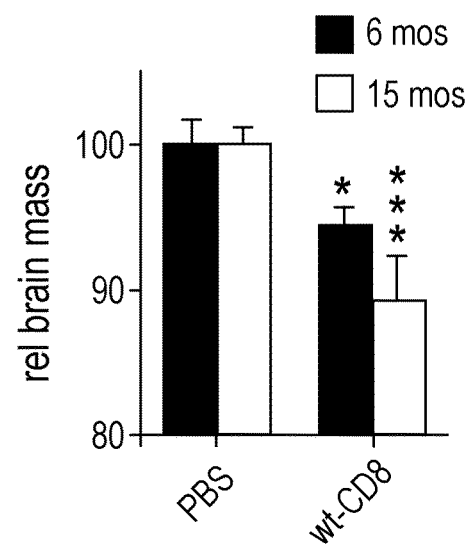
FIG. 11E
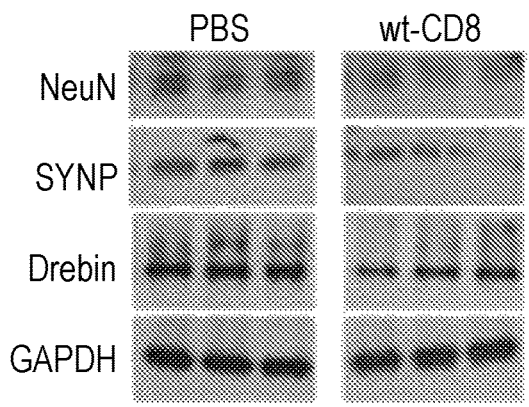

Spontaneous Alt test

Barnes Maze test
Training/Acquisition Phase

Memory Retention
Day 7

Reversal Phase

Reversal Phase
Day 9

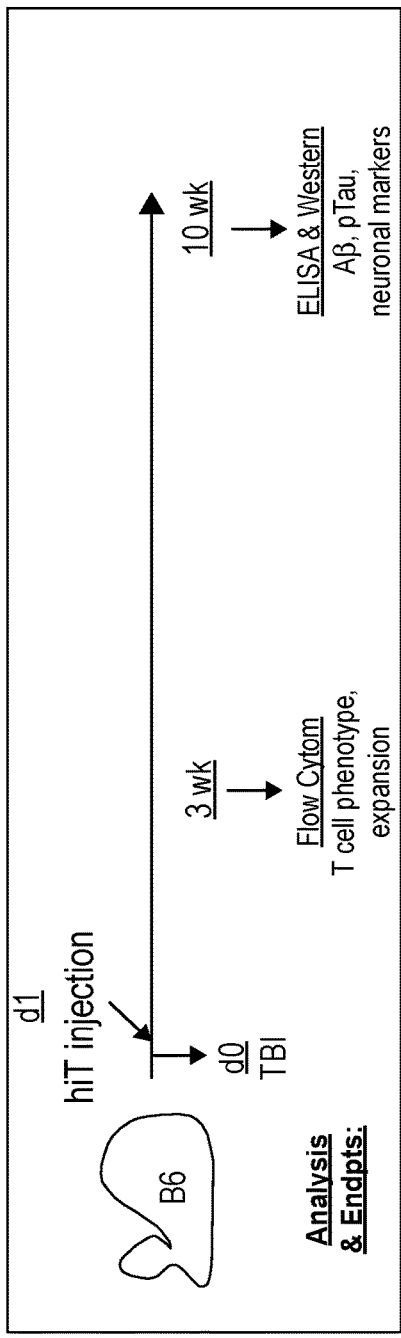
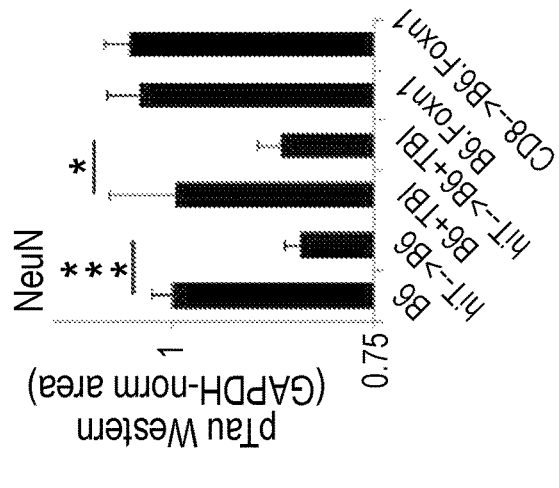
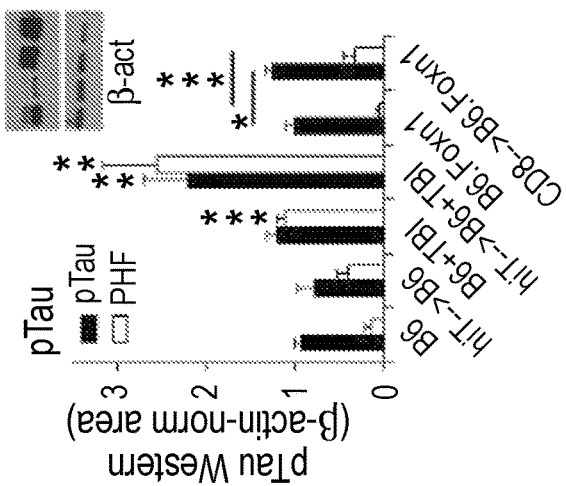
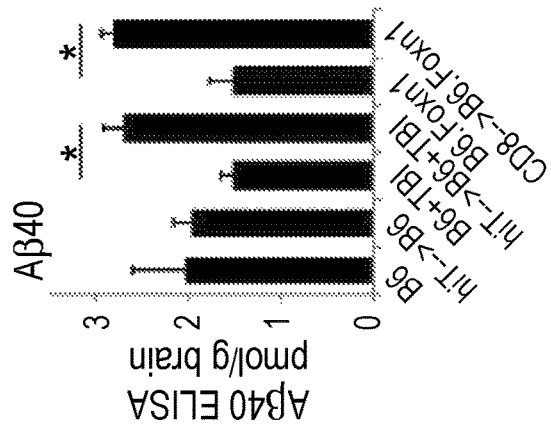

SEQUENCE LISTING

```
<160> NUMBER OF SEQ ID NOS: 6

<210> SEQ ID NO 1
<211> LENGTH: 770
<212> TYPE: PRT
<213> ORGANISM: Homo sapiens

<400> SEQUENCE: 1

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
                100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
        130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Glu Asp Gly Asp Glu Val Glu Glu
            245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
            275                 280                 285

Glu Val Cys Ser Glu Gln Ala Glu Thr Gly Pro Cys Arg Ala Met Ile
            290                 295                 300
```

```
Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
                340                 345                 350

Thr Gln Glu Pro Leu Ala Arg Asp Pro Val Lys Leu Pro Thr Thr Ala
            355                 360                 365

Ala Ser Thr Pro Asp Ala Val Asp Lys Tyr Leu Glu Thr Pro Gly Asp
        370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
        690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
```

```
                    725                 730                 735
Glu Val Asp Ala Ala Val Thr Pro Glu Arg His Leu Ser Lys Met
            740                 745                 750
Gln Gln Asn Gly Tyr Glu Asn Pro Thr Tyr Lys Phe Phe Glu Gln Met
        755                 760                 765
Gln Asn
    770

<210> SEQ ID NO 2
<211> LENGTH: 9
<212> TYPE: PRT
<213> ORGANISM: Artificial Sequence
<220> FEATURE:
<223> OTHER INFORMATION: synthetic

<400> SEQUENCE: 2

Ala Leu Glu Asn Tyr Ile Thr Ala Leu
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic

<400> SEQUENCE: 3

Lys Leu Val Phe Phe Ala Glu Asp Val
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic

<400> SEQUENCE: 4

Leu Met Val Gly Gly Val Val Ile Ala
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic

<400> SEQUENCE: 5

Gly Leu Met Val Gly Gly Val Val Ile
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic

<400> SEQUENCE: 6

Val Ile Val Ile Thr Leu Val Met Leu
1               5
```

BLOOD CELL BIOMARKER FOR LATE ONSET ALZHEIMER'S DISEASE

CROSS-REFERENCE TO RELATED APPLICATIONS

This application is a National Phase of International Application No. PCT/US2016/049598 filed Aug. 31, 2016, currently pending, which designated the U.S. and that International Application was published under PCT Article 21(2) in English, which also includes a claim of priority under 35 U.S.C. § 119(e) to U.S. provisional patent application No. 62/212,070 filed Aug. 31, 2015, entirety of which is hereby incorporated by reference.

GOVERNMENT RIGHTS

This invention was made with government support under Grant Nos. NS054162 and AG033394 awarded by the National Institutes of Health. The government has certain rights in the invention.

TECHNICAL FIELD

The invention relates to diagnostic assays to identify subjects with late onset Alzheimer's disease and therapeutic methods for treating subjects with late onset Alzheimer's disease.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Alzheimer's disease (AD) is characterized by progressive neurodegeneration with deposition of amyloid beta (Aβ) plaques and neurofibrillary tangles in brain. Our ability to prevent or treat diseases such as AD is dependent on knowing their cause(s). Familial AD (FAD) gene mutations guarantee early-onset disease in perhaps up to 1% of patients, but AD etiology is otherwise thought to be heterogeneous and multi-factorial, with age as the strongest risk factor for late-onset disease. Mouse models harboring FAD mutations alone have had significant utility, including clarifying an important role of the immune system in the pathophysiology of AD and as a paradigm for treatment development. They have, however, fallen short in predicting successful translation of treatments to the clinic, perhaps because they do not successfully mimic some of the features of AD. As such, they may not reflect the initial causal factors of late-onset or sporadic AD (LOAD), the predominant form of AD, for which the initiating events are still unclear.

Although moderate to advanced aging is the only known factor necessary for all forms of human AD, key features are absent in FAD-based mouse models at all ages. These missing features include neuronal loss and neurofibrillary deposition (1), and suggest that current mouse models are intrinsically deficient in at least one age-related factor required for their generation. Several age-related factors have been tested and found to contribute to AD-like pathology in mice, including inflammation, vascular dysfunction, and insulin resistance (2-5). Nevertheless, none of these reconstitutes all features of human AD in mice, either alone or together with FAD-based gene mutations. The contribution of age-related physiological processes that are themselves deficient in mice, however, has not been examined.

CD8 T cell homeostatic expansion is a process that commonly results in the accumulation of functionally aberrant self-reactive T cell clones in aging humans, but not in mice (6-8). This process expands memory-phenotype CD8 T cells exclusively, which have recently been shown to increase in AD patients but not in FAD-based mouse models as well (9-12). Moreover, we have demonstrated that CD8 T cells critically impact age-dependent brain tumor outcomes (13, 14), and others have shown their critical contribution to tissue inflammation (15-17). Thus, CD8 T cell function may be generally relevant to brain and/or inflammatory disorders, and their homeostatic expansion in aging could be specifically involved in AD pathology.

CD8 T cells can be induced to undergo homeostatic expansion by introduction into young T cell-deficient hosts. It remains unclear how well this induced homeostatic expansion in otherwise T cell-deficient hosts corresponds to their age-related clonal expansion, let alone whether it impacts neurodegeneration and AD neuropathology specifically. Herein, we show that CD8 T cell homeostatic expansion in T cell-deficient (B6.Foxn1) hosts results in similar surface phenotype, antigen reactivity, clonality, and presence in brain as CD8 T cells in extensively aged wild-type mice. We denoted these homeostatically-induced CD8 cells "hiT" cells, and evaluated AD-like pathophysiology in hiT-bearing B6.Foxn1 mice, as well as their ability to synergistically promote AD-like neuropathology in wild-type mice together with brain injury. Levels of hiT cell-associated metrics were also quantified in human AD patients.

We found that nude mice harboring hiT cells developed cognitive impairment and brain atrophy ahead of overt deposition of Aβ plaques and silver-staining neurofibrillary structures. Distinct aspects of this pathology were dependent on T cell IFNγ and Perforin production. Transfer of hiT cells into wild-type mice also resulted in rapid neuronal marker loss and moderate pTau elevation, but decreased Aβ. Nevertheless, hiT cells synergized with brain injury in these mice to greatly increase Aβ, pTau, and fibrillary tau accumulation. Finally, gene expression, effector protein, and immune receptor specificity associated with hiT cells were specifically up-regulated in human AD brain.

SUMMARY

The following embodiments and aspects thereof are described and illustrated in conjunction with systems, compositions and methods which are meant to be exemplary and illustrative, not limiting in scope.

Provided herein is an assay for determining the likelihood of late onset Alzheimer's disease (LOAD) in a subject in need thereof. The assay includes obtaining a sample from the subject; assaying the sample to determine the level of amyloid precursor protein (APP)-specific CD8+ T cells; and determining that the subject has an increased likelihood of LOAD if the level of the APP-specific CD8+ T cells are higher relative to the reference sample, or determining that the subject has a decreased likelihood of LOAD if the level of the APP-specific CD8+ T cells are same as or lower relative to the reference sample.

In various embodiments, the APP peptide for use with the assays and method described herein comprises, consist of or consist essentially of the amino acid sequence ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6). In further embodiments, APP peptide suitable for use with aspects of the invention described herein may be derived from the human APP having the full length sequence set forth in SEQ ID NO: 1.

In various embodiments, assaying the sample includes quantitating the number of APP-specific CD8+ T cells in the sample.

In some embodiments, the APP-specific CD8+ T cells in the sample are quantitated using MHC multimers specific to peptides of APP. Examples of MHC multimers include but are not limited to MHC dimers, MHC tetramers, MHC pentamers or MHC dextramers.

In some embodiments, the APP peptide-specific MHC multimers are labeled with a detection agent. Examples of detection agent include but are not limited to fluorescent tags, biotin tags, FITC, PE, R-PE, PE-Cy5; PE-Cy7, APC or PacBlue. In exemplary embodiments, APP-specific CD8+ T cells complexed with the labeled detection agent are quantitated using assays including but not limited to flow cytometry, MACS and ELISPOT assay.

In various embodiments, the subject exhibits risk factors associated with LOAD. In some embodiments, the risk factors associated with LOAD are any one or more of mild cognitive impairment (MCI), traumatic brain injury, diabetes mellitus, APOEε4 allele expression or a combination thereof. In some embodiments, the subject does not exhibit risk factors associated with LOAD and is at least 50 years old, at least 60 years old, at least 65 years old or at least 70 years old.

In some embodiments, the sample is tissue, blood, plasma or a combination thereof.

In some embodiments, the subject is human.

In various embodiments, the reference value is the mean or median level of APP-specific CD8+ T cells in a population of subject that do not have LOAD.

In various embodiments, the reference value is the mean or median level of APP-specific CD8+ T cells in the sample obtained from the subject at a different time point.

In some embodiments, provided herein is a method for treating LOAD in a subject in need thereof. The method includes determining the likelihood that the subject has LOAD using the methods described herein and administering a therapeutic agent to the subject with increased likelihood of having LOAD.

In some embodiments, the therapeutic agent for use in the methods described herein comprises an APP peptide-specific MEW multimer conjugated to a cytotoxic agent. In some embodiments, the cytotoxic agent is a toxin, antibody, heavy metal, radioisotope, or hapten.

In some embodiments, examples of toxins include but are not limited to cyclophosphamide, methrotrexate, Azathioprine, mizoribine, 15-deoxuspergualin, neomycin, staurosporine, genestein, herbimycin A, *Pseudomonas* exotoxin A, saporin, Rituxan, Ricin, gemtuzumab ozogamicin, or Shiga toxin.

In some embodiments, examples of heavy metal are any one or more if inorganic mercurial, organic mercurial, FN18-CRM9 or combinations thereof.

In some embodiments, radioisotopes are incorporated isotopes of iodide, cobalt, selenium, tritium, and phosphorus.

In some embodiments, haptens are DNP or digoxiginin.

Also provided herein are compositions comprising MHC/APP peptide complex. In some embodiments, the MHC is a class 1 MHC. In some embodiments, the MHC is a MHC-1 dextramer. In some embodiments, APP peptide comprises of the amino acid sequence ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6).

Further provided herein are methods comprising obtaining the results of a diagnostic test which determines whether a subject is likely to have LOAD and treating the subject for LOAD using therapeutic methods, for example, those described herein, if it is determined that the subject likely has LOAD. In some embodiments, determining whether a subject is likely to have LOAD includes obtaining a sample from the subject; assaying the sample to determine the level of amyloid precursor protein (APP)-specific CD8+ T cells; and determining that the subject has an increased likelihood of LOAD if the level of the APP-specific CD8+ T cells are higher relative to the reference sample, or determining that the subject has a decreased likelihood of LOAD if the level of the APP-specific CD8+ T cells are same as or lower relative to the reference sample.

Also provided herein are treatment methods comprising administering a therapeutic agents (for example, those described herein) to a subject diagnosed with having LOAD. In some embodiments, diagnosis of LOAD includes obtaining a sample from the subject; assaying the sample to determine the level of amyloid precursor protein (APP)-specific CD8+ T cells; and determining that the subject has an increased likelihood of LOAD if the level of the APP-specific CD8+ T cells are higher relative to the reference sample, or determining that the subject has a decreased likelihood of LOAD if the level of the APP-specific CD8+ T cells are same as or lower relative to the reference sample.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 6 depicts in accordance with various embodiments of the invention, analysis scheme, and vascular Aβ in brain after CD8 T cell injection. Analysis time line in CD8 T cell-injected B6.Foxn1 recipients (A). Immunohistochemical staining for ThioS in B6.Foxn1 cortex 6 months post-injection, exhibiting vascular staining pattern in mice injected with wt-CD8 T cells but not with PBS (B). Aβ (4G8) and Factor III staining in B6.Foxn1 cortex 6 months after injection with wt-CD8 T cells confirms retention of increased vascular Aβ in nude mice harboring hiT cells (C). All images at 5× magnification.

FIG. 12 depicts in accordance with various embodiments of the invention, motor activity, cognitive performance and correlation with pathological features. Open Field total activity and rearing activity at 3, 6, and 13 months post-injection of CD8 T cells in experimental mouse groups (A). There was no substantial alteration in total or rearing activity between PBS and wt-CD8 groups at any time point, although total activity significantly increased after 3 months, and rearing activity significantly decreased by 13 months, in both groups (n≥9 mice/group). Individual mouse performance in Fear Conditioning test at 6 months correlated directly with brain mass (n=27; mice were from PBS and wt-CD8 groups; B). Superior performance of individual mice in Barnes Maze at 14 months was significantly associated with higher brain mass (n=9; mice were from all groups; *P>0.05, +P>0.1 by 2-tailed T-test; C). Poor performance on Barnes Maze exhibited a non-significant association with increased soluble pTau, and a significant association with increased tau PHFs on Westerns (D). Poor maze performance was not significantly associated with either Triton-soluble or Gaunidium-soluble Aβ40 and Aβ42 by ELISA, although a non-significant and slight association emerged for increased Gaunidium-soluble Aβ40 (E, F).

Figure 13E:
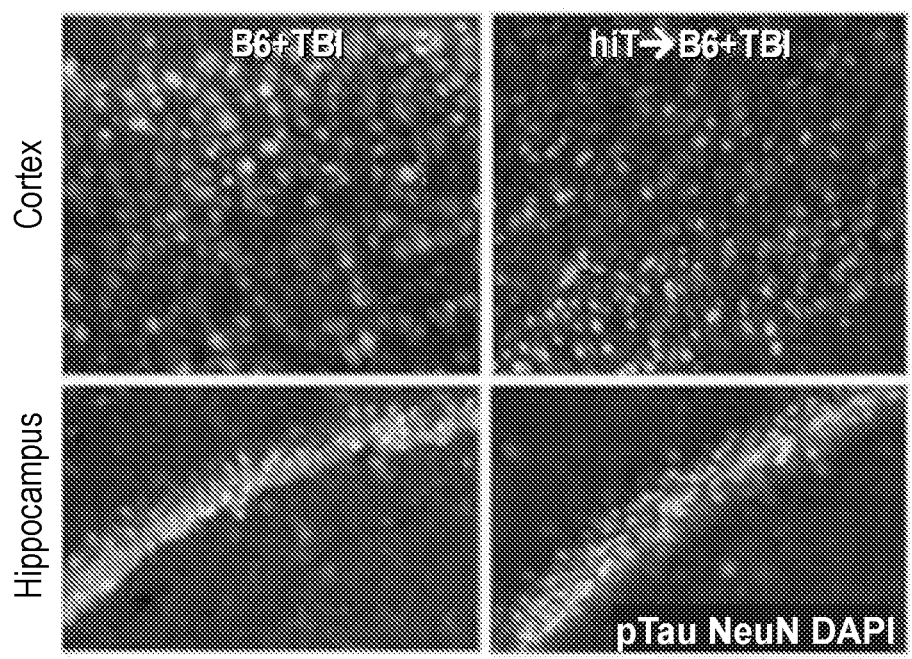
Figure 13F:
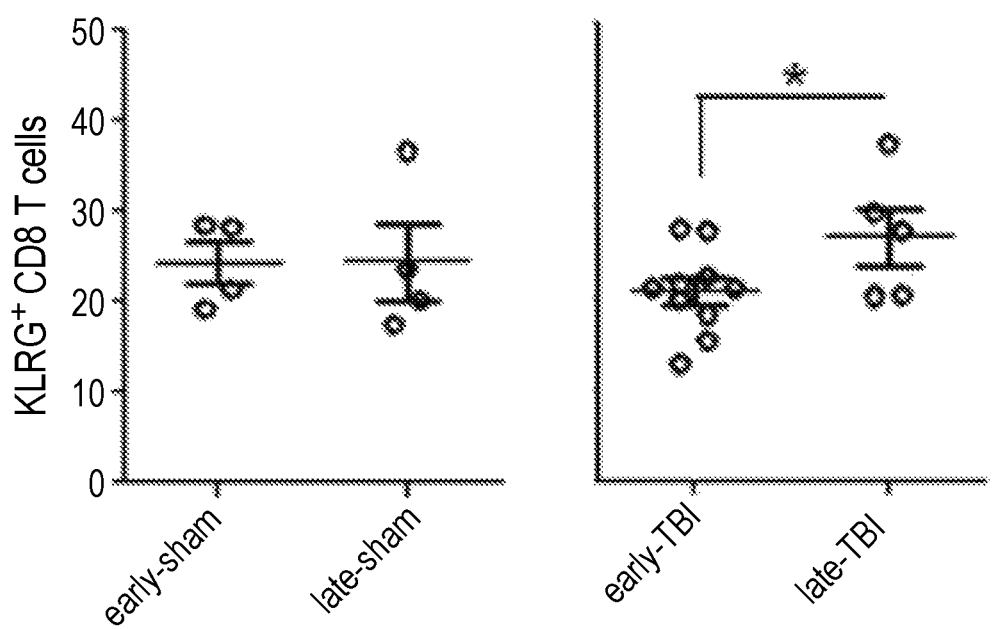

FIG. 13 depicts in accordance with various embodiments of the invention, synergy between hiT cells and traumatic brain injury (TBI) in wild-type mice. CD8 T cells were purified from B6.Foxn1 mice injected 5 weeks earlier, and CF SE-labeled. 3×10$^6$ of these hiT cells were injected into 10-week old wild-type (C57BL/6J=B6) females that had received traumatic brain injury (TBI) or sham the day before. dMice were bled the day of and 3 weeks after T cell injection, and sacrificed at 10 weeks later (A). Forebrain ELISA of detergent-soluble mouse Aβ1-40 (B), pTau/PHF (C), and NeuN Western signals (D), in B6 recipients (n=6/group: "+" above pTau bands in Western=hiT cell recipients). pTau and NeuN immunofluorescent staining of TBI and/or injected mice (E). Flow cytometric analysis of CFSE$^+$ T cells co-staining for KLRG1 and CD8 the day of (early) and 3 weeks (late) after injection (F). *P<0.05, ***P<0.005, in two-sided T-test FIG. 14 depicts in accordance with various embodiments of the invention, increased hiT cell-associated metrics in human AD brain. GFAP expression in microarray database (n≥9; GEO accession # s GSM21203-GSM21233)(A). Percent up- or down-regulation relative to GFAP in AD patients for indicated markers (P<0.05 by ANOVA and/or 1-sided T-test)(B). Additional probesets/genes evaluated relative to GFAP in severe AD: β$_2$m (−45%, P=0.031), GAPDH (−60%, P=0.093), β-actin (−61%, P=0.039), β-tubulin (−39%, P=0.017), PRF1 (89%, P=0.131), IFNγ (109%, P=0.034), and CD107a (113%, P=0.032). PRF1 Western and immunofluorescence (C), with quantifications in age-matched normal, mild, or severe AD brain. (D). AD brain co-stained with anti-CD8 (Serotec) and APP$_{(471-479)}$/HLA-A2 multimer (Immudex USA, Fairfax, Va.)(E), with quantification of epitope-reactive T cells (P=0.002, 2-sided T-test)(F). Overall levels of CD8 T cells were unchanged (1.63±0.29 vs. 2.29±0.55 cells/vessel in AD vs. normal aging controls; P=0.31, 2-sided T-test).

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies *A Laboratory Manual* 2$^{nd}$ ed., Cold Spring Harbor Press (Cold Spring Harbor N.Y., 2013); Köhller and Milstein, *Derivation of specific antibody-producing tissue culture and tumor lines by cell fusion*, Eur. J. Immunol. 1976 July, 6(7):511-9; Queen and Selick, Humanized immunoglobulins, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

Late onset Alzheimer's disease (LOAD) is the most common neurodegenerative disorder of aging, affecting 5.4 millon domestic patients annually. Little is known about how specific aging properties impact LOAD pathoetiology, in part because in vivo models for them in isolation do not exist. We report here that homeostatic expansion of CD8 T cells, as occurs with aging, leads to aberrant self-reactive memory phenotype cells locating to mouse brain, which promote sustained Aβ overproduction. Mice harboring these cells, but not homeostatically expanded Interferony-deficient or Perforin1-deficient CD8 T cells, develop cerebrovascular Aβ prior to the accumulation of plaques and neurofibrillary structures, as well as neuroinflammation, neuronal loss, progressive brain atrophy and severe cognitive impairment, all hallmarks of sporadic AD. Most importantly, gene expression, effector protein, and T cell epitopes identified in these mice were consistently elevated in human AD brain. The results support the possibility that aberrant T cells are critical initiators of sporadic AD in some patients and therefore represent novel targets for treatment. Inventors note that in late onset AD model, APP-specific CD8+ T cells first expand in blood and exhibit age-related appearance and function, selectively enter brain and promote full molecular neurodegenerative, and behavioral pathology of AD. Accordingly, APP-specific and related antigen-specific CD8 T cells may serve as novel biomarkers for human AD.

When presented by an MHC on antigen presenting cells, APP peptides can be used to identify CD8+ T cells specific to the peptides of APP. These MHC/peptide complexes can use useful for detecting CD8+ T cells that recognize the particular APP peptides and thus predict AD.

"Amino acid" as used herein is meant to include both natural and synthetic amino acids, and both D and L amino acids. "Standard amino acid" means any of the twenty L-amino acids commonly found in naturally occurring peptides. "Nonstandard amino acid" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides disclosed herein, and particularly at the carboxy- or amino-terminus, can be modified by methylation, amidation, acetylation or substitution with other chemical groups which can change the peptide's circulating half-life without adversely affecting their biological activity. Additionally, a disulfide linkage may be present or absent in the peptides disclosed herein.

"APP" as used herein refers to Amyloid Precursor Protein.

"APP peptide" as used herein refers to a peptide comprising a portion of APP amino acid sequence. The peptides may be 7 to 10 amino acids longs. In an exemplary embodiment, an APP peptide comprises the sequence ALENYITAL (SEQ ID NO: 2), KLVFFAEDV (SEQ ID NO: 3), LMVGGVVIA (SEQ ID NO: 4), GLMVGGVVI (SEQ ID NO: 5) or VIVITLVML (SEQ ID NO: 6). In further embodiments, any other APP peptides of suitable length that are predicted and validated to stably bind HLA (human MHC) molecules can be used with the methods described herein. In some embodiments, SEQ ID NOs: 2-6 represent APP-derived peptides that may stably bind the most common HLA allele in the western world (HLA-A2) that may be readily manufactured; additional peptide/HLA combinations may be utilized depending on patient cohort demographics as would be apparent to a person of skill in the art.

"Autoimmunity" as used herein is defined as persistent and progressive immune reactions to non-infectious self-antigens, as distinct from infectious non-self-antigens from bacterial, viral, fungal, or parasitic organisms which invade and persist within mammals and humans. An autoimmune response occurs when the immune system of an individual recognizes self-antigens as foreign, leading to the production of self-reactive effector immune cells. Self-reactive effector immune cells include cells from a variety of lineages, including, but not limited to, cytotoxic T cells, helper T cells, and B cells. While the precise mechanisms differ, the presence of autoreactive effector immune cells in an individual suffering from an autoimmune disease leads to the destruction of tissues and cells of the individual, resulting in pathologic symptoms. An individual with an autoimmune disease may be diagnosed as known to one of ordinary skill in the art. Such individuals may be identified symptomatically and/or by obtaining a sample from the individual and isolating autoreactive T cells and comparing the level of autoreactive T cells in the individual to a control. See, e.g., US Patent Application Publication 2006/0105336, which is incorporated by reference in its entirety. Numerous assays for determining the presence of such cells in an individual, and therefore the presence of an autoimmune disease, such as an antigen specific autoimmune disease in an individual, are known to those of skill in the art and readily employed in the disclosed methods. Assays of interest include, but are not limited to, those described in, e.g., Autoimmunity 36(6-7): 361-366 (2003); J. Pediatr. Hematol. Oncol. 25(Suppl 1): S57-S61 (2003); Proteomics 3(11): 2077-2084 (2003); Autoimmun. Rev. 2(1): 43-49 (2003).

Herein, "peptide" and "protein" are used interchangeably, and refer to a compound comprised of at least two amino acid residues covalently linked by peptide bonds or modified peptide bonds (e.g., peptide isosteres). No limitation is placed on the maximum number of amino acids which may comprise a protein or peptide. The amino acids comprising the peptides or proteins described herein and in the appended claims are understood to be either D or L amino acids with L amino acids being preferred. The amino acid comprising the peptides or proteins described herein may also be modified either by natural processes, such as post-translational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide. Also, a given peptide may contain many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W.H. Freeman and Company, New York, 1993 and Wold F, Posttranslational Protein Modifications: Perspectives and Prospects, pgs. 1-12 in Posttranslational Covalent Modification of Proteins, B. C. Johnson, Ed., Academic Press, New York, 1983; Seifter et al., "Analysis for protein modifications and nonprotein cofactors," Meth. Enzymol. (1990) 182: 626-646 and Rattan et al. (1992), "Protein Synthesis: Posttranslational Modifications and Aging," Ann NY Acad Sci 663: 48-62.

"Frequency" as used herein refers to the frequency of occurrence of particular antigen-specific $CD8^+$ T cells in mice or other laboratory species or humans.

"Immune-based disorder" as used herein refers to a condition, disorder, or disease in which an aberrant immune response contributes to the pathogenesis of the immune-based disorder in the individual. An aberrant immune response is any immune reaction in an individual characterized as an unwanted immune or autoimmune response. An immune-based disorder includes, without limitation, an autoimmune condition, disorder or disease, a graft vs. host disease, a cancer, immune-based inflammatory diseases, and persistent and progressive immune reactions to infectious non self-antigens from bacterial, viral, fungal, or parasitic organisms which invade and persist within mammals and humans. The source of the provoking foreign antigen can be plant, fungal, mold, or other environmental contaminant. For example, an immune-based disorder can be an autoimmune response and the antigen is an autoantigen, a graft vs. host immune response and the antigen is an autoantigen, an allergy, an asthma, or a graft vs. host immune response and the antigen is a purified or unpurified component of the allergen or transplanted tissue or organ provoking the harmful immune response.

"Individual-compatible T-cells" as used herein refers to cells that can be introduced into the subject, optionally in conjunction with an immunosuppressive therapy, without resulting in extensive chronic graft versus host disease (GvHD).

"Major histocompatibility complex (MHC)" as used herein refers to a cell surface molecule encoded by a large gene family in all vertebrates. MEW molecules mediate interactions of immune cells with other leukocytes or body cells. MHC determines compatibility of donors for organ transplant as well as one's susceptibility to an autoimmune disease via crossreacting immunization. In humans, MHC is also called human leukocyte antigen (HLA). MEW class I occurs as an alpha chain composed of three domains—α1, α2, α3. The α1 rests upon a unit of the non-MHC molecule beta2 microglobulin (encoded on human chromosome 15). The α3 subunit is transmembrane, anchoring the MEW class I molecule to the cell membrane. The peptide being presented is held by the floor of the peptide-binding groove, in the central region of the α1/α2 heterodimer (a molecule composed of two nonidentical subunits). The genetically encoded and expressed sequence of amino acids, the sequence of residues, of the peptide-binding groove's floor determines which particular peptide residues it binds.

"MHC multimers" as used herein are oligomeric forms of MHC molecules linked together either directly or via a linker. They generally range in size from dimers to octamers; and can be used to display class 1 MHC (MHC-I), class 2 MHC (MHC-II), or non-classical molecules from species such as monkeys, mice, and humans. In some embodiments, the MHC multimers are MHC-I dextramers.

"Sample" or "biological sample" as used herein refers to tissues or body fluids removed from a mammal, preferably human, and which contain $CD8^+$ T cells. Samples can be blood and/or blood fractions, including peripheral blood sample like peripheral blood mononuclear cell (PBMC) sample or blood, bone marrow cell sample. A sample can also include any specific tissues/organ sample of interest, including, without limitation, lymphoid, thymus, pancreas, eye, heart, liver, nerves, intestine, skin, muscle, cartilage, ligament, synovial fluid, and/or joints. The samples can be taken from any individual including a healthy individual or an individual having cells, tissues, and/or an organ afflicted with the unwanted immune response. For example, a sample can be taken from an individual having an allergy, a graft vs. host disease, a cell or organ transplant, or an autoimmune disease or disorder. Methods for obtaining such samples are well known to a person of ordinary skill in the art of immunology and medicine. They include drawing and processing blood and blood components using routine procedures, or obtaining biopsies from the bone marrow or other tissue or organ using standard medical techniques.

The present invention relates to the use of APP peptides (for example APP peptide having the amino acid sequence ALENYITAL (SEQ ID NO: 2)), as biomarkers in identifying APP-specific $CD8^+$ T cells in a sample. In a non-limiting example, the present invention teaches the use of the APP peptide having the sequence ALENYITAL (SEQ ID NO: 2) in identifying, isolating, enriching, and/or expanding a population of $CD8^+$ T cells specific to the APP peptide. In some embodiments, the APP peptides may comprise the amino acid sequence ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6).

Embodiments include compositions comprising a MHC molecule/peptide complex comprising multiple MHC molecules. An MHC molecule/peptide complex can comprise, for example, 2 (dimer), 3 (trimer), 4 (tetramer), 5 (pentamer), 6, 7, 8, 9, 10, 11, 12, 13, 14, 15, or more MHC molecules. In an embodiment, the MHC molecule/peptide complex comprises, consists of or essentially consists of an MHC dextramer complexed with an APP peptide. In an embodiment, the MHC molecule/peptide complex comprises, consists of or essentially consists of an MHC detramer complexed with an APP peptide having the sequence ALENYITAL (SEQ ID NO: 2). In an embodiment, the MHC molecule is an MHC-I molecule. In some embodiments, the APP peptide has the sequence ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6).

Each MHC molecule can form complexes with a peptide. In aspects of this embodiment, a peptide may be an APP peptide, for example, an APP peptide having the sequence ALENYITAL (SEQ ID NO: 2). An MHC molecule/peptide complex can comprise, for example, 2 MHC/peptide complexes (dimer), or 3 MHC/peptide complexes (trimer), or 4 MHC/peptide complexes (tetramer), or 5 MHC/peptide complexes (pentamer), or 6 MHC/peptide complexes, or 7 MHC/peptide complexes, or 8 MHC/peptide complexes, or 9 MHC/peptide complexes, or 10 MHC/peptide complexes, or 11 MHC/peptide complexes, or 12 MHC/peptide complexes, or 13 MHC/peptide complexes, or 14 MHC/peptide complexes, or 15 MHC/peptide complexes, or more. In an embodiment, the MHC molecule is an MHC-I molecule.

A peptide forming a complex with a MHC molecule (for example, MHC-I molecule) includes a conservative variant of that peptide. A conservative variant refers to a peptide that has at least one amino acid substituted by another amino acid or an amino acid analog that has at least one property similar to that of the original amino acid from an exemplary reference peptide. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative substitution can be assessed by a variety of factors, such as, e.g., the physical properties of the amino acid being substituted (Table 1) or how the original amino acid would tolerate a substitution (Table 2). The selections of which amino acid can be substituted for another amino acid in a peptide disclosed herein are known to a person of ordinary skill in the art. A conservative variant can function in substantially the same manner as the exemplary reference peptide, and can be substituted for the exemplary reference peptide in any aspect of the present invention. Non-limiting examples of exemplary reference peptides include a peptide having the sequence ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6).

TABLE 1

Amino Acid Properties

| Property | Amino Acids |
| --- | --- |
| Aliphatic | G, A, I, L, M, P, V |
| Aromatic | F, H, W, Y |
| C-beta branched | I, V, T |
| Hydrophobic | C, F, I, L, M, V, W |
| Small polar | D, N, P |
| Small non-polar | A, C, G, S, T |
| Large polar | E, H, K, Q, R, W, Y |
| Large non-polar | F, I, L, M, V |
| Charged | D, E, H, K, R |
| Uncharged | C, S, T |
| Negative | D, E |
| Positive | H, K, R |
| Acidic | D, E |
| Basic | K, R |
| Amide | N, Q |

TABLE 2

Amino Acid Substitutions

| Amino | Favored Substitution | Neutral Substitutions | Disfavored substitution |
| --- | --- | --- | --- |
| A | G, S, T | C, E, I, K, M, L, P, Q, R, | D, F, H, N, Y, W |
| C | F, S, Y, W | A, H, I, M, L, T, V | D, E, G, K, N, P, Q, R |
| D | E, N | G, H, K, P, Q, R, S, T | A, C, I, L, |
| E | D, K, Q | A, H, N, P, R, S, T | C, F, G, I, L, M, V, W, Y |
| F | M, L, W, Y | C, I, V | A, D, E, G, H, K, N, P, |
| G | A, S | D, K, N, P, Q, R | C, E, F, H, I, L, M, T, V, Y |
| H | N, Y | C, D, E, K, Q, R, S, T, W | A, F, G, I, L, M, P, V |
| I S, W | V, L, M | A, C, T, F, Y | D, E, G, H, K, N, P, Q, R, |
| K | Q, E, R | A, D, G, H, M, N, P, S, T | C, F, I, L, V, W, Y |
| L S, T | F, I, M, V | A, C, W, Y | D, E, G, H, K, N, P, Q, R, |
| M | F, I, L, V | A, C, R, Q, K, T, W, Y | D, E, G, H, N, P, S |
| N | D, H, S | E, G, K, Q, R, T | A, C, F, I, L, M, P, V, W, |
| P | — | A, D, E, G, K, Q, R, S, T | C, F, H, I, L, M, N, V, W, |
| Q | E, K, R | A, D, G, H, M, N, P, S, T | C, F, I, L, V, W, Y |
| R | K, Q | A, D, E, G, H, M, N, P, | C, F, I, L, V, W, Y |
| S | A, N, T | C, D, E, G, H, K, P, Q, | F, I, L, M, V, W, Y |
| T | S | A, C, D, E, H, I, K, M, | F, G, L, W, Y |

TABLE 2-continued

Amino Acid Substitutions

| Amino | Favored Substitution | Neutral Substitutions | Disfavored substitution |
| --- | --- | --- | --- |
| V S, W | I, L, M | A, C, F, T, Y | D, E, G, H, K, N, P, Q, R, |
| W | F, Y | H, L, M | A, C, D, E, G, I, K, N, P, |
| Y S, T | F, H, W | C, I, L, M, V | A, D, E, G, K, N, P, Q, R, |

Matthew J. Betts and Robert, B. Russell, Amino Acid Properties and Consequences of Substitutions, pp. 289-316, In Bioinformatics for Geneticists, (eds Michael R. Barnes, Ian C. Gray, Wiley, 2003).

An APP peptide may be of any length so long as the APP peptide can specifically bind to $CD8^+$ T cells expressing a receptor for the APP peptide. In an embodiment, an APP peptide is the peptide having the sequence ALENYITAL (SEQ ID NO: 2) as disclosed herein. In exemplary embodiments, the APP peptide has the sequence of any one or more of ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6). In some embodiments, an APP peptide can comprise from, for example, 2 to 20 amino acids, 3 to 20 amino acids, 4 to 20 amino acids, 5 to 20 amino acids, 6 to 20 amino acids, 7 to 20 amino acids, 8 to 20 amino acids, 9 to 20 amino acids, 10 to 20 amino acids, 11 to 20 amino acids, 12 to 20 amino acids, 4 to 18 amino acids, 5 to 18 amino acids, 6 to 18 amino acids, 7 to 18 amino acids, 8 to 18 amino acids, 9 to 18 amino acids, 10 to 18 amino acids, 11 to 18 amino acids, 12 to 18 amino acids, 4 to 16 amino acids, 5 to 16 amino acids, 6 to 16 amino acids, 7 to 16 amino acids, 8 to 16 amino acids, 9 to 16 amino acids, 10 to 16 amino acids, 11 to 16 amino acids, 12 to 16 amino acids, 4 to 15 amino acids, 5 to 15 amino acids, 6 to 15 amino acids, 7 to 15 amino acids, 8 to 15 amino acids, 9 to 15 amino acids, 10 to 15 amino acids, 11 to 15 amino acids, 12 to 15 amino acids, 4 to 12 amino acids, 5 to 12 amino acids, 6 to 12 amino acids, 7 to 12 amino acids, 8 to 12 amino acids, 9 to 12 amino acids, or 10 to 12 amino acids. In still other aspects of this embodiment, an APP peptide can comprise from, for example, 1 to 11 amino acids, 2 to 11 amino acids, 3 to 11 amino acids, 4 to 11 amino acids, 5 to 11 amino acids, 6 to 11 amino acids, 1 to 10 amino acids, 2 to 10 amino acids, 3 to 10 amino acids, 4 to 10 amino acids, 5 to 10 amino acids, 6 to 10 amino acids, 1 to 9 amino acids, 2 to 9 amino acids, 3 to 9 amino acids, 4 to 9 amino acids, 5 to 9 amino acids, 6 to 9 amino acids, 1 to 8 amino acids, 2 to 8 amino acids, 3 to 8 amino acids, 4 to 8 amino acids, 5 to 8 amino acids, 6 to 8 amino acids, 1 to 7 amino acids, 2 to 7 amino acids, 3 to 7 amino acids, 4 to 7 amino acids, 5 to 7 amino acids, 6 to 7 amino acids, 1 to 6 amino acids, 2 to 6 amino acids, 3 to 6 amino acids, 4 to 6 amino acids, or 5 to 6 amino acids. It should be understood by the skilled artisan that the substitutions described herein are equally relevant to all the peptides of APP and that an APP peptide having the sequence ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6) are examples of an APP peptide.

An APP peptide can also comprise conservative variants to an APP peptide. In an embodiment, a conservative variant of an APP peptide is a conservative variant of a peptide having the sequence ALENYITAL (SEQ ID NO: 2), KLVF-FAEDV (SEQ ID NO: 3), LMVGGVVIA (SEQ ID NO: 4), GLMVGGVVI (SEQ ID NO: 5), or VIVITLVML (SEQ ID NO: 6) peptide can be, for example, an amino acid sequence having at least 50%, 55%, 60%, 65%, 70%, 75%, at least 80%, at least 85%, at least 90%, at least 95%, at least 97%, or at least 98%, or at least 99% amino acid sequence identity to the ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6) peptides. In other aspects of this embodiment, a conservative variant of the APP peptide can be, for example, an amino acid sequence having at most 50%, 55%, 60%, 65%, 70%, 75%, at most 80%, at most 85%, at most 90%, at most 95%, at most 97%, or at most 98%, or at most 99% amino acid sequence identity to the ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6) peptides.

An MHC molecule/peptide complex selectively binds to CD8+ T cells expressing a receptor for the peptide forming the complex. In an embodiment, an MHC molecule/APP peptide complex selectively binds to CD8+ T cells expressing a receptor for an APP peptide. In an aspect of this embodiment, an MHC molecule/ALENYITAL (SEQ ID NO: 2) peptide complex selectively binds to CD8+ T cells expressing a receptor for an ALENYITAL (SEQ ID NO: 2) peptide.

Selective binding of a peptide disclosed herein includes binding properties such as, e.g., binding affinity, binding specificity, and binding avidity. Binding affinity refers to the length of time a peptide disclosed herein resides at its binding site or moiety, and can be viewed as the strength with which a peptide binds its binding site or moiety. Binding affinity can be described a peptide's equilibrium dissociation constant (KD), which is defined as the ratio Kd/Ka at equilibrium, where Ka is a peptide's association rate constant and kd is a peptide's dissociation rate constant. Binding affinity is determined by both the association and the dissociation and alone, neither high association or low dissociation can ensure high affinity. The association rate constant (Ka), or on-rate constant ($K_{on}$), measures the number of binding events per unit time, or the propensity of a peptide's and its binding site or moiety to associate reversibly into its peptide-moiety complex. The association rate constant is expressed in $M^{-1}$ $s^{-1}$, and is symbolized as follows: $[PT] \times [BS] \times K_{on}$. The larger the association rate constant, the more rapidly a peptide disclosed herein binds to its binding site or moiety, or the higher the binding affinity between a peptide disclosed herein and its binding site or moiety. The dissociation rate constant (Kd), or off-rate constant (Koff), measures the number of dissociation events per unit time propensity of agent-moiety complex to separate (dissociate) reversibly into its component molecules, namely the peptide disclosed herein and its binding site or moiety. The dissociation rate constant is expressed in $s^{-1}$, and is symbolized as follows: $[PT+BS] \times K_{off}$. The smaller the dissociation rate constant, the more tightly bound a peptide is to its binding site or moiety, or the higher the binding affinity between peptide disclosed herein and its binding site or moiety. The equilibrium dissociation constant (KD) measures the rate at which new agent-moiety complexes formed equals the rate at which agent-moiety complexes dissociate at equilibrium. The equilibrium dissociation constant is expressed in M, and is defined as $K_{off}/K_{on} = [CA] \times [BS]/[CA+BS]$, where [PT] is the molar concentration of a peptide, [BS] is the molar concentration of the binding site or moiety, and [PT+BS] is the molar concentration of the peptide-site complex, where all concentrations are of such components when the system is at equilibrium. The smaller the equilibrium dissociation constant, the more tightly bound a peptide is to its binding site or moiety, or the higher the binding affinity between a peptide n and its binding site or moiety.

In an embodiment, the binding affinity of an APP peptide may have an association rate constant of, e.g., less than $1 \times 10^5$ $M^{-1}$ $s^{-1}$, less than $1 \times 10^6$ $M^{-1}$ $s^{-1}$, less than $1 \times 10^7$ $M^{-1}$ $s^{-1}$, or less than $1 \times 10^8$ $M^{-1}$ $s^{-1}$. In another embodiment, the binding affinity of an APP peptide disclosed herein may have an association rate constant of, e.g., more than $1 \times 10^5$ $M^{-1}$ $s^{-1}$, more than $1 \times 10^6$ $M^{-1}$ $s^{-1}$, more than $1 \times 10^7$ $M^{-1}$ $s^{-1}$, or more than $1 \times 10^8$ $M^{-1}$ $s^{-1}$. In other aspects, the binding affinity of an APP peptide disclosed herein may have an association rate constant between $1 \times 10^5$ $M^{-1}$ $s^{-1}$ to $1 \times 10^8$ $M^{-1}$ $s^{-1}$, $1 \times 10^6$ $M^{-1}$ $s^{-1}$ to $1 \times 10^8$ $M^{-1}$ $s^{-1}$, $1 \times 10^5$ $M^{-1}$ $s^{-1}$ to $1 \times 10^7$ $M^{-1}$ $s^{-1}$, or $1 \times 10^6$ $M^{-1}$ $s^{-1}$ to $1 \times 10^7 M^{-1}$ $s^{-1}$.

In another embodiment, the binding affinity of an APP peptide may have a disassociation rate constant of less than $1 \times 10^{-3}$ $s^{-1}$, less than $1 \times 10^{-4}$ $s^{-1}$, or less than $1 \times 10^{-5}$ $s^{-1}$. In other aspects of this embodiment, the binding affinity of an APP peptide disclosed herein may have a disassociation rate constant of, e.g., less than $1.0 \times 10^{-4}$ $s^{-1}$, less than $2.0 \times 10^{-4}$ $s^{-1}$, less than $3.0 \times 10^{-4}$ $s^{-1}$, less than $4.0 \times 10^{-4}$ $s^{-1}$, less than $5.0 \times 10^{-4}$ $s^{-1}$, less than $6.0 \times 10^{-4}$ $s^{-1}$, less than $7.0 \times 10^{-4}$ $s^{-1}$, less than $8.0 \times 10^{-4}$ $s^{-1}$, or less than $9.0 \times 10^{-4}$ $s^{-1}$. In another embodiment, the binding affinity of an APP peptide disclosed herein may have a disassociation rate constant of, e.g., more than $1 \times 10^{-3}$ $s^{-1}$, more than $1 \times 10^{-4}$ $s^{-1}$, or more than $1 \times 10^{-5}$ $s^{-1}$. In other aspects of this embodiment, the binding affinity of an APP peptide disclosed herein may have a disassociation rate constant of, e.g., more than $1.0 \times 10^{-4}$ $s^{-1}$, more than $2.0 \times 10^{-4}$ $s^{-1}$, more than $3.0 \times 10^{-4}$ $s^{-1}$, more than $4.0 \times 10^{-4}$ $s^{-1}$, more than $5.0 \times 10^{-4}$ $s^{-1}$, more than $6.0 \times 10^{-4}$ $s^{-1}$, more than $7.0 \times 10^{-4}$ $s^{-1}$, more than $8.0 \times 10^{-4}$ $s^{-1}$, or more than $9.0 \times 10^{-4}$ $s^{-1}$.

In another embodiment, the binding affinity of an APP peptide may have an equilibrium disassociation constant of less than 0.500 nM. In aspects of this embodiment, the binding affinity of an APP peptide disclosed herein may have an equilibrium disassociation constant of, e.g., less than 0.500 nM, less than 0.450 nM, less than 0.400 nM, less than 0.350 nM, less than 0.300 nM, less than 0.250 nM, less than 0.200 nM, less than 0.150 nM, less than 0.100 nM, or less than 0.050 nM. In another embodiment, the binding affinity of an APP peptide disclosed herein may have an equilibrium disassociation constant of more than 0.500 nM. In aspects of this embodiment, the binding affinity of an APP peptide disclosed herein may have an equilibrium disassociation constant of, e.g., more than 0.500 nM, more than 0.450 nM, more than 0.400 nM, more than 0.350 nM, more than 0.300 nM, more than 0.250 nM, more than 0.200 nM, more than 0.150 nM, more than 0.100 nM, or more than 0.050 nM.

Binding specificity is the ability of a peptide (such as an APP peptide) to discriminate between a molecule containing its binding site or moiety and a molecule that does not contain a binding site or moiety for the peptide. One way to measure binding specificity is to compare the Kon association rate of a peptide for a molecule containing its binding site or moiety relative to the Kon association rate of a peptide for a molecule that does not contain its binding site. For example, comparing the association rate constant (Ka) of an APP peptide for an APP receptor relative to a receptor not containing an APP peptide binding site.

In aspects of this embodiment, an APP peptide that selectively binds to a molecule containing an APP peptide binding site or moiety can have an association rate constant (Ka) for a molecule not containing an APP peptide binding site or moiety of, e.g., less than $1\times10^0$ $M^{-1}$ $s^{-1}$, less than $1\times10^1$ $M^{-1}$ $s^{-1}$, less than $1\times10^2$ $M^{-1}$ $s^{-1}$, less than $1\times10^3$ $M^{-1}$ $s^{-1}$ or less than $1\times10^4$ $M^{-1}$ $s^{-1}$. In other aspects of this embodiment, an APP peptide disclosed herein that selectively binds to a molecule containing an APP peptide binding site or moiety can have an association rate constant (Ka) for a molecule not containing an APP peptide binding site or moiety of, e.g., at most $1\times10^0$ $M^{-1}$ $s^{-1}$, at most $1\times10^1 M^{-1}$ $s^{-1}$, at most $1\times10^2 M^{-1}$ $s^{-1}$, at most $1\times10^3 M^{-1}$ $s^{-1}$ or at most $1\times10^0$ $M^{-1}$ $s^{-1}$.

In aspects of this embodiment, an APP peptide that selectively binds to a molecule containing an APP peptide binding site or moiety can have an association rate constant (Ka) for a molecule not containing an APP peptide binding site or moiety of, e.g., less than $1\times10^0$ $M^{-1}$ $s^{-1}$ less than $1\times10^1 M^{-1}$ $s^{-1}$, less than $1\times10^2$ $M^{-1}$ $s^{-1}$, less than $1\times10^3$ $M^{-1}$ $s^{-1}$ or less than $1\times10^3$ $M^{-1}$ $s^{-1}$. In other aspects of this embodiment, an APP peptide disclosed herein that selectively binds to a molecule containing an APP peptide binding site or moiety can have an association rate constant (Ka) for a molecule not containing an APP peptide binding site or moiety of, e.g., at most $1\times10^0$ $M^{-1}$ $s^{-1}$, at most $1\times10^1 M^{-1}$ $s^{-1}$, at most $1\times10^2 M^{-1}$ $s^{-1}$, at most $1\times10^3 M^{-1}$ $s^{-1}$ or at most $1\times10^0$ $M^{-1}$ $s^{-1}$.

The binding specificity of a APP peptide that selectively binds to a molecule containing its binding site or moiety can also be characterized as an activity ratio that such a peptide disclosed herein can exert activity through binding to a molecule containing its binding site or moiety relative to a molecule not containing its binding site or moiety. In aspects of this embodiment, an APP peptide has an activity ratio through a molecule containing its binding site or moiety relative to a molecule not containing its binding site or moiety of, e.g., at least 2:1, at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, or at least 40:1. In other aspects of this embodiment, an APP peptide has an activity ratio through a molecule containing its binding site or moiety relative to a molecule not containing its binding site or moiety of, e.g., at least 2:1, at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, or at least 40:1.

In embodiments, compositions disclosed herein can include an imaging probe such as, for example, radioactive probes, magnetic resonance (MR) probes, optical probes, (fluorescence, Raman, photoacoustic), ultrasound probes, CT probes, multimodality imaging probes, and the like.

Embodiments of the present invention disclose, in part, a composition comprising a population of CD8+ T cells obtained according to the methods disclosed herein. In an embodiment, a composition comprising a population of CD8+ T cells disclosed herein is made according to a method of obtaining a population of CD8+ T cells as disclosed herein. In another embodiment, a composition comprising a population of CD8+ T cells disclosed herein is made according to a method of expanding a population of CD8+ T cells as disclosed herein.

Certain embodiments of the present invention disclose, in part, a method of identifying a population of CD8+ T cells. In one embodiment, the method disclosed herein comprises screening a sample comprising a population of T cells to detect CD8+ T cells that recognize MHC/APP peptide complexes comprising peptide having the sequence ALENYITAL (SEQ ID NO: 2). In embodiments recognition of the MHC/APP peptide complex comprising peptide having the sequence ALENYITAL (SEQ ID NO: 2) causes the CD8+ T cell to bind to the complex.

In an embodiment, screening a sample comprising a population of T-cells to detect CD8+ T cells that recognize a particular APP peptide/MHC complex is accomplished using flow cytometry. In an embodiment, screening a sample comprising a population of T-cells to detect CD8+ T cells that recognize a particular APP peptide/MHC complex is accomplished using a cell sorter. After exposing a sample comprising a population of T-cells to an MHC/APP peptide composition disclosed herein, a cell sorter is used to identify T cells that recognize the APP peptide/MHC complex. Cell sorters are well known to persons of ordinary skill in the art and generally are capable of separating a complex mixture of cells into fractions of a single cell type. Typically, the cells to be sorted are introduced as a thin jet of carrier liquid emanating from a small nozzle orifice. Shortly after leaving the nozzle, the hydrodynamically-focused stream of fluid passes through the waist of one or more tightly focused beams of light, usually laser light. A number of detectors are aimed at the point where the stream passes through the light beam: one in line with the light beam (Forward Scatter or FSC) and several perpendicular to it (Side Scatter or SSC) and one or more fluorescent detectors. Each suspended particle from 0.2 µm to 150 µm passing through the beam scatters the ray, and fluorescent chemicals found in the particle or attached to the particle may be excited into emitting light at a longer wavelength than the light source. This combination of scattered and fluorescent light is picked up by the detectors, and, by analyzing fluctuations in brightness at each detector (one for each fluorescent emission peak), it is then possible to derive various types of information about the physical and chemical structure of each individual particle. The data generated by flow cytometers can be plotted in a single dimension, to produce a histogram, or in two-dimensional dot plots or even in three dimensions. The regions on these plots can be sequentially separated, based on fluorescence intensity, by creating a series of subset extractions, termed "gates." Some flow cytometers on the market have eliminated the need for fluorescence and use only light scatter for measurement. Other flow cytometers form images of each cell's fluorescence, scattered light, and transmitted light.

In an aspect of this embodiment, screening a sample comprising a population of T-cells to detect CD8+ T cells that recognize a particular APP peptide/MHC complex is accomplished by flow cytometer using a fluorescently-labeled biomarker ligand. Flow cytometric sorting is a specialized type of flow cytometry. It provides a method for sorting a heterogeneous mixture of biological cells into two or more containers, one cell at a time, based upon the specific light scattering and fluorescent characteristics of each cell. It is a useful scientific instrument, as it provides fast, objective and quantitative recording of fluorescent signals from individual cells as well as physical separation of cells of particular interest. A flow cytometric sorter can easily analyze cells at speeds greater than 200,000 events per second. Generally, the physics of the carrier fluid, however, and the statistics of distributing the cells among the droplets limits sort rates to about 50,000 cells per second. This combination of speed and reliable separation allows individual cells to be isolated or enriched for other uses.

In another embodiment, screening a sample comprising a population of T-cells to detect CD8+ T cell that recognize a particular APP peptide/MHC complex is accomplished by magnetic-activated cell sorting (MACS) using a magnetically labeled MHC/peptide complex. Magnetic nanoparticles may comprise super-paramagnetic nanoparticles composed of iron oxide and a polysaccharide coat. The magnetic nanoparticles are preferably small enough to remain in colloidal suspension, which permits rapid, efficient binding to an APP peptide/MHC complex. In aspects of this embodiment, the magnetic nanoparticles are between about 1 nm in diameter to about 100 nm in diameter, such as, e.g., about 25 nm in diameter, 50 nm in diameter, 75 nm in diameter, or 100 nm in diameter. In other aspects of this embodiment, the magnetic nanoparticles have a volume of, e.g., about one-millionth that of a typical mammalian cell, about five-millionth that of a typical mammalian cell, or about ten-millionth that of a typical mammalian cell. The magnetic nanoparticles preferably do not interfere with flow cytometry, are biodegradable, and have negligible effects on cellular functions. MHC/peptide complex coupling to the magnetic nanoparticles may be direct or indirect.

In another embodiment, screening a sample comprising a population of T-cells to detect CD8+ T cells that recognize a particular APP peptide/MHC complex is accomplished by solid-phase attachment. In an aspect, screening a sample comprising a population of T-cells to determine those that recognize a particular APP peptide/MHC complex is accomplished by panning or solid-phase affinity chromatography using resin comprising an APP peptide/MHC complex as disclosed herein. In an aspect, screening a sample comprising a population of T-cells cells to determine those that recognize a particular APP peptide/MHC complex is accomplished by solid-phase magnetic beads using a magnetically labeled MHC/peptide complex as disclosed herein. See, e.g., US Patent Application Publication 2005/0186207, which is incorporated by reference in its entirety.

In another embodiment, screening a sample comprising a population of T-cells to detect CD8+ T cells that recognize a particular APP peptide/MHC complex is accomplished by ELISPOT assay, for example, as described in Kuzushima, K, Hayashi, N, Kimura, H, Tsurumi, T. 2001. Blood 98:1872-81. Vials of frozen PBMCs from AD and control patients are incubated with and without antigenic peptide(s) at 37° C. for 6 days, prior to transfer of cells to a BD™ Elispot kit plate, and restimulation overnight with antigenic peptide. PHA lectin is used to stimulate the cells in the absence of antigenic peptide as positive stimulation control. Antibody to the cytokine, IFNγ, is then added and plates incubated for 2 hours at room temperature per kit protocol, followed by antibody detection using Streptavidin-HRP, and spot development by colorimetric staining for 5-20 minutes. Spots are enumerated via a third party reading facility and inspected automatically using an Elispot plate reader (see Example 9 for Elispot protocol).

Provided herein is an assay for determining the likelihood of late onset Alzheimer's disease (LOAD) in a subject in need thereof. The assay includes obtaining a sample from the subject; assaying the sample to determine the level of amyloid precursor protein (APP)-specific CD8+ T cells; and determining that the subject has an increased likelihood of LOAD if the level of the APP-specific CD8+ T cells are higher relative to the reference sample, or determining that the subject has a decreased likelihood of LOAD if the level of the APP-specific CD8+ T cells are same as or lower relative to the reference sample. In an embodiment, the APP peptide comprises, consists of or essentially consists of the sequence ALENYITAL (SEQ ID NO: 2). In other embodiments, the APP peptide comprises, consists of or essentially consists of the sequence of one or more of ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6), or combinations thereof. In various embodiments, APP-specific CD8+ T-cells are detected by the methods described herein, including but not limited to FACS, MACS or ELISPOT. The ELISPOT assay, in which the same APP peptides are used to stimulate patients' peripheral blood cells (PBMC), may also be adapted, in some embodiments, to quantify the CD8+ T cells responding to them, in place of FACS or MACS (see Examples).

Other aspects of the invention disclose methods for detecting APP peptide-specific CD8+ T cells. In aspects, the disclosed methods comprise the step of screening a sample comprising a population of T-cells to detect a population of T cells that recognize an APP peptide/MHC complex. In other aspects, the disclosed methods further include isolating APP peptide-specific CD8+ T cells and/or expanding the population of APP peptide-specific CD8+ T cells.

Yet other aspects of the present invention disclose methods for isolating APP peptide-specific CD8+ T cells. In aspects, the disclosed methods comprise the steps of a) screening a sample comprising a population of T-cells to detect a population of T cells that recognize an APP peptide/MHC complex, and b) isolating this subpopulation of T cells that recognize an APP peptide/MHC complex, thereby obtaining the population of T cells that recognize an APP peptide/MHC complex. In other aspects, the disclosed methods further include expanding the population of APP peptide-specific CD8+ T cells.

Other aspects of the present invention disclose methods for detecting LOAD in an individual. In aspects, the disclosed methods comprise the steps of a) administering to the individual a composition comprising APP-peptide/MHC complex, and b) screening the patient to determine the extent of recognition between the composition and CD8+ T cells that recognize APP peptides. In some embodiments, the composition further includes an imaging probe. In one embodiment, an increase in binding between APP peptide/MHC complex and CD8+ T cells that recognize APP peptides relative to the reference value is indicative of presence of LOAD. In an embodiment, the APP peptide comprises, consists of or essentially consists of the sequence ALENYITAL (SEQ ID NO: 2). In other embodiments, the APP peptide comprises, consists of or essentially consists of the sequence of one or more of ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6), or combinations thereof.

Also provided herein are methods for detecting LOAD in an individual. The methods include providing a sample from a subject, contacting the sample with a composition comprising APP peptide/MHC complex and determining the level of binding of the composition to the sample. In some embodiments, the composition further includes an imaging probe. In an embodiment the sample comprises CD8+ T cells that recognize APP peptides. In an embodiment, an increase in binding relative to the reference sample is indicative of presence of LOAD. In an embodiment, the composition further comprises an imaging probe. In an embodiment, the APP peptide comprises, consists of or essentially consists of the sequence ALENYITAL (SEQ ID NO: 2). In other embodiments, the APP peptide comprises, consists of or essentially consists of the sequence of one or more of ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6) or combinations thereof.

Other aspects of the present invention disclose methods for prognosticating LOAD in an individual. In aspects, the methods include the steps of a) administering to the individual a composition comprising APP peptide/MHC complex, and b) screening the individual to determine the extent of binding between the composition and CD8+ T cells that recognize APP peptides. In some embodiments, the composition further includes an imaging probe. In one embodiment, an increase in binding between APP peptide/MHC complex and CD8+ T cells that recognize APP peptides relative to the reference value may be indicative of poor prognosis (for example, increased likelihood of LOAD). In another embodiment, a decrease in binding between APP peptide/MHC complex and CD8+ T cells that recognize APP peptides relative to the reference value may be indicative of good prognosis (for example, decreased likelihood of LOAD). In an embodiment, the APP peptide comprises, consists of or essentially consists of the sequence ALENYITAL (SEQ ID NO: 2). In other embodiments, the APP peptide comprises, consists of or essentially consists of the sequence of one or more of ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6), or combinations thereof.

Also provided herein are methods for prognosticating LOAD in a subject. The method includes providing a sample from the subject and contacting the sample with a composition comprising APP peptide/WIC complex, as described herein. In an embodiment, the presence or an increase in the level of APP-specific CD8+ T cells relative to reference value is indicative of poor prognosis (for example, increased likelihood of LOAD). In an embodiment, the absence or a decrease in the level of APP-specific CD8+ T cells relative to reference value is indicative of good prognosis (for example, decreased likelihood of LOAD). In some embodiments, the existence or the level of APP-specific CD8+ T cells is used to prognosticate overall survival. In an embodiment, the subject has undergone treatment for LOAD. In another embodiment, the subject has not undergone treatment for LOAD. In an embodiment, the subject exhibits risk factors for LOAD. In exemplary embodiments, the risk factors for LOAD include but are not limited to any one or more of mild cognitive impairment (MCI), traumatic brain injury, expression of APOEε4 allele, diabetes, cardiovascular disease, or a combination thereof. In some embodiments, the traumatic brain injury occurred in the subject within 12-36 months of testing for LOAD by the methods described herein. In an embodiment, the APP peptide comprises, consists of or essentially consists of the sequence ALENYITAL (SEQ ID NO: 2). In other embodiments, the APP peptide comprises, consists of or essentially consists of the sequence of one or more of ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6) or combinations thereof.

Further provided herein are methods comprising obtaining the results of a diagnostic test that determines whether a subject is likely to have LOAD and treating the subject for LOAD using therapeutic methods, for example, those described herein, if it is determined that the subject likely has LOAD. In some embodiments, determining whether a subject is likely to have LOAD includes obtaining a sample from the subject; assaying the sample to determine the level of amyloid precursor protein (APP)-specific CD8+ T cells; and determining that the subject has an increased likelihood of LOAD if the level of the APP-specific CD8+ T cells are higher relative to the reference sample, or determining that the subject has a decreased likelihood of LOAD if the level of the APP-specific CD8+ T cells are same as or lower relative to the reference sample. In an embodiment, the APP peptide comprises, consists of or essentially consists of the sequence ALENYITAL (SEQ ID NO: 2). In other embodiments, the APP peptide comprises, consists of or essentially consists of the sequence of one or more of ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6) or combinations thereof.

Also provided herein are treatment methods comprising administering a therapeutic agents (for example, those described herein) to a subject diagnosed with having LOAD. In some embodiments, diagnosis of LOAD includes obtaining a sample from the subject; assaying the sample to determine the level of amyloid precursor protein (APP)-specific CD8+ T cells; and determining that the subject has an increased likelihood of LOAD if the level of the APP-specific CD8+ T cells are higher relative to the reference sample, or determining that the subject has a decreased likelihood of LOAD if the level of the APP-specific CD8+ T cells are same as or lower relative to the reference sample. In an embodiment, the APP peptide comprises, consists of or essentially consists of the sequence ALENYITAL (SEQ ID NO: 2). In other embodiments, the APP peptide comprises, consists of or essentially consists of the sequence of one or more of ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6) or combinations thereof.

Further provided herein are methods for assessing efficacy of treatment of LOAD in a subject. In aspects, the methods include the steps of a) administering to a patient a composition comprising APP-peptide/MHC complex, and b) screening the patient to determine the extent of binding between the composition and CD8+ T cells that recognize APP peptides. In some embodiments, the composition further includes an imaging probe. In one embodiment, a decrease in binding between APP peptide/MHC complex and CD8+ T cells that recognize APP peptides relative to the reference value indicates that the treatment of APP is effective (for example, the treatment exhibits increased efficacy). In an embodiment, the subject has been receiving the treatment for APP for 0-7 days, 2 weeks, one month, six months, one year, two years, 5 years or combinations thereof. In some embodiments, the treatment for LOAD includes existing therapies for Alzheimer's disease. In some embodiments, the treatment for LOAD includes the use of pharmaceutical compositions described herein. In an embodiment, the APP peptide comprises, consists of or essentially consists of the sequence ALENYITAL (SEQ ID NO: 2). In other embodiments, the APP peptide comprises, consists of or essentially consists of the sequence of one or more of ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6) or combinations thereof.

Also provided herein are methods for assessing efficacy of treatment of LOAD in a subject. The method includes providing a sample from and subject and contacting the sample with a composition comprising APP peptide/MHC complex, as described herein and determining the extent of binding between the composition and CD8+ T cells that recognize APP peptides. In some embodiments, the composition further includes an imaging probe. In one embodiment, a decrease in binding between APP peptide/MHC complex and CD8+ T cells that recognize APP peptides relative to the reference value indicates that the treatment of LOAD is effective (for example, the treatment exhibits increased efficacy). In an embodiment, the subject has been receiving the treatment for LOAD for 0-7 days, 2 weeks, one month, six months, one year, two years, 5 years or combinations thereof. In some embodiments, the treatment for LOAD includes existing therapies for Alzheimer's disease. In some embodiments, the treatment for LOAD includes the use of pharmaceutical compositions described herein. In an embodiment, the APP peptide comprises, consists of or essentially consists of the sequence ALENYITAL (SEQ ID NO: 2). In other embodiments, the APP peptide comprises, consists of or essentially consists of the sequence of one or more of ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6), or combinations thereof.

Aspects of the present invention disclose, in part, a method of obtaining a population of CD8+ T cells that recognize an APP peptide/MHC complex. In one embodiment, the method disclosed herein comprises screening a sample comprising a population of T-cells to detect a population of CD8+ T cells that recognize an APP peptide/MHC complex, and isolating this subpopulation of CD8+ T cells that recognize a APP peptide/MHC complex, thereby obtaining the population of CD8+ T cells that recognize a APP peptide/MHC complex. In an embodiment, the APP peptide comprises, consists of or essentially consists of the sequence ALENYITAL (SEQ ID NO: 2). In other embodiments, the APP peptide comprises, consists of or essentially consists of the sequence of one or more of ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6) or combinations thereof.

Aspects of the present invention disclose, in part, a method of obtaining a population of CD8+ T cells that recognize either of two different APP peptide/MHC complexes. In one embodiment, the method disclosed herein comprises screening a sample comprising a population of T-cells to detect a population of CD8+ T cells that recognize either of two APP peptide/MHC complexes, and isolating this subpopulation of CD8+ T cells that recognize either of two APP peptide/MHC complexes, thereby obtaining the population of CD8+ T cells that recognize either of two APP peptide/MHC complexes. In some embodiments, the APP peptide comprises, consists of or essentially consists of the sequence of one or more of ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6) or combinations thereof.

Aspects of the present invention disclose, in part, a method of obtaining a population of CD8+ T cells that recognize any of three different APP peptide/MHC complexes. In one embodiment, the method disclosed herein comprises screening a sample comprising a population of T-cells to detect a population of CD8+ T cells that recognize any of three APP peptide/MHC complexes, and isolating this subpopulation of CD8+ T cells that recognize any of three APP peptide/MHC complexes, thereby obtaining the population of CD8+ T cells that recognize any of three APP peptide/MHC complexes. In some embodiments, the APP peptide comprises, consists of or essentially consists of the sequence of one or more of ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6) or combinations thereof.

Aspects of the present invention disclose, in part, a method of obtaining a population of CD8+ T cells that recognize any of four different APP peptide/MHC complexes. In one embodiment, the method disclosed herein comprises screening a sample comprising a population of T-cells to detect a population of CD8+ T cells that recognize any of four APP peptide/MHC complexes, and isolating this subpopulation of CD8+ T cells that recognize any of four APP peptide/MHC complexes, thereby obtaining the population of CD8+ T cells that recognize any of four APP peptide/MHC complexes. In some embodiments, the APP peptide comprises, consists of or essentially consists of the sequence of one or more of ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6) or combinations thereof.

In some embodiments, the reference value is the mean or median level of binding between APP peptide/MHC complex (for example, in the compositions described herein) and CD8+ T cells that recognize APP peptides in a population of subjects that do not have LOAD. In some embodiments, the reference value is the mean or median level of binding between APP peptide/MHC complex (for example, in the compositions described herein) and CD8+ T cells that recognize APP peptides in a population of subjects that have LOAD but are not undergoing treatment. In some embodiments, the reference value is the mean or median level of binding between APP peptide/MHC complex (for example, in the compositions described herein) and CD8+ T cells that recognize APP peptides in a population of subjects that have LOAD and are undergoing treatment or have undergone treatment for LOAD. In various embodiments, the level of binding between LOAD peptide/MHC complex (for example, in the compositions described herein) and CD8+ T cells that recognize APP peptides is altered (for example, increased or decreased) in the subject compared to the reference value by at least or about 10%, 20%, 30%, 40%, 50%, 60%, 70%, 80%, 90% or 100%. In various embodiments, the level of binding between APP peptide/MHC complex (for example, in the compositions described herein) and CD8+ T cells that recognize APP peptides is altered (for example, increased or decreased) in the subject compared to the reference value by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof.

A population of T-cells can be isolated or enriched using positive selection or negative selection of the cells of interest. Additionally, a population of T-cells that recognize an APP peptide may be isolated or enriched using both positive selection and negative selection of the cells of interest. As used herein, the term "positive selection" refers to the selection of specified cells from a mixture or starting population of cells based upon their recognition of a particular MHC/peptide complex. As used herein, the term "negative selection" refers to the de-selection of specified cells from a mixture or starting population of cells based upon their non-recognition of a particular MHC/peptide complex.

In aspects of this embodiment, a population of T-cells that recognize a particular MHC/APP peptide complex comprising an APP peptide is enriched by, e.g., at least 20%, at least 30%, at least 40% at least 50%, or at least 60%, at least 70%, at least 80%, or at least 90% as compared to the total number of cells from the source population of cells. In other aspects of this embodiment, a population of T-cells that recognize a particular MHC/APP peptide complex comprising an APP peptide is enriched by, e.g., at least two-fold, at least four-fold, at least eight-fold, at least ten-fold, at least 20-fold, at least 50-fold, or at least 100-fold as compared to the total number of cells from the source population of cells.

In other aspects of this embodiment, a population of T-cells that recognize a particular MHC/APP peptide complex comprising an APP peptide is enriched to, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 98% of the total number of cells in the sample. In yet other aspects of this embodiment, a population of T-cells that recognize a particular MHC/APP peptide complex comprising an APP peptide is enriched to, e.g., about 5% to about 95%, about 10% to about 90%, about 15% to about 85%, about 20% to about 80%, about 25% to about 75%, about 30% to about 70%, about 35% to about 65%, about 40% to about 60%, about 45% to about 55%, about 80% to about 85%, about 80% to about 90%, about 80% to about 95%, about 80% to about 98%, about 80% to about 100%, about 85% to about 90%, about 85% to about 95%, about 85% to about 98%, about 85% to about 100%, about 90% to about 95%, about 90% to about 98%, or about 90% to about 100%, of the total number of cells in the. In other aspects of this embodiment, a population of T-cells that recognize a particular MHC/peptide complex comprising an APP peptide is isolated to, e.g., at least 60%, 70%, 80%, at least 85%, at least 90%, at least 95%, or at least 98% from the total number of cells in the sample. In yet other aspects of this embodiment, a subpopulation of T-cells comprising an APP peptide is isolated to, e.g., about 80% to about 85%, about 80% to about 90%, about 80% to about 95%, about 80% to about 98%, about 80% to about 100%, about 85% to about 90%, about 85% to about 95%, about 85% to about 98%, about 85% to about 100%, about 90% to about 95%, about 90% to about 98%, or about 90% to about 100%, from the total number of cells in the sample.

In another aspect, a population of T-cells that recognize a particular MHC/peptide complex comprising an APP peptide is isolated by a negative selection scheme that depletes a population of T-cells that do not recognize a particular MHC/peptide complex comprising an APP peptide cells from the cells in the sample.

A population of T-cells that recognize a particular MHC/peptide complex comprising an APP peptide is obtained based on a characteristic association between the T-cell and the MHC/peptide complex. Cells comprising the desired characteristic may be isolated or enriched using a detection method based on fluorescence, bioluminescence, chemiluminescence, spectroscopic, photochemical, biochemical, immunochemical, chemical, magnetic, size, volume, density, opacity, or other physical means known to one of ordinary skill in the art.

In an embodiment, isolating a subpopulation of T-cells that recognize a particular MHC/peptide complex comprising an APP peptide is accomplished using a cell sorter as disclosed herein. In an aspect of this embodiment, isolating a subpopulation population of T-cells that recognize a particular MHC/peptide complex comprising an APP peptide is accomplished using flow cytometric sorter as disclosed herein.

In an embodiment, expanding a subpopulation of T-cells that recognize a particular MHC/peptide complex comprising an APP peptide can be accomplished by contacting the subpopulation of T-cells with a particular MHC/peptide complex comprising an APP peptide, such as a tetramer comprising the peptide.

A subpopulation of T-cells with a desired recognition capability is administered to an individual. An individual can be any mammal in which modulation of an immune reaction is desired. An individual includes a human, and a human can be a patient. Typically, any individual who is a candidate for a conventional treatment for an immune-based disorder is a candidate for an immune-based disorder treatment disclosed herein. Pre-operative evaluation typically includes routine history and physical examination in addition to thorough informed consent disclosing all relevant risks and benefits of the procedure.

A subpopulation of T-cells with a desired recognition capability is a population of CD8+ T cells. In an aspect of this embodiment, a population of CD8+ T cells comprises T-cells that recognize a particular MHC/peptide complex such as, for example, a particular MHC/APP peptide complex.

Pharmaceutical Composition

In various embodiments, the present invention provides a pharmaceutical composition to treat late-onset Alzheimer's disease. The pharmaceutical composition for use with the methods described herein includes an APP peptide-specific MHC-1 multimer complexed with the APP peptide (MHC/APP) and a pharmaceutically acceptable excipient, wherein the MHC/APP peptide complex is further conjugated to a cytotoxic agent. In an embodiment, the MHC-1 multimer is a WIC dextramer. In an embodiment, the APP peptide comprises, consists of or consists essentially of the amino acid sequence ALENYITAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6). In further embodiments, any other APP peptides of suitable length that are predicted and validated to stably bind HLA (human MHC) molecules can be used with the methods described herein. In some embodiments, SEQ ID NOs: 2-6 represent APP-derived peptides that may stably bind the most common HLA allele in the western world (HLA-A2) that may be readily manufactured; additional peptide/HLA combinations may be utilized depending on patient cohort demographics as would be apparent to a person of skill in the art.

As described herein, in some embodiments, the therapeutic agent for use in the methods described herein comprises an APP peptide-specific MHC multimer conjugated to a cytotoxic agent.

In some embodiments, the cytotoxic agent is a toxin, antibody, heavy metal, radioisotope, or hapten.

In some embodiments, examples of toxins include but are not limited to cyclophosphamide, methrotrexate, Azathioprine, mizoribine, 15-deoxuspergualin, neomycin, staurosporine, genestein, herbimycin A, *Pseudomonas* exotoxin A, saporin, Rituxan, Ricin, gemtuzumab ozogamicin, or Shiga toxin.

In some embodiments, examples of heavy metal are any one or more if inorganic mercurial, organic mercurial, FN18-CRM9 or combinations thereof.

In some embodiments, radioisotopes are incorporated isotopes of iodide, cobalt, selenium, tritium, and phosphorus.

In some embodiments, haptens are DNP or digoxiginin.

The pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, parenteral or enteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by injection. Methods for these administrations are known to one skilled in the art.

The pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins Pa., USA) (2000).

Before administration to patients, formulants may be added to the rAAV vector, the cell transfected with the rAAV vector, or the supernatant conditioned with the transfected cell. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

In some embodiments, polymers as formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar.

Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

Kits

In one embodiment, a kit comprises components necessary for identifying, isolating, and/or enriching a population of CD8+ T cells. In an aspect of this embodiment, a kit for identifying and/or isolating a population of CD8+ T cells that recognize a particular MHC/peptide complex such as, for example, a particular WIC/APP peptide complex. In an embodiment, the WIC-1 multimer is a WIC dextramer. In an embodiment, the APP peptide comprises, consists of or consists essentially of the amino acid sequence ALENYI-TAL (SEQ ID NO: 2), KLVFFAEDV (SEQ ID NO: 3), LMVGGVVIA (SEQ ID NO: 4), GLMVGGVVI (SEQ ID NO: 5), or VIVITLVML (SEQ ID NO: 6). In further embodiments, any other APP peptides of suitable length that are predicted and validated to stably bind HLA (human MHC) molecules can be used with the methods described herein. In some embodiments, SEQ ID NOs: 2-6 represent APP-derived peptides that may stably bind the most common HLA allele in the western world (HLA-A2) that may be readily manufactured; additional peptide/HLA combinations may be utilized depending on patient cohort demographics as would be apparent to a person of skill in the art.

In still another aspect of this embodiment is a kit for identifying, isolating, and/or enriching a population of CD8+ T cells comprising a particular MHC/APP peptide complex, wherein the particular MHC/APP peptide complex comprises an APP peptide.

In another embodiment, a kit comprises components necessary for expanding a population of CD8+ T cells. In an aspect of this embodiment, a kit for expanding a population of CD8+ T cells comprises a stimulatory composition. In aspects of this embodiment, a stimulatory composition comprises an effective amount of an antigen or alloantigen. In still other aspects of this embodiment, a kit for expanding a population of CD8+ T cells may further include positive and/or negative controls and/or instructions for expanding a population of CD8+ T cells by use of the kit's contents. In still other aspects of this embodiment, a kit for expanding a population of CD8+ T cells may further include culture containers like dishes or flasks, culture medium, or any necessary buffers, factors, useful to promote cell growth.

Instructions as disclosed herein may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, tape, or CD, on which the information has been recorded. Yet another means that may be present is a website address which may be used via the internet to access the information at a removed site. Any convenient means may be present in the kits.

The exact nature of the components configured in the inventive kit depends on its intended purpose. In one embodiment, the kit is configured particularly for human subjects.

Instructions for use may be included in the kit. "Instructions for use" typically include a tangible expression describing the technique to be employed in using the components of the kit to effect a desired outcome, such as to treat, reduce the severity of, inhibit or prevent schwannoma in a subject. Optionally, the kit also contains other useful components, such as, measuring tools, diluents, buffers, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of a composition APP/MHC-I. The packaging material generally has an external label which indicates the contents and/or purpose of the kit and/or its components.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Sporadic Alzheimer's disease (AD) is characterized by progressive neurodegeneration with amyloid-beta (Aβ) plaque and neurofibrillary deposits in brain. Rare familial AD is guaranteed by gene mutations that increase Aβ deposition, but aging is the only known cause of sporadic AD. Immune processes such as neuroinflammation contribute to AD pathophysiology, but whether human-specific features of immune aging do so remains unknown. We induced human-like age-related changes in CD8 T cells by homeostatic expansion in nude mice. The resulting homeostatically-induced CD8 T cells ("hiT cells") precipitated human-specific features of AD not seen in current animal models, including neurodegeneration and neurofibrillary deposition. Neurodegeneration, but not proteinopathy, was dependent on both lytic (Perforin1) and proinflammatory (IFNγ) T effector functions. Transfer of hiT cells into wild-type mice decreased neuronal metrics even more quickly, and synergized with brain injury to confer human-specific amyloidosis. Gene expression, effector protein, and immune receptor specificity associated with hiT cells in mice were all significantly elevated in AD brain. These findings introduce a pre-clinical model of AD-like neurodegeneration uniquely based on age-associated physiology. Further dissection of this model should increase our understanding of sporadic AD pathophysiology, identify novel targets for disease intervention, and elucidate physiological mechanisms of age-related tissue destruction.

Example 1: Experimental Methods

Animal & Human Subjects

Female C57BL/6, B6.Foxn1 mice, and congenic and/or syngeneic knockout strains (Jackson Labs) were housed in a pathogen-free vivarium and used on approved protocols according to federal guidelines. All animal procedures were approved prior to performance by the Cedars-Sinai Institutional Animal Care and Use Committee. Animals of the same strain and sex were purchased and utilized at 8-10 weeks of age for recipients, and 5-8 weeks of age for donors, with no additional randomization into groups. Investigators performing analyses were not blinded to group identities, but were blinded to expected outcomes.

Adoptive Transfer of CD8 T Cells

Splenic $CD8^+$ T cells from C57BL/6J female mice (5-7 weeks old) were purified using anti-CD8 immunobeads (Miltenyi Biotech, Sunnyvale, Calif.). Briefly, splenocytes were harvested and homogenized by gently teasing cells from spleen into cold PBS with 2% Fetal Bovine Serum, followed by filtration through a sterile nylon mesh. Red blood cells were eliminated by treatment with distilled water for 5-30 seconds, and macrophages and monocytes removed by adherence to plastic at 37° C. in 5% $CO_2$ in humidified incubator for 90 min with RPMI-1640 medium containing 15 mM Hepes, 2 mM L-glutamine, 100 U/ml penicillin, and 100 mg/ml streptomycin. $3 \times 10^6$ CD8 T cells in 50 µl of PBS were adoptively transferred into female C57BL/6J or B6.Foxn1 nude hosts by tail vein injection. Transfer efficiency was validated by persistence of $\geq 10\%$ $CD8^+$ T cells in splenocyte preparations obtained 3 weeks after T cell transfer from B6.Foxn1 hosts.

Tissue Processing (Brain, Spleen)

Brain and spleen were harvested from mice perfused with PBS. Whole brains were immediately cut 1 mm to the right along the longitudinal fissure (midline). Right hemispheres were flash frozen in −80° C. conditions for protein studies, and left hemisphere were fixed with 4% paraformaldehyde in ddH20 at 4° C. and then permeabilized with either 1% Brij 96 (3 week time point only) or 0.1% Triton X-100 in PBS, 15 min. Homogenization of the brains was achieved with Cell Lysis Buffer (Cell Signaling Technologies, Danvers, Mass.) charged with Protease Inhibitor Cocktail Tablet (Roche, San Francisco, Calif.) at a ratio of 1/10 (Wt/v) and centrifuged 15,000 rpm, 15 minutes at 4° C.

Brain Weight standardization: Upon removal of whole brain from cranium, we removed cerebellum, brainstem, and olfactory bulbs prior to weighing on fine balance.

Western Blot

Cell lysates were separated into Triton soluble, Sarkosyl soluble and Sarkosyl insoluble fractions using sequential incubations of 10% (wt/V) salt sucrose solution and 1% (wt/v) sarkosyl Salt Sucrose Solution. Fractions were loaded into 12% Tris-HCl Precast Gels (Bio-Rad) and electrophoretically separated. Protein presence was confirmed using Ponceau-S red staining solution and subsequently blocked with 5% milk-PBS-0.3% Tween20 for 2 hours at room temperature. Respective Antibodies were diluted in either in 5% milk-PBS-0.3% Tween20 or 5% BSA-PBS-0.3% Tween20. Membranes were incubated in sequential appropriate primary and secondary antibody dilutions for 1 hour at room temperature separated with washing for 15 minutes in PBST-0.3% Tween20 renewing with fresh buffer every 5 minutes. Final membrane wash was for 30 minutes in PBST-0.3% Tween20 renewing with fresh buffer every 5 minutes in between. Membranes were developed with Amersham ECL (enhanced chemiluminescence) detection substrate (GE Healthcare Biosciences; Pittsburgh, Pa.) on Amersham Hyperfilm (GE Healthcare Biosciences; Pittsburgh, Pa.).

ELISA

Amyloid Beta (Aβ) was separated into soluble and insoluble fractions. Soluble Aβ was quantified in Triton X-100 supernatants of homogenized brain tissue. Insoluble pellets remaining after Triton X-100 homogenization were resuspended and incubated in 10 volumes of 5M Guanidine HCl, and insoluble Aβ quantified in the resulting supernatant. Insoluble samples were placed on a rocker at room temperature for 4 hours prior to freeze storage. These sample cohorts were used in ELISA Kits for Soluble and Insoluble Aβ, respectively (Invitrogen, Life Technologies; Grand Island, N.Y.). Plates were analyzed by absorbance microplate reader (SPECTRAmax Plus384; Molecular Devices, Sunnyvale, Calif.) and statistical data analysis was done using Graphpad PRISM software (Graphpad Software; San Diego, Calif.).

Flow Cytometry

Purified T cells stained with respective Abs were analyzed by three-color flow cytometry (FACScan II; BD Biosciences, San Jose, Calif.) to assess purity. Antibodies were incubated with whole-spleen single cell suspension in PBS with 5% FBS, on ice for 30 minutes, followed by a wash with the PBS with 5% FBS. 100,000-300,000 flow events were acquired.

Antibodies for Tissue Staining and Westerns

Free-floating brain sections (8-14 µm thick) were mounted onto Superfrost Plus slides (Fisher Scientific) then treated with Protein block (Dako) for 1 h at RT. Sections were incubated overnight, 4° C. with combinations of primary Abs in blocking solution. Sections were rinsed 4×, 5 min each, in PBS followed by 90 min incubation in fluorochrome- or biotin-conjugated goat or donkey secondary antibodies, with or without curcumin (0.01% in PBS) co-staining, at RT. Sections were washed in PBS and rinsed quickly in sterile water, coverslipped, and mounted with ProLongGold anti-fade mounting media with DAPI (Invitrogen). Bright-field and structured illumination fluorescent images were obtained using a Zeiss AxioImagerZ1 with attached ApoTome and CCD camera (Carl Zeiss Micro imaging). Image analysis of micrographs was performed with Image? software (NIH). Anti-Aβ/APP antibody (ab14220, Abcam for 3 week time point; clone 4G8, Chemicon for all others) was used at 1:500 for immunohistochemistry (IHC) and 1:1000 for Western blot (WB). Anti-pTau pS199/202 antibody (Invitrogen) was used at 1:50 for IHC and 1:100 for WB, with PHFs confirmed with Phospho-PHF-tau pSer202+Thr205 Antibody (AT8), used at 1:2000 for WB. Anti-GFAP (Dako) was used at 1:250 for IHC and WB. Anti-NeuN antibody (Chemicon) was used at 1:100 for IHC and WB. Anti-Iba1 (Wako, Ltd.) was used at 1:200 for IHC. Anti-CD8 (clone 53-6.72, BD Pharmingen) was used at 1:100 for IHC and 1:1000 for WB. Anti-human PRF1 (sc-7417, Santa Cruz Biotech) was used at 1:200 for IF and 1:500 for WB; Anti-human CD8α (ab108292, Abcam) and anti-human GAPDH (ab9485, Abcam) were both used at 1:1000 for WB only. All secondary antibodies (HRP, Alexa Flour-488, -594, -647; Invitrogen) were used at 1:200 for IHC and 1:2000 for WB.

pMHC I and pHLA multimer generation & use: dextramers of established epitopes for self/brain antigen (Trp-2-DCT$_{(180-188)}$/H-2K$^b$), and/or custom APP epitopes with predicted affinities <100 nM (NetMHC version 3.4 prediction), were manufactured by Immudex USA. APP-specific dextramers, APP$_{(470-478)}$/H-2D$^b$ and APP$_{(471-479)}$/HLA-A2 corresponded to the APP epitope with suitable affinity that was most conserved between mouse and human. For staining human brain with dextramers, the manufacturer's protocol (http://www.immudex.com/media/12126/chromogenic_detection.pdf), was followed with the following modifications: 9 μm sections were first incubated 30 min with Sudan Black, then stained with anti-human CD8α (ab108292, Abcam), and fixed in acetone. Fixed sections were incubated with PE-conjugated dextramers at 1:100 dilution overnight at room temperature, followed by incubation with anti-Rabbit Alexa Fluor-488 secondary. Sections were washed, fixed, and examined without counterstaining. HLA-A2$^-$ specimens were not excluded from analysis, but background CD8$^+$ dextramer$^+$ cell counts from negative sections were subtracted from all values prior to plotting to account for non-specific staining and interpretation.

Gallyas Silver Staining

Gallyas silver stain was used to visualize fibrillar aggregates. Free floating sections were placed in 5% Periodic Acid for 3 min, washed twice with dH$_2$O then placed in freshly prepared Silver Iodide solution for 1 min, followed by placing in 0.5% Acetic Acid for 5 min (2×), rinsed in dH$_2$O. Sections were placed in developer for ~10 min until sections turn a pale brown/gray, and then stopped development in 0.5% acetic acid for 5 min, rinsed in dH$_2$O and mounted. Stained sections were examined with Zeiss microscope. Silver stained neurons were counted from dentate gyrus of hippocampus, or determined as a proportion of total neurons in averages of triplicate estimations by the same observer from entorhinal and cingulate cortex, and expressed as proportion of total neurons.

Neuronal Counts

Whole-number neuronal estimates were done using the optical fractionator method of stereological counting with stereological software (Stereo Investigator; MBF Bioscience). Para-median sagittal serial sections spaced 50 μm apart were stained with NeuN. Anatomical regions of interest (ROI), including the cingulate cortex, cornu ammonis 1(CA1), CA2, CA3, and dentate gyrus, were defined according to the Paxinos and Watson mouse brain atlas. A grid was placed randomly over the ROI slated for counting. At random positions within the grid, cells were counted within three-dimensional optical dissectors (50 μm 50 μm 10 μm) with a 100× objective. Within each dissector, 1 μm guard zones at the top and bottom of the section surface were excluded. Section thickness was measured regularly and averaged 12 μm for all sections analyzed, allowing for uniform antibody penetration. Estimated totals by number weighted section thickness were obtained with Stereo Investigator yielding a coefficient of error 0.10. Neuronal densities were calculated by adjusting these totals by the tissue volume of the ROI investigated.

Barnes Maze (BM) Test

Barnes maze is a spatial-learning task that allows subjects to use spatial cues to locate a means of escape from a mildly aversive environment (i.e. the mice are required to use spatial cues to find an escape location). Mice were assessed for their ability to learn the location of an escape box over the course of 9 days in the BM apparatus. The escape hole is constant for each mouse over the five training days. Each mouse was tested three times per day (3 trials) for 4 days, followed by no testing for 2 days, and re-testing on day 7. A 35-60 minute inter-trial interval separates each trial. Each trial began by placing one mouse inside a start box with a bottomless cube positioned centrally on the maze. After 30 seconds, the start box was lifted and the mouse was released from the start box to find the escape hole. Two fluorescent lights located on the ceiling or high above illuminate the testing room. Each trial lasted up to 4 min or until the mouse entered the escape box. The experimenter guided mice that failed to find the escape hole within 4 min, to the correct hole after each training test. Once the mouse entered the escape box, it was allowed to remain in the box for 1 min. Following the 7$^{th}$ day of testing, and never on the same day, mice were tested an additional two-days, in which the escape box was placed in the reverse position on day 8, and replaced in the original position on day 9. The same exact testing procedure was applied to all mice in all groups. The maze and all compartments were cleaned thoroughly with isopropyl alcohol to remove any olfactory cues after each trial, and prior to each day of testing.

Y-Maze Spontaneous Alternation (SA) Test

Y-Maze Alternation Test is used to assess working memory. Spontaneous alternation was measured by individually placing animals in one arm of a symmetric Y-maze made of opaque black acrylic (arms: 40 cm long, 4 cm wide; walls: 30 cm tall), and the sequence of arm entries and total number of entries recorded over a period of 8 min. Mice were tested for SA a single time only.

Flinch-Jump/Fear Conditioning Tests

We first determined there were no significant differences in the nociceptive threshold (pain sensitivity) across treatment groups using the Flinch-Jump Test. Pavlovian Fear Conditioning was then used to assess learning and memory regarding aversive events. The apparatus (Freeze Monitor™, San Diego Instruments, San Diego, Calif.) consisted of a Plexiglas box (25.4×25.4×31.75 cm high) with a stainless steel grid floor. An acoustic stimulus unit is located on top of the box, and the box is ringed with photo beams and optical sensors. The optical sensors were connected to a computer by way of an input matrix, and breaks in the photo beams ere automatically recorded. For testing, on Day 1 individual mice were placed into the test box, and allowed to habituate for 3 minutes. At 3 minutes a tone was presented for 30 sec. 30 sec after termination of the tone, a 0.5 sec foot shock (intensity=mean jump threshold for the treatment group determined by the Flinch-Jump Test) was delivered. The mouse was then removed from the box and returned to its home cage for 2 minutes. The chamber was cleaned and the animal returned to the chamber where the procedure is repeated. The freeze monitor apparatus recorded freezing times throughout the procedure (absence of movement for 5+ seconds, resulting in no beam breaks). On Day 2, context retrieval is determined by placing the mouse into the same test box where it previously received tone and foot shocks, but here the tone and foot shocks were not presented. Freezing time was measured over a 10 min period. On Day 3, cue conditioning was measured after inserting a triangular, plexiglass box into the test box. The mouse was placed into the triangular chamber where they had not previously received tone or foot shocks, but after 1min the auditory tone was delivered for 30 sec and freezing time measured for 10 min. All data from Flinch-Jump and Fear Conditioning Tests was normalized, first within each group to the average of the initial two tests in training on day 1, and then within all experimental groups to the average contextual or cue values of PBS controls, expressed as percent of control, and analyzed by ANOVA, followed where appropriate by Newman-Keuls tests to detect differences among treatment groups.

Open Field Test

The test was carried out in an Open Field apparatus made up of an open topped, clear Plexiglas box, measuring 16"×16" and 15" high. Two rings of photobeams and optical sensors surrounded the box. The optical sensors were connected to a computer by way of an input matrix. Each mouse was placed into the box, and breaks in the beam interruptions automatically recorded and used as a measure of locomotor activity. Each mouse was tested in the box for a period of 30 minutes.

Traumatic Brain Injury

Ten-week-old male C57/BL6 (wild-type [WT]) mice of similar size (mean [SD], 28.7±1.9 g) were obtained from Jackson Laboratories (Bar Harbor, Me.). Before injury, all mice were lightly anesthetized for 5 minutes using 2% isoflurane, the left frontoparietal area was shaved, and the mouse placed in a stereotaxic frame. Injury directly to the left frontoparietal skull was delivered using the Impact One Stereotaxic Impactor (MyNeuroLab, St. Louis, Mo.) for closed cortical impact with the following settings: 2-mm piston tip, 3-m/s impact velocity, 30-millisecond dwell time, and 3-mm impact depth. Sham mice were similarly placed into the stereotaxic frame for 5 minutes under anesthesia. Mice were recovered on a warmed pad and time to movement from supine to prone recorded. Statistical analysis Quantification and stereological counting procedure for cell numbers or area ($\mu m^2$) of Amyloid beta plaque, GFAP$^+$, Iba1$^+$ or Perforin1$^+$ cells were analyzed from six to eight coronal sections from each individual, at 150-μm intervals (unless otherwise indicated), covering 900-1200 μm of the hippocampal and cortical areas. Specific signal fluorescence was captured with the same exposure time for each image and optical sections from each field of the specimen were imported into the NIH Image J software and analyzed as above. Statistical analysis GraphPad Prism software (version 5.0b; San Diego, Calif., USA) was used to analyze the data using ANOVA and T-Tests with Welch's correction (no assumption of equal variance). In histograms, average±SEM is depicted.

For human gene expression analysis, if multiple probesets existed per gene, those with the highest relative expression were chosen. Percentages were assigned a negative value if marker probeset expression in severe AD was less than marker probeset expression in control illustrates size, specificity, and expected staining pattern of lymphoid cells, as well as correlation with CD8α WB signal in human brain±mild AD pathology (r=0.8155, n=6, P=0.024, Pearson's correlation). Values presented are (marker probeset expression in AD/marker probeset expression in control)/(GFAP probeset expression in AD/GFAP probeset expression in control)×100. For PRF1 analysis, cortex:hippocampus ratios were 60:40 (normal) and 75:25 (mild and severe AD). Additional genes analysed in severe AD relative to normal aging brain were represented by the following probesets: $\beta_2 m$ (216231_s_at), GAPDH (212581_x_at), β-actin (213867_x_at), β-tubulin (211714_x_at), IFNγ (210354_at), and CD107a (201553_s_at).

Power analyses were performed for each metric using PBS and wt-CD8 groups for effect size, to determine PrfKO-CD8 and IfnγKO-CD8 group sizes sufficient to detect differences observed between with >95 confidence, and group sizes with at least one individual beyond that minimum were analyzed. Pre-determined exclusions included sections or samples with no discernible control staining or signal, and values within each group that exceeded 2 standard deviations above or below the average of that same group. Subject numbers and methods of reagent validation are shown in Table 3.

TABLE 3

Group numbers and validation. Validation: WB = Western blot; morph = expected morphology obtained on tissue staining; WB(absorb) = expected positive signal by Western blot with negative antigen-absorbed control; huAD = additional expected morphology obtained on brain tissue from human AD patients; co-staining = stained with 2$^{nd}$ cell-type-specific reagent, (anti-CD8 antibody).

| HOST | ANALYSIS | Brain Region/Method | PBS | wt-CD8 | PrfKO-CD8 | IfnγKO-CD8 | VALIDATION |
|---|---|---|---|---|---|---|---|
| B6.Foxn1 | CD8 | Cortex | 10 | 11 | 9 | 6 | WB, IHC morphology |
| | | Hippo | 11 | 12 | 3 | 6 | |
| | GFAP | Cortex | 10 | 19 | 10 | 6 | WB, IHC morphology |
| | | Hippo | 9 | 14 | 7 | 6 | |
| | Iba1 | Cortex | 3 | 5 | 3 | 5 | IHC morphology |
| | | Hippo | 4 | 4 | 3 | 3 | |
| | Aβ (10 wk) | 1-40 | 4 | 9 | NA | NA | NA |
| | | 1-42 | 4 | 9 | NA | NA | |
| | Aβ (15 mos) | 1-40 | 4 | 7 | 3 | 3 | |
| | | 1-42 | 8 | 14 | 6 | 6 | |
| | 4G8 IHC | Cng ctx | 7 | 11 | 6 | 8 | WB (absorbed), IHC |
| | | Hippo | 6 | 11 | 5 | 8 | morphology, huAD IHC |
| | | Ent ctx | 4 | 10 | 6 | 8 | |
| | pTau/PHF | 10 wk | 7 | 11 | NA | NA | WB, IHC |
| | | 15 mos | 4 | 7 | 6 | 5 | morphology, huAD IHC |
| | Gallyas | Cng ctx | 7 | 15 | 5 | 9 | IHC morphology, |
| | | Hippo | 7 | 13 | 6 | 19 | huAD IHC |
| | | Ent ctx | 19 | 19 | 5 | 10 | |
| | NeuN | WB | 8 | 8 | 6 | 6 | WB, IHC morphology |
| | | counts | 4 | 6 | 3 | 3 | |

TABLE 3-continued

Group numbers and validation. Validation: WB = Western blot; morph = expected morphology obtained on tissue staining; WB(absorb) = expected positive signal by Western blot with negative antigen-absorbed control; huAD = additional expected morphology obtained on brain tissue from human AD patients; co-staining = stained with 2$^{nd}$ cell-type-specific reagent, (anti-CD8 antibody).

|  |  |  |  |  |  |  |  |
|---|---|---|---|---|---|---|---|
|  | Drebrin WB | forebrain | 4 | 4 | 3 | 3 | WB, IHC morphology |
|  | Brain wt | 6 mos | 5 | 5 | NA | NA | NA |
|  |  | 15 mos | 4 | 8 | 7 | 7 |  |
|  | Open Field | 3 mos | 10 | 21 | 10 | 10 |  |
|  |  | 6 mos | 10 | 15 | 10 | 10 |  |
|  |  | 13 mos | 7 | 10 | 10 | 10 |  |
|  | Fear Cond | 6 mos | 8 | 11 | NA | NA |  |
|  |  | 11 mos | 16 | 15 | NA | NA |  |
|  | Spont Alt | 12 mos | 7 | 17 | 10 | 10 |  |
|  | Barnes Maze |  | 14 | 12 | 10 | 9 |  |

|  |  | sham | hiT | TBI | hiT + TBI |  |
|---|---|---|---|---|---|---|
| C57BL/6 | Aβ40 (10 wk) | 8 | 5 | 5 | 9 | NA |
|  | pTau/PHF | 8 | 5 | 5 | 9 | WB, IHC morph, huAD IHC |
|  | NeuN | 8 | 5 | 5 | 9 | WB, IHC morph, |

|  |  | normal | mild AD | severe AD |  |
|---|---|---|---|---|---|
| Human | microarray | 9 | 13 | 7 | GFAP normalization |
|  | Prf1 protein | 5 | 4 | 10 | WB, huAD IHC |
|  | pHLA/APP + anti-CD8 | 10 | NA | 10 | IHC morph, co-staining |

Example 2. Generation of "hiT" Cells in Nude Mice

Figure 1A:
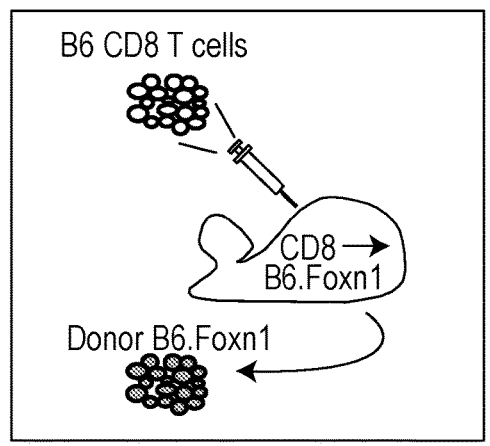
FIG. 1 depicts in accordance with various embodiments of the invention, expansion of donor cells in B6.Foxn1 mice deficient for Amyloid Precursor Protein (App). Purified CD8 T cells from female C57BL/6 or congenic knockout hosts were injected into 8-10 week-old female B6.Foxn1, B6.Foxn1-AppKO, or B6.CD45.1-congenic recipients (A). Blood was analyzed by flow cytometry 3 days later using the gating and antibodies to T cell markers as shown (B), with % CD3ε$^+$CD8$^+$ in gated cells compiled in (C). B6.Foxn1 mice were crossed to B6.App-knockout mice, homozygous double-mutants (B6.Foxn1-AppKO) verified by PCR and phenotype at Jackson Laboratories (Bar Harbor, M N), and CD8 T cells expansion assessed by CFSE dilution in B6.Foxn1 and B6.Foxn1-AppKO female recipients (D; n=3 B6.Foxn1 & n=5 B6.Foxn1-AppKO; *P<0.04, ***P<0.00001 by 2-tailed T-test in 3 independent trials; n≥5 mice/group in ≥3 independent tests for all markers).
Figure 1B:
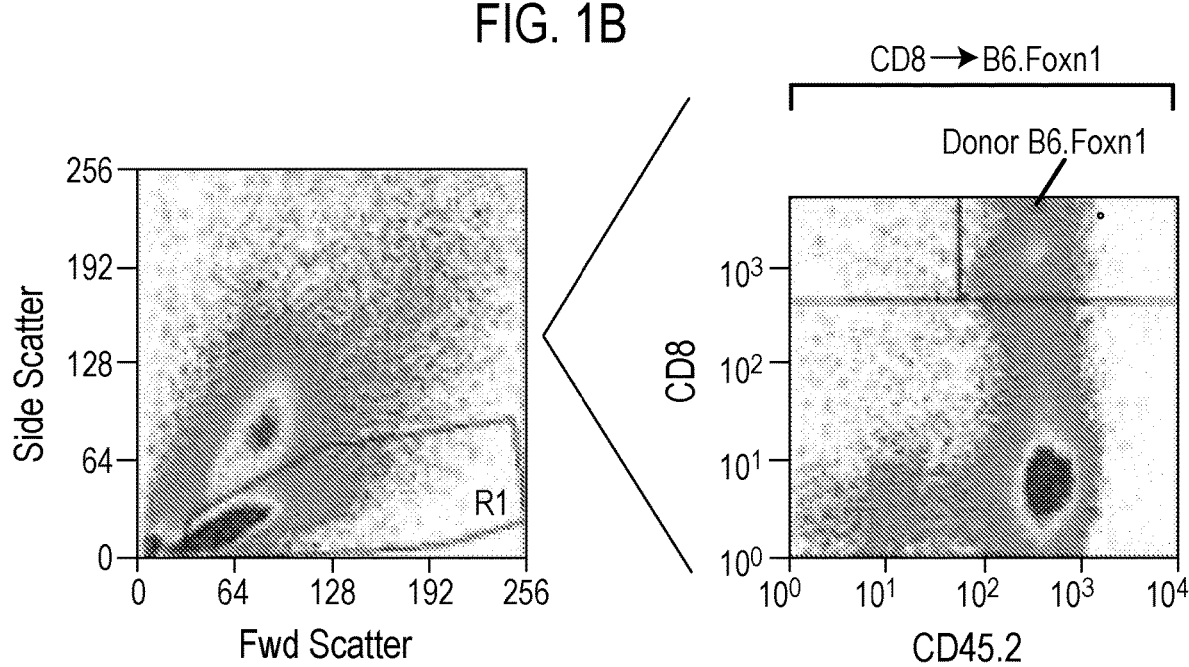
Figure 1C:
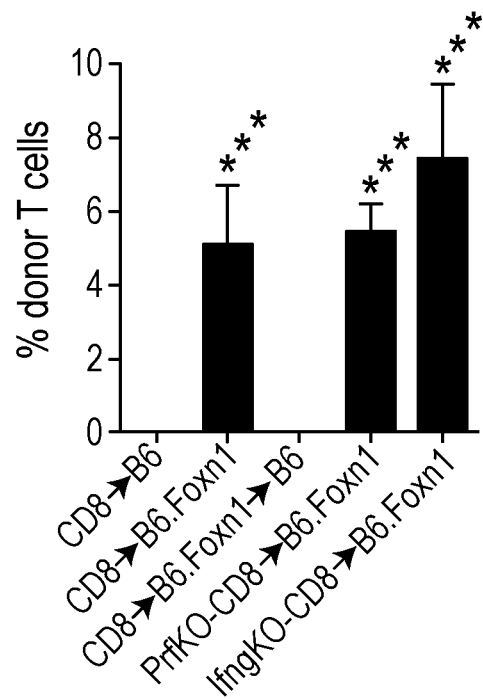
Figure 1D:
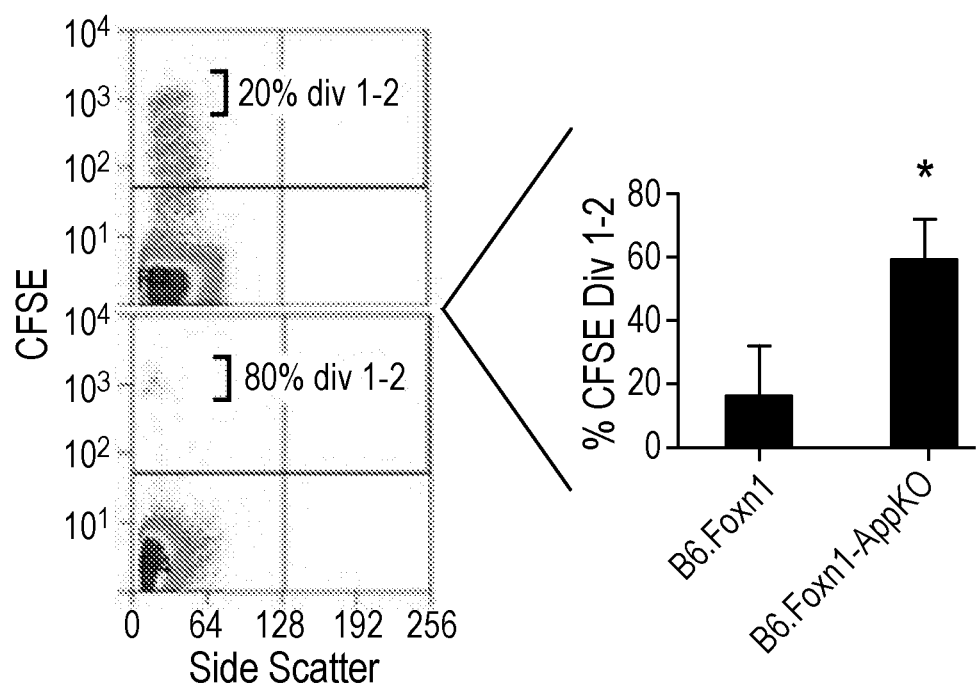
Figure 2A:
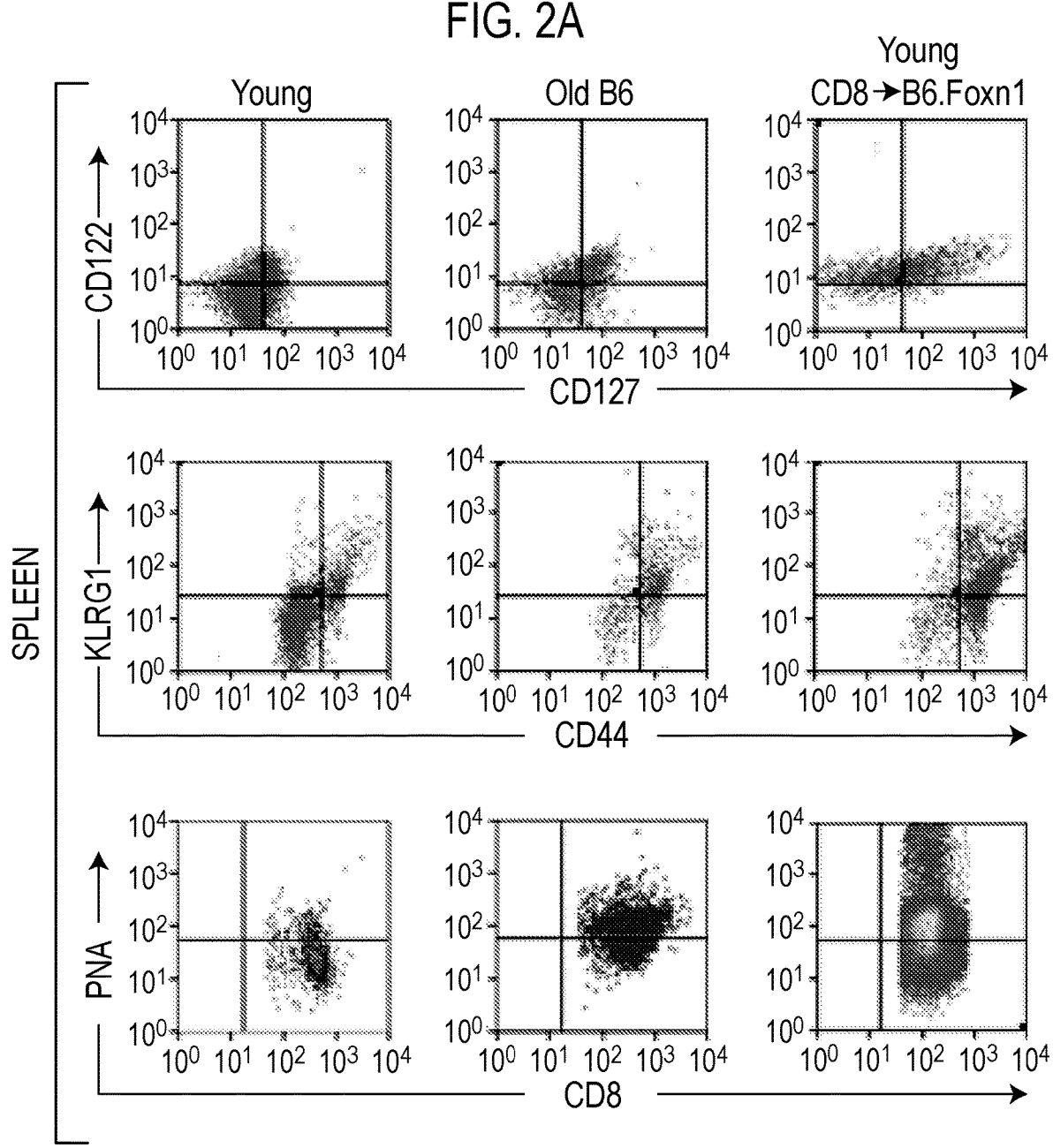
FIG. 2 depicts in accordance with various embodiments of the invention, age-related hiT cell phenotype in young mice. Representative flow cytometry analysis of age-related markers on splenic CD8 T cells from young (<10 weeks) and old (>12 months) C57BL/6 (B6), and young (6 weeks) B6.Foxn1 recipients of i.v. CD8 T cells (CD8→B6.Foxn1) 3-5 weeks after injection (A). Percentage of lymphocytes (B) and mean fluorescence intensity (C, D) from flow cytometry compiled from n≥6 mice/group. Proportions of mice with "diverse" TCRVβ D→J gene segment usage (>3 segments/brain) and specific D→J segments within brains of young (<10 weeks), middle-aged (6 months), and old (>12 months) B6 mice, reveals an age-dependent pattern of progressively decreased diversity and increased usage of particular D→J segments (i.e., clonality; E, F). D→J diversity and segment usage was significantly correlated only between old B6 and young CD8→B6.Foxn1 brain (G). *P<0.05, P<0.01, *P<0.005 by 2-sided T-test n≥5 mice/group in ≥3 independent tests for flow cytometric markers, and by Pearson's correlations in n≥10 mice/group for PCR compilations
Figure 2B:
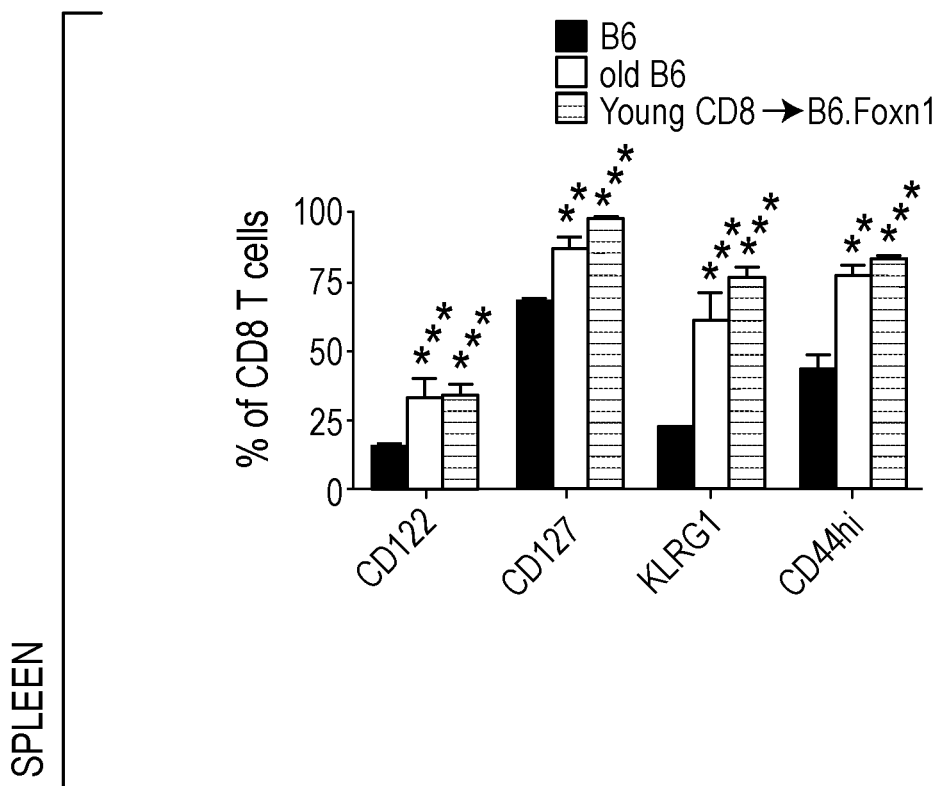
Figure 2C:
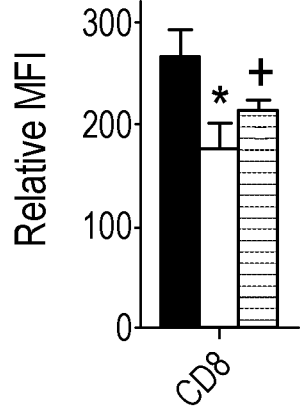
Figure 2D:
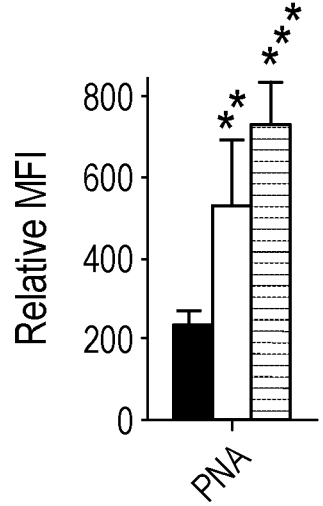

CD8 T cells from C57BL/B6 (B6) donors were injected into B6.CD45.2-congenic [B6$^{(Cg)}$] or B6.Foxn1 recipients, and were either retained in these mice, or serially transferred into secondary wild-type recipients prior to phenotypic analysis (FIG. 1A, 1B; FIG. 2A). Donor CD8 T cells rapidly expanded in blood of young B6.Foxn1 recipients within 3 days, where they remained long-term (FIG. 1C, 1D). CD8 T cells serially transferred from nude into wild-type B6 or B6.CD45.2-congenic [B6$^{(Cg)}$] hosts did not expand further (FIG. 1B, 1C). Analysis of donor CD8 T cell expansions (hiT cells) in B6.Foxn1 hosts, as well as pre-expanded hiT cells serially injected from nude into B6.CD45.2-congenic hosts, revealed generally equal or greater modulation of signature surface markers of aged CD8 T cells (CD122$^{hi}$, CD127$^{hi}$, CD44$^{hi}$, KLRG1$^{hi}$, PNA$^{hi}$, CD8$^{lo}$; FIG. 2A-2D) (6, 18-20). A similar phenotype is found on CD8 T cell clonal expansions in aging humans (6). Donor CD8 T cells from B6 Interferon-gamma(Ifnγ)-deficient, or Perforin1-deficient donors all expanded comparably in B6.Foxn1 recipients (FIG. 1C), consistent with previous studies (21). Accordingly, CF SE-labeled CD8 T cells exhibited the laddered dye dilution and population enlargement typical of rapid homeostatic expansion (FIG. 1D). This did not, however, occur in nude mice lacking the Amyloid Precursor Protein (App) gene (B6.Foxn1×AppKO mice; FIG. 1D), suggesting that rapid homeostatic expansion was dependent on reactivity to APP.

Figure 2E:
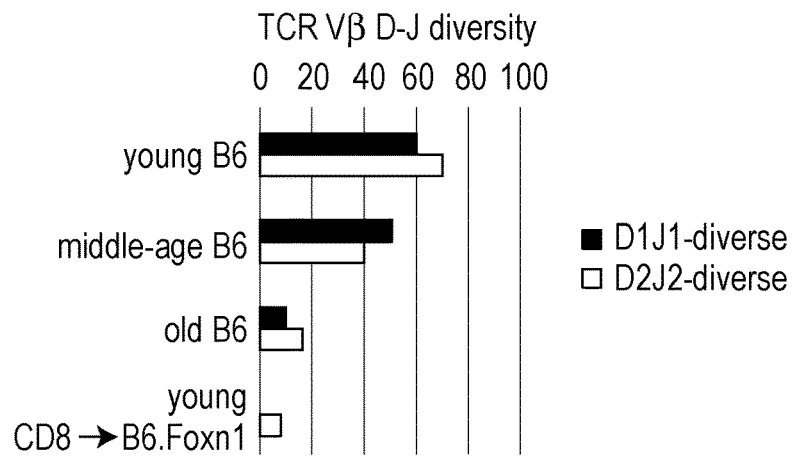
Figure 2F:
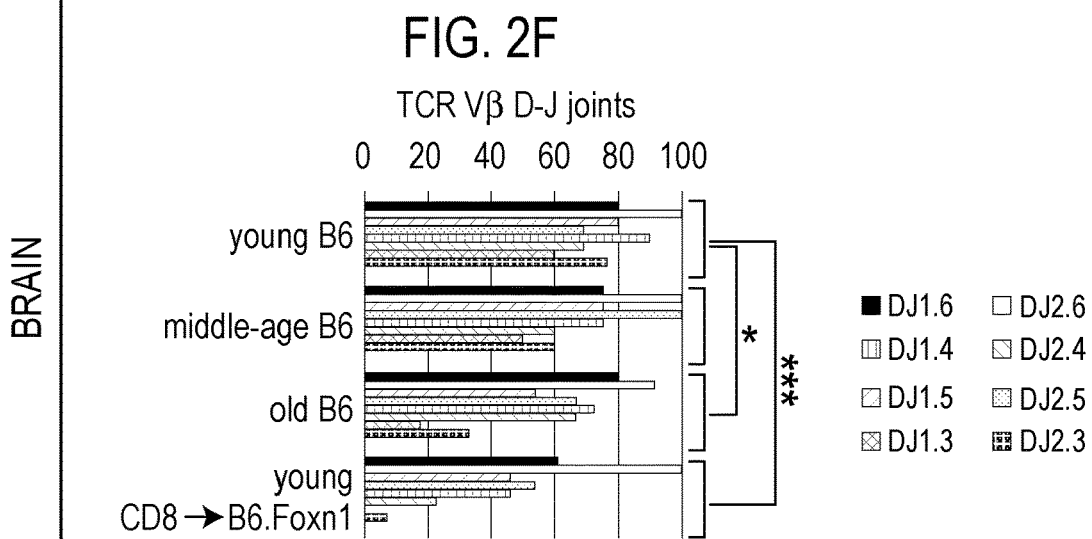
Figure 2G:
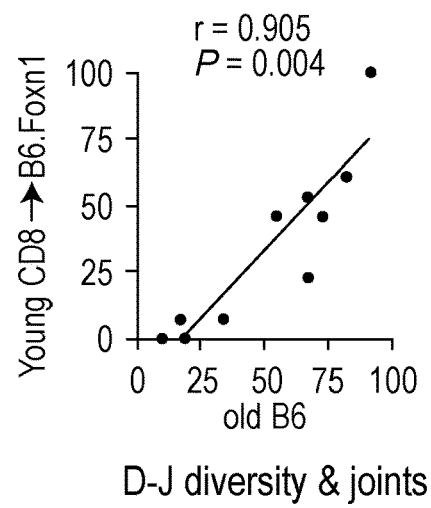
Figure 3A:
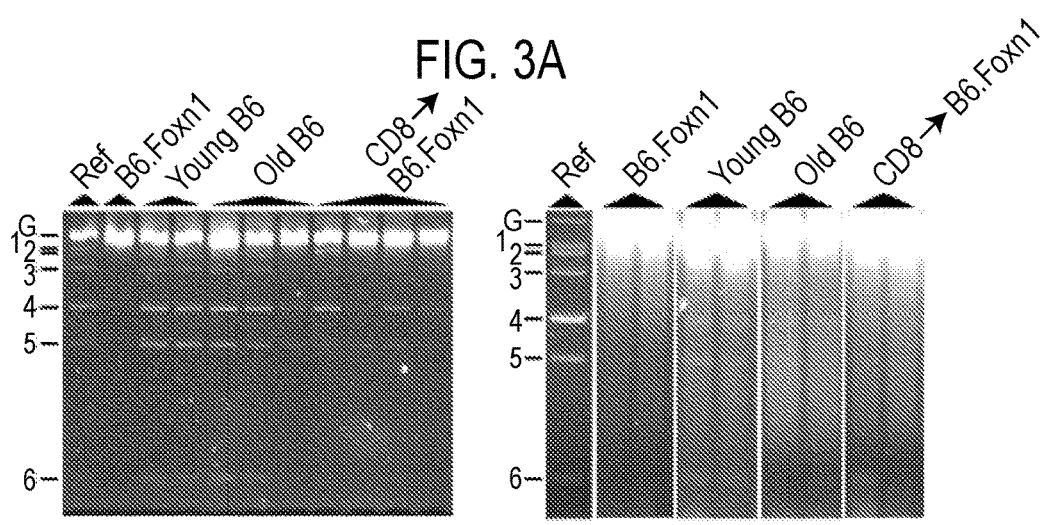
FIG. 3 depicts in accordance with various embodiments of the invention, PCR and Western analysis of T cell and amyloid markers. PCR for TCRVβ D1→J1 (A) and D2→J2 (B) gene segments indicated full diverse T cell repertoires in young and old C57BL/6 (B6), but restricted TCRVβ diversity in B6.Foxn1 recipients of CD8 T cells after 10 weeks (CD8→B6.Foxn1). B6.Foxn1 mice lacked rearranged TCR products in brain unless wt-CD8 T cells were injected 10 weeks prior (C); TCRVβ D2 analysis is shown; D1 analysis exhibited very similar results). TCRVβ gene products in B6.Foxn1+CD8 mice shown involve D2J2.1, D2J2.2, and/or D2J2.4 rearrangements preferentially. Western blot of CD8α (53-6.72 clone) in dissected brain hippocampus of young (<5 months) C57BL6 (B6) and B6.Foxn1 hosts with and without adoptive transfer of CD8 T cells from young (6-8 wk) B6 donors 10 weeks prior (D). CD8 protein is detectable at very low levels in B6, but is undetectable in B6.Foxn1 unless wt-CD8 T cells were injected 10 weeks before. "Ref"=6-10 week-old female C57BL/6 spleen DNA or cell lysate, subjected to identical analysis.
Figure 3B:
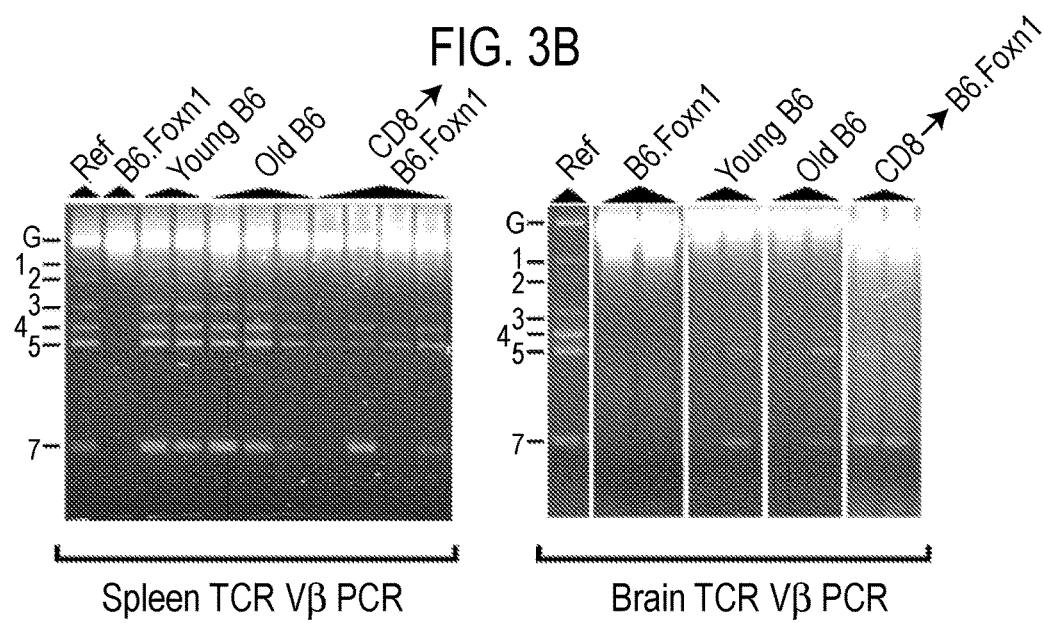
Figure 3C:
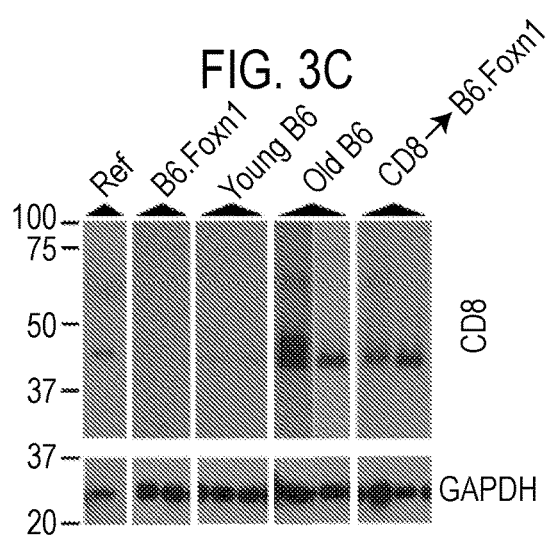
Figure 3D:
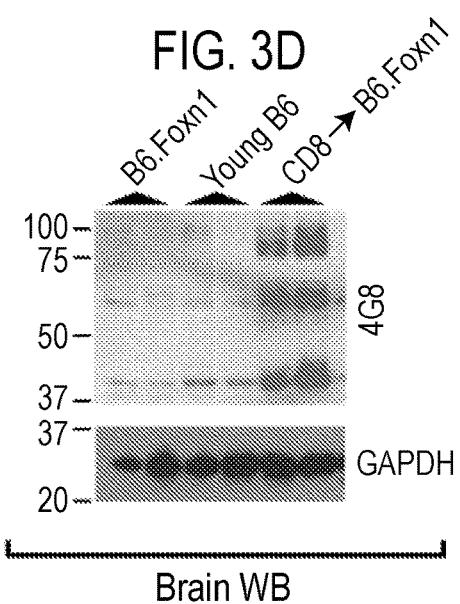

To further verify clonality of hiT cells in mice, we examined variable region D→J gene rearrangement products of T Cell Receptor beta (TCRVβ) by PCR. Consistent with previous reports, peripheral T cells in wild-type mice aged 12 months showed no evidence of clonal skewing in TCRVβ, but those injected into nude recipients exhibited oligoclonality in both D1→J1 and D2→J2 products after just 10 weeks (FIG. 1A, 1B). Importantly, TCRVβ rearrangement products with reduced diversity and oligoclonal D→J usage were also evident in brains of young nude mice injected with CD8 T cells, in contrast to the diverse, nonclonal pattern seen in young wild-type mice (FIG. 2E, 2F; FIG. 1A, 1B). This pattern was progressively age-dependent, and significantly different from that in young wild-type mice, most closely resembling the pattern in brains of old-aged mice (FIG. 1E-G). CD8 T cell injection also specifically increased CD8 and 4G8 (App/Aβ) protein reactivity in B6.Foxn1 brain (FIG. 3C, 3D). Thus, injection into nude hosts induced peripheral expansion of clonal CD8 T cells with a unique memory phenotype, as commonly occurs in aging humans. These T cells exhibit the same oligoclonality in brain as in aged hosts, suggesting the generation of a discrete age-related immune cell subpopulation impacting App/Aβ in otherwise young mice.

Figure 4A:
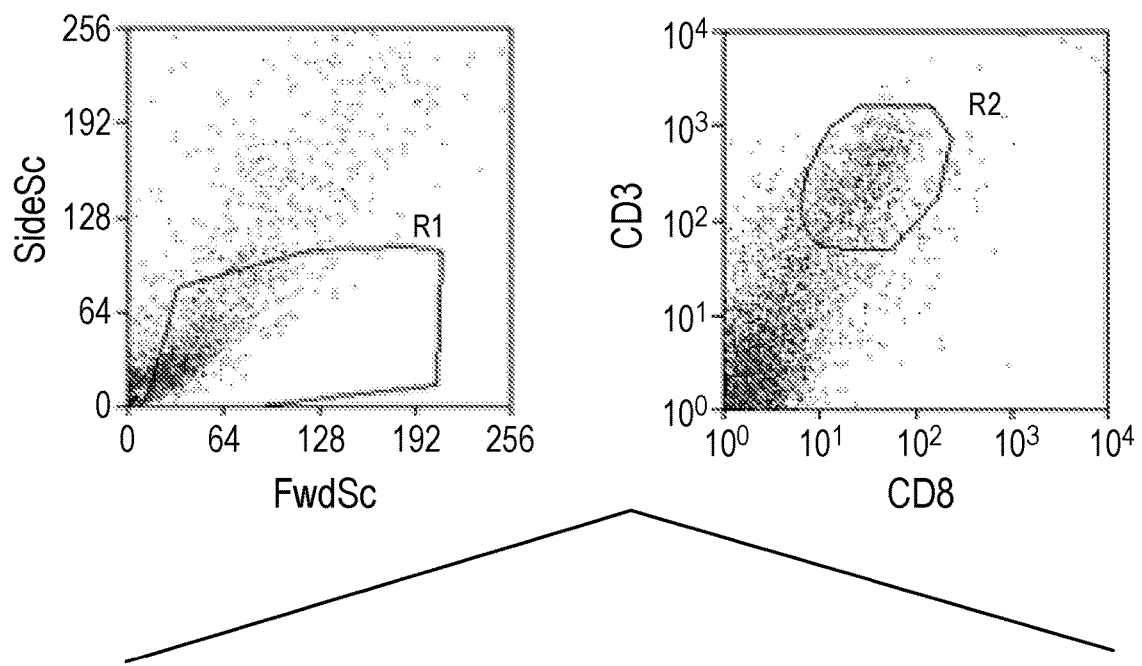
FIG. 4 depicts in accordance with various embodiments of the invention, brain CD8 T cell phenotype after transfer into nude mice. Light scatter and gating of brain lymphocytes and CD8 T cells in B6.Foxn1 recipients (A). Percentage and phenotype of CFSE$^+$CD8 T cells within brain lymphocytes in B6.Foxn1 recipients 3 days (B), and 10 weeks (C) after injection. Increased staining with pMHC I multimers (custom dextramers synthesized by Immudex USA, Fairfax, Va.) to Trp-2-DCT$_{(180-188)}$/H-2K$^b$ and APP$_{(470-478)}$/H-2D$^b$ epitopes on KLRG1$^+$CD8 T cells in B6.Foxn1 brain (D, E) and spleen (E), 10 weeks after injection (*P<0.05 by 2-sided T-test in ≥3 independent tests; n≥6 for all analyses, with significance relative to PBS group)
Figure 4B:
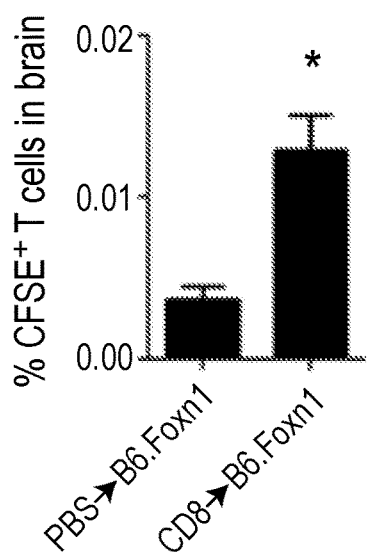
Figure 4C:
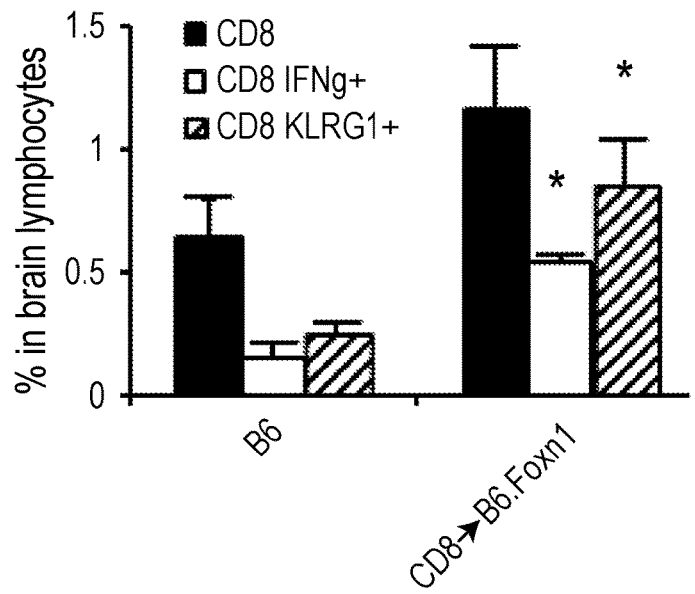
Figure 4D:
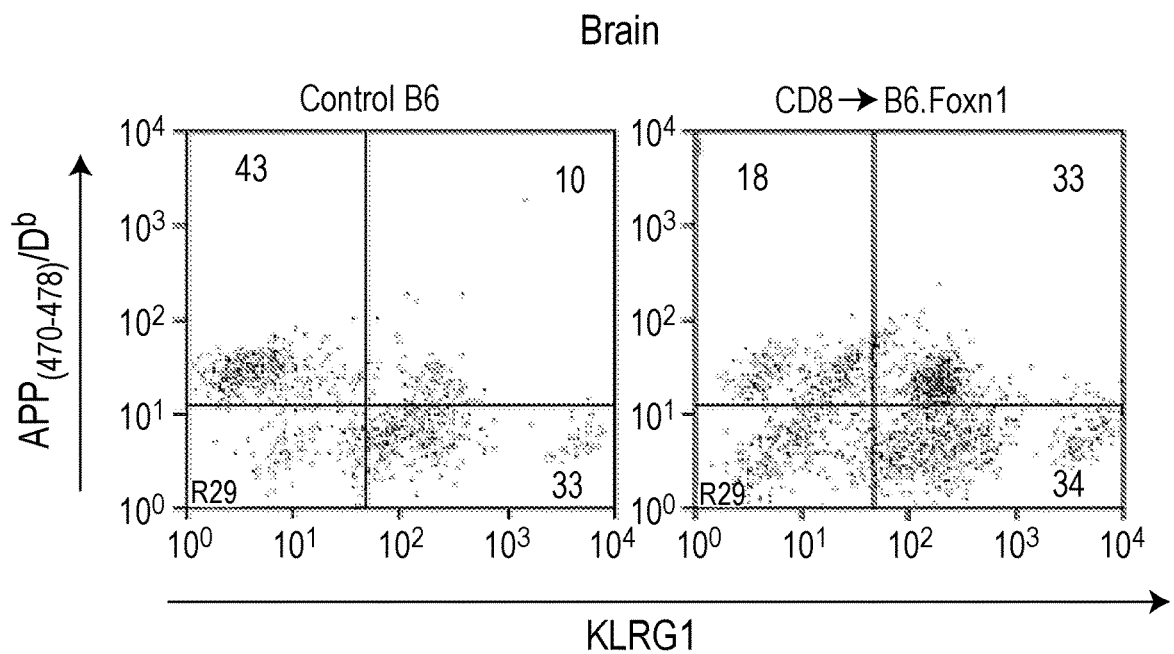
Figure 4E:
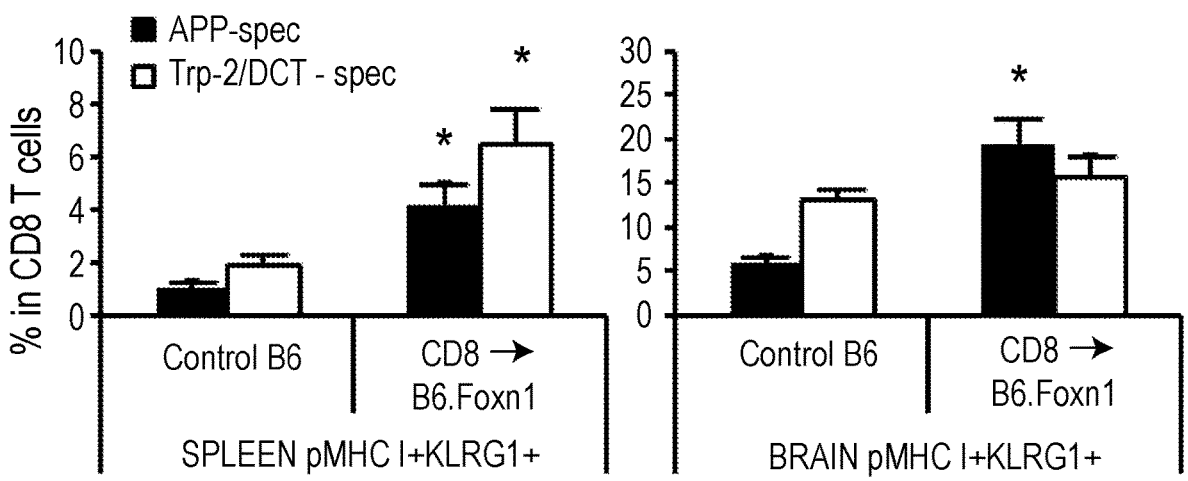

Directly confirming homing of hiT cells to brain, CFSE-labeled donor CD8 T cells were increased in B6.Foxn1 hosts three days after i.v. injection (FIG. 4A, 4B). Although total CD8 T cells in brain were only marginally increased over those in wild-type B6 brain, IFNγ$^+$ and/or KLRG1$^+$CD8 T cells were significantly increased in young hiT-bearing nude brains (FIG. 4C). Moreover, KLRG1$^+$CD8 T cells in peripheral blood were reactive to multiple MEW I-restricted antigens, including Tyrosinase-related Protein-2/Dopachrome Tautamerase (Trp-2/DCT) and APP, but only the latter were significantly increased in brain (FIG. 4D, 4E). This confirmed hiT cell reactivity to APP and accumulation in brain, and led us to examine APP cleavage products in nude mice harboring hiT cells, as depicted in FIG. 6A.

Example 3. Aβ and Neurofibrillary Deposition

Figure 5A:
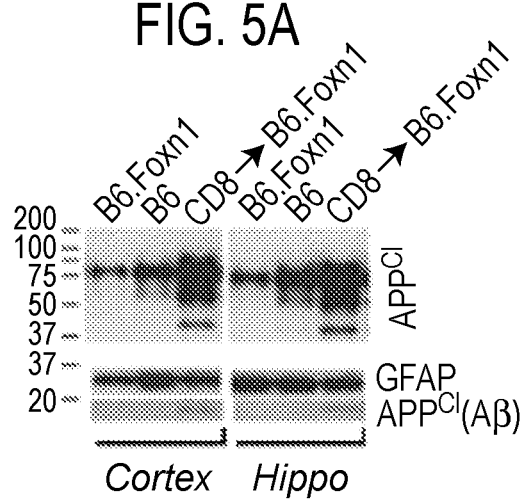
FIG. 5 depicts in accordance with various embodiments of the invention, Aβ plaque and neurofibrillar pathology in nude mice harboring hiT cells. Westerns of detergent-soluble APP cleavage products (APP$^{Cl}$) in dissected cortex and hippocampus 3 wk after control or cell injection (→) in indicated recipients (A). Cell/control recipients in panels B-J are B6.Foxn1 exclusively, with time after injection at 15 mos unless otherwise indicated. Forebrain ELISA of Triton-soluble Aβ1-40/42 (B). Parenchymal plaques with and without pTau or curcumin counter-staining (C), and compiled 4G8 burden (D) in entorhinal (Ent) and cingulate (Cng) cortex, and hippocampus (Hippo) in indicated mouse groups. Forebrain Westerns (E), and compiled signal quantification (F), of detergent-soluble phospho-tau (pTau) and paired helical filaments (PHF). Silver-stained cells in brain, and in 18 month-old AD-transgenic (Tg2576) mice, with sequential pTau→Gallyas stains inset (G). Compiled proportions of Gallyas$^+$ neurons (H), astrocytes (Gfap$^+$), and microglia (Iba-1$^+$; I-J). *P<0.05, P<0.01, *P<0.005 by 2-sided T-test in ≥3 independent tests for all analyses, relative to PBS group
Figure 5B:
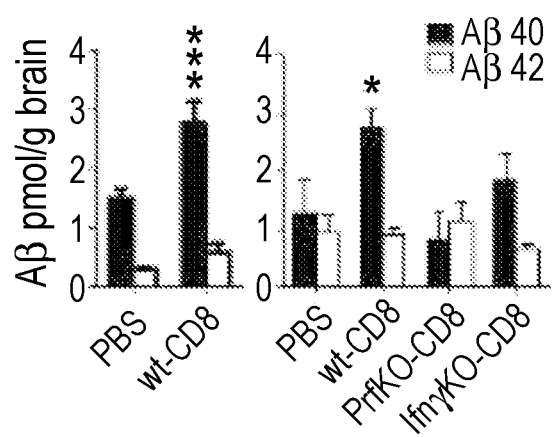
Figure 5C:
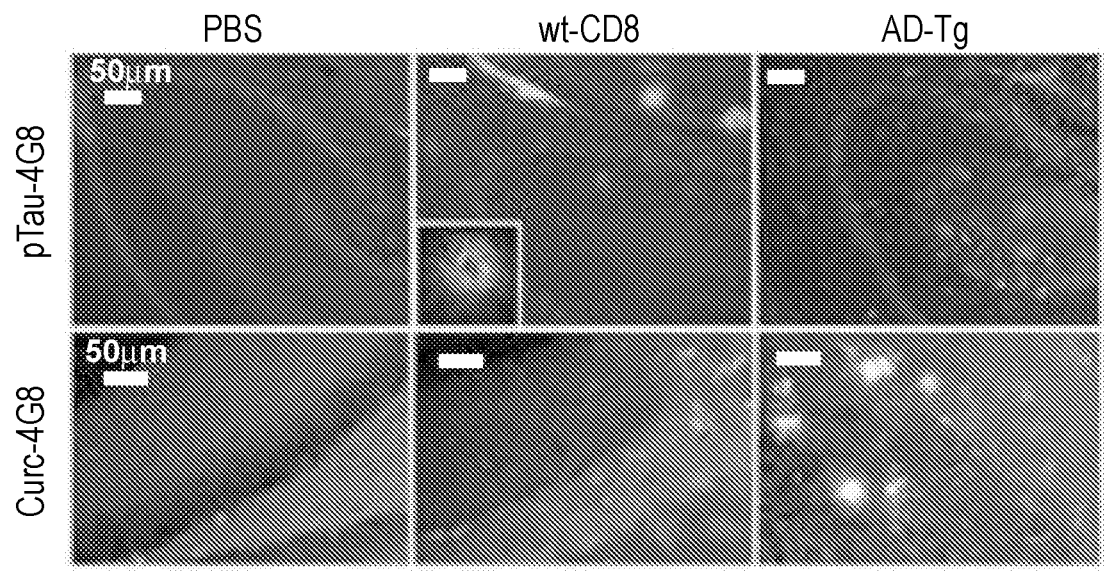
Figure 5D:
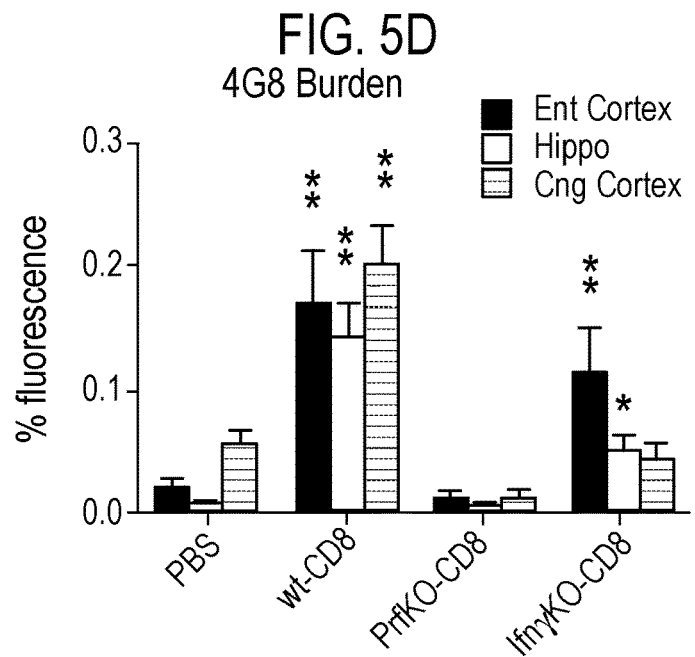
Figure 7A:
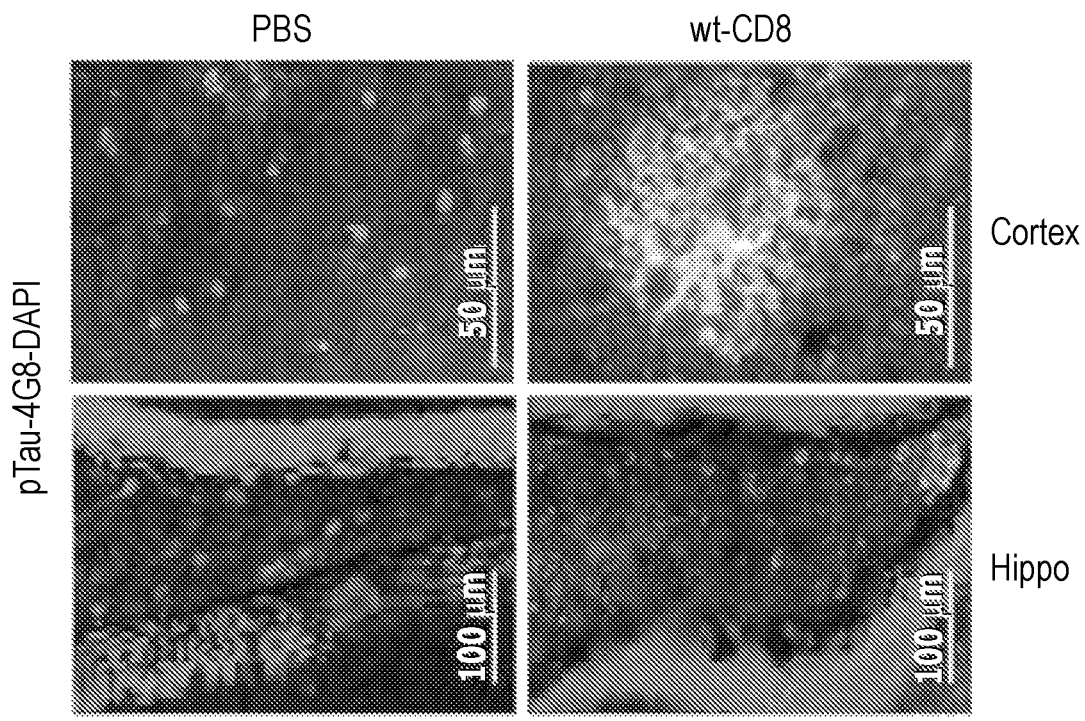
FIG. 7 depicts in accordance with various embodiments of the invention, Aβ accumulation in nude mouse brain after CD8 T cell injection. Representative example of individual Aβ (4G8$^+$) plaque morphology within entorhinal cortex and hippocampus in nude recipients 15 months after CD8 T cell injection. Magnification and image acquisition parameters were identical within each brain region (A). Forebrain ELISA of Guanidium-HCl-soluble Aβ1-40, in B6.Foxn1 brain 15 months after CD8 T cell or control injection (B).
Figure 7B:
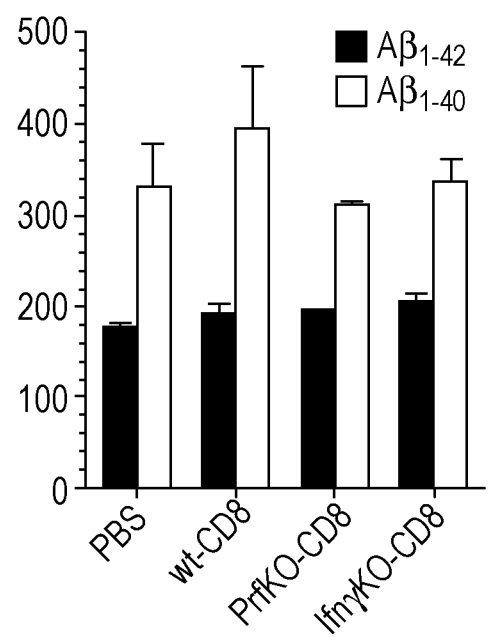

Detergent-soluble APP cleavage products (APP$^{Cl}$) were increased in dissected cortex and hippocampus of B6.Foxn1 hosts 3 weeks after i.v. CD8 T cell injection by Western blot (FIG. 5A). Aβ signal on Western blot (FIG. 3D) and Aβ1-40 on ELISA (FIG. 5B) was increased 2.5-15 months later as well and, with increased Aβ on vasculature observed at 6 months (FIG. 6B, C). Aβ plaques were detected in hippocampus, entorhinal cortex and cingulate cortex of B6.Foxn1 recipients injected with wild-type CD8 T cells (wt-CD8 group) 15 months later (FIG. 7A; FIG. 5C). By contrast, B6.Foxn1 recipients of Perforin1-deficient or Ifnγ-deficient CD8 T cells (PrfKO-CD8 and IfnγKO-CD8 groups, respectively), exhibited no increase in Aβ by ELISA at 15 months, and only the latter showed elevated plaques in hippocampus and entorhinal cortex (FIG. 5B, D; FIG. 7B). Plaques in wt-CD8 and IfnγKO-CD8 groups were mainly diffuse, with very little co-staining with curcumin or ThioS (FIG. 5C, FIG. 7B).

Figure 5E:
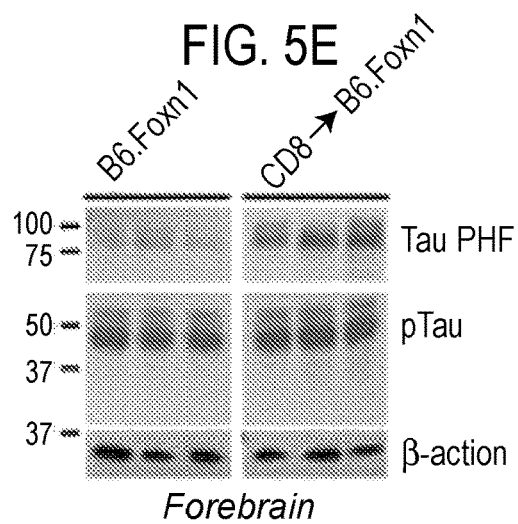
Figure 5F:
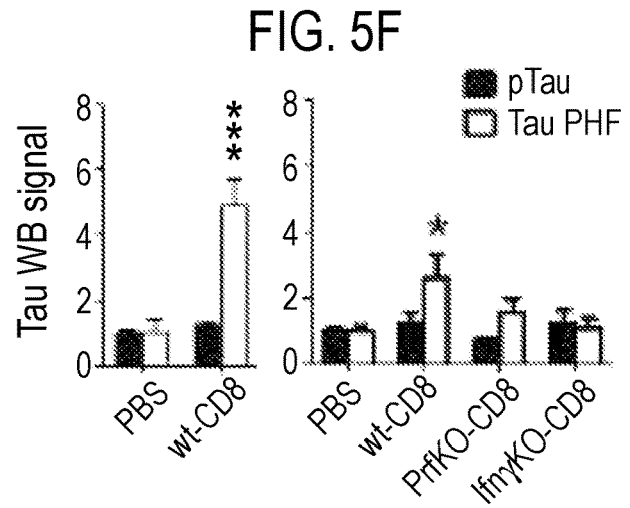
Figure 5G:
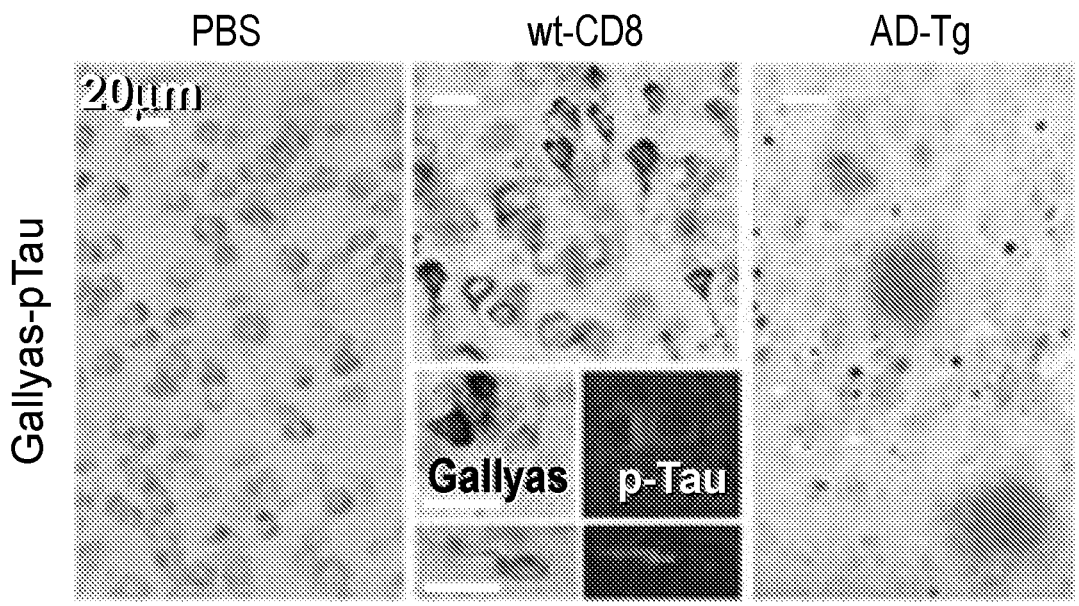
Figure 5H:
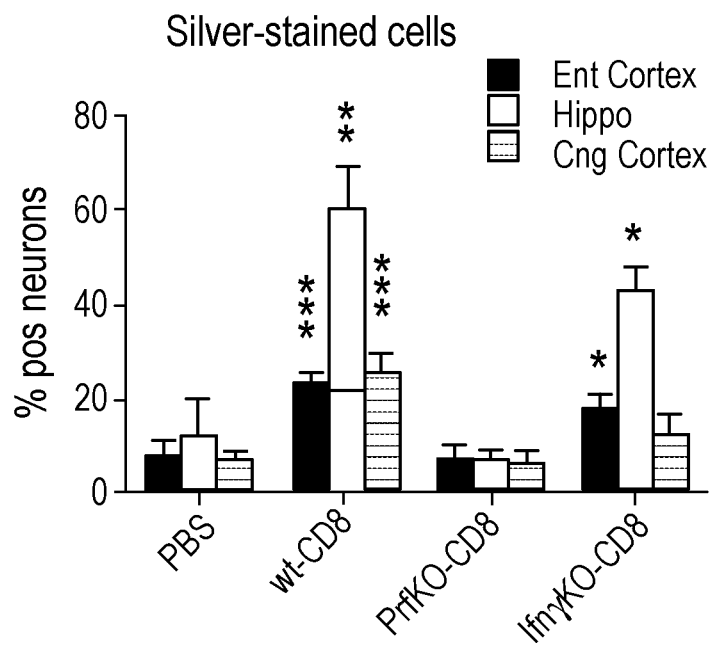
Figure 8A:
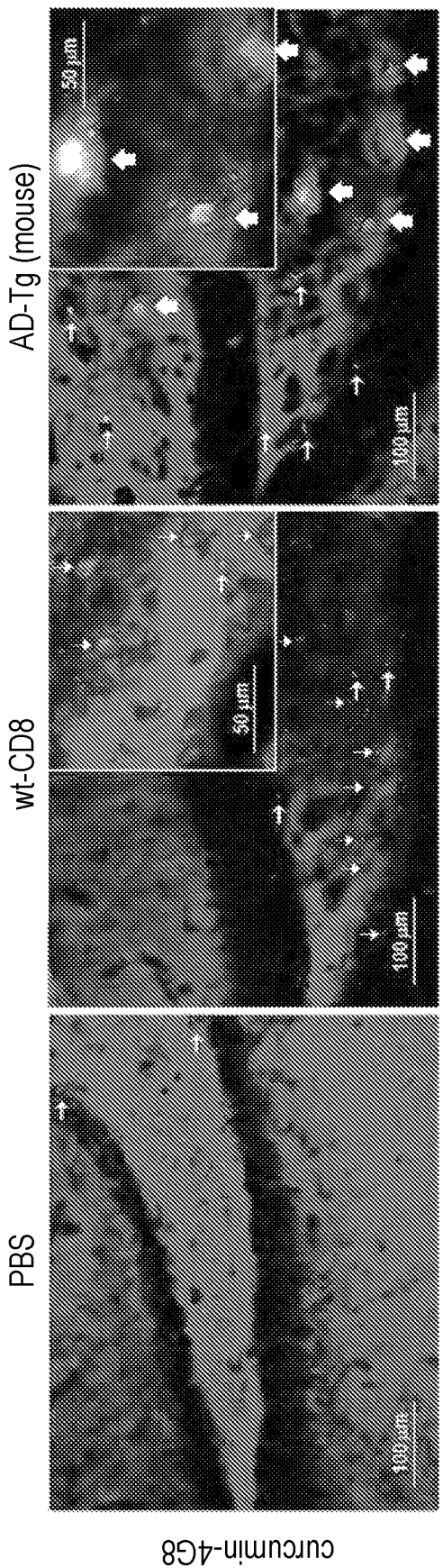
FIG. 8 depicts in accordance with various embodiments of the invention, distinct curcumin and ThioS staining in dentate gyrus of nude mice harboring hiT cells. a, Hippocampal sections from the indicated groups (all B6.Foxn1 recipients, except AD-Tg=Tg2576 mice), were stained for 4G8 (Aβ) and curcumin, 6 months after control/cell injection, or at 14 months of age for AD-Tg (A). Right arrows highlight Aβ deposits with no curcumin co-staining. Up-facing arrows depict co-localized Aβ and curcumin, representing densely fibrillar Aβ plaques. Down-facing arrows highlight curcumin$^+$ structures with no Aβ co-staining. No DAPI was used in the stains; blue channel background is provided for anatomical context only. Follow-up ThioS staining of PBS and wt-CD8 group B6.Foxn1 hiT recipients 6 months after control/cell injection, and 20 month-old AD-Tg rat dentate gyrus (B).
Figure 8B:
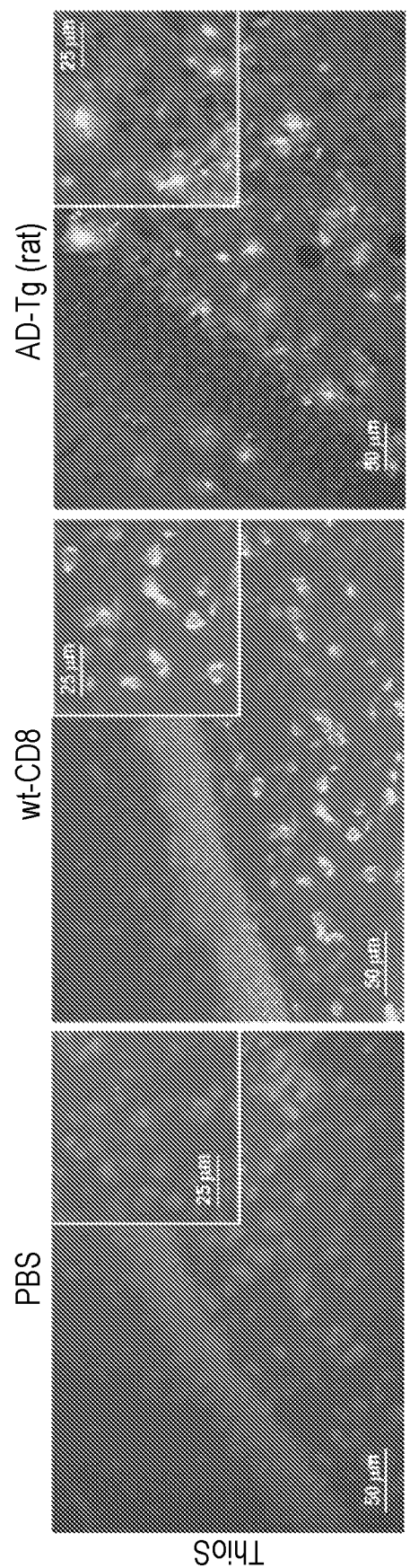
Figures 9A, 9B:
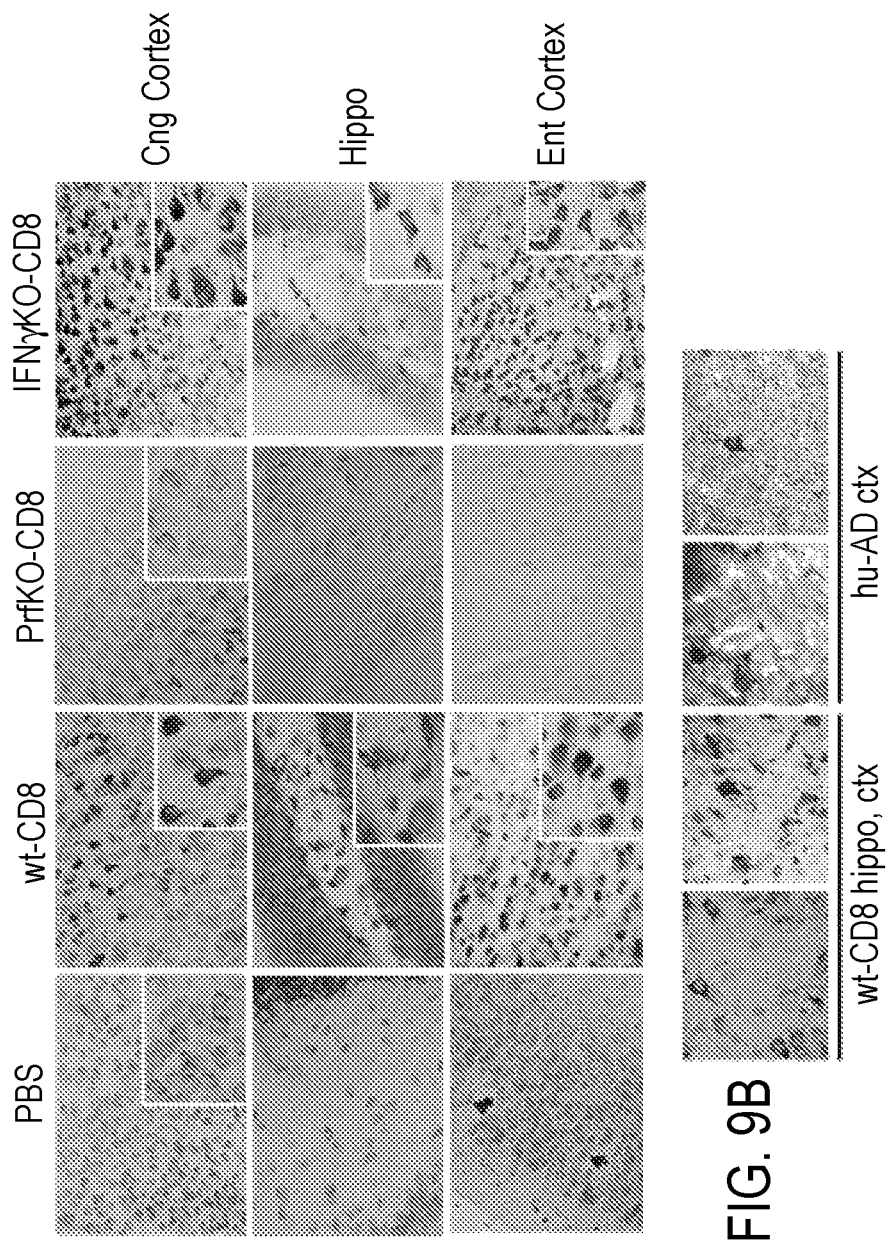
FIG. 9 depicts in accordance with various embodiments of the invention, silver stained neuronal structures in experimental groups. Gallyas silver staining of cortical and hippocampal brain regions, showing typical neurofibrillary tangle (NFT) morphology in wt-CD8 and IFNγKO-CD8 group mice (insets). Background silver staining was occasionally evident in PrfKO-CD8 or PBS group mice, but did not exhibit similar NFT morphology (insets). Individual images were derived from different mice within each group (n=3/group; A). Comparison of Gallyas$^+$ structures in nude mice harboring hiT cells (wt-CD8) hippocampus (left) and cortex (ctx, right), to those in cortex of human severe AD (Braak stage VI; B). Magnification and scale are identical for all images (20×), and among insets in A and B.

Aβ-negative, curcumin+ and ThioS+ cells were evident in dentate gyrus of wt-CD8 group mice 6 months after T cell injection (FIG. 8). Similar structures were not observed in aged AD-transgenic mice, or even in AD-transgenic rats that exhibit tau paired-helical filaments by electron microscopy (PHFs; FIG. 8)(22). This suggested that nude mice harboring hiT cells harbor non-amyloid fibrillar inclusions of hyper-phosphorylated tau protein (pTau), a feature not normally seen in AD-transgenic rodents. In support of this, Triton-soluble pTau, and especially the larger PHFs, were elevated in wt-CD8 relative to PBS group brains 10 weeks post-injection (FIG. 5E, 5F). The significant increase in detergent-soluble pTau was not sustained, whereas a somewhat muted PHF increase was (FIG. 5F). Most intriguingly, silver-stained cells were increased in hippocampus, entorhinal cortex, and cingulate cortex of wt-CD8 group; increased in hippocampus and entorhinal cortex of IfnγKO-CD8 group; and absent in all other groups (FIG. 5G, 5H). Sequential staining revealed that these structures arose from nucleated pTau+ neurons, with an absence of acellular "ghost tangles" as are typically seen in human AD (FIG. 5G; FIG. 9). Simultaneously stained AD-transgenic mouse brain exhibited prominent silver-stained plaques but not cells (Tg2576 mice; FIG. 5G), indicating their exclusive presence in hiT-bearing mouse brain. These data suggest that hiT cells promote the deposition of both parenchymal Aβ plaques and fibrillary inclusions in neurons.

Example 4. Immune and Neuroinflammatory Infiltration

Figure 5I:
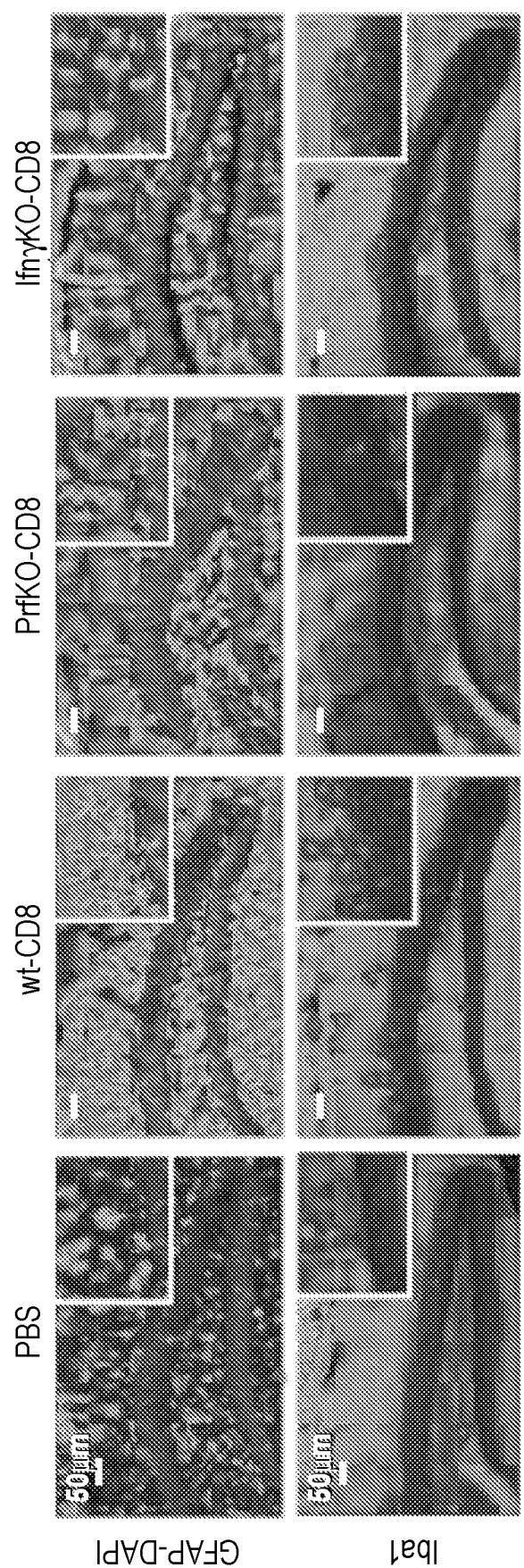
Figure 5J:
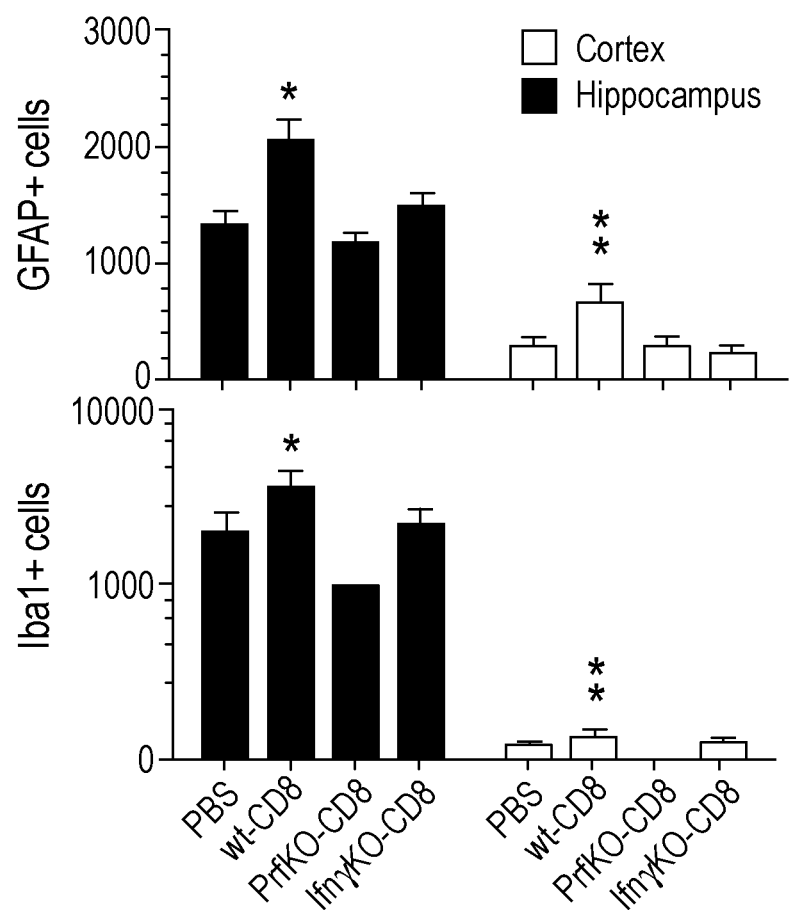
Figure 10A:
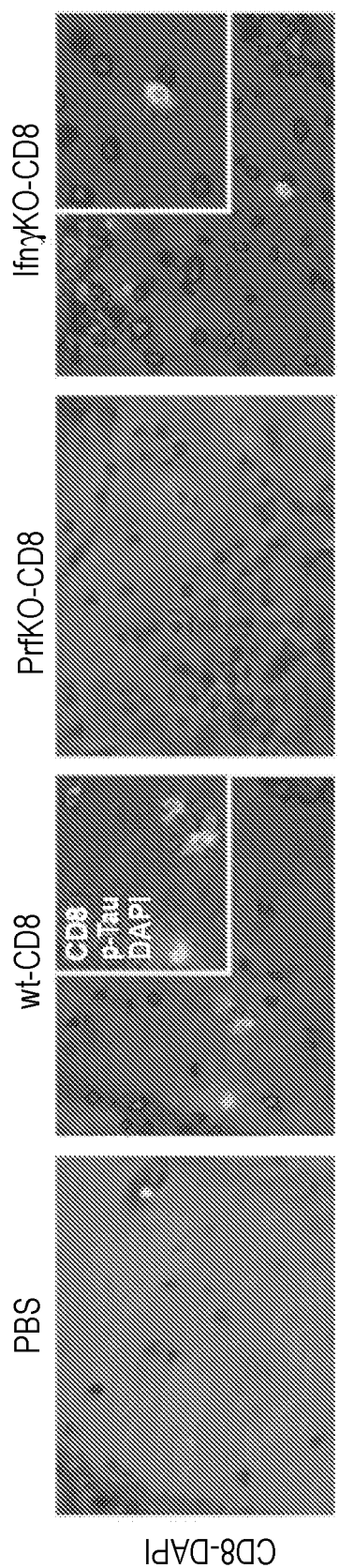
FIG. 10 depicts in accordance with various embodiments of the invention, T cells in brain tissue of nude mice harboring hiT cells. Brain was co-stained for CD8 and pTau (inset)(A), and quantified within hippocampal and cortical brain sections from B6.Foxn1 recipients 15 months after injection with wild-type, IFNγKO or PrfKO CD8 T cells, or with PBS (B). Astrocytic (GFAP), microglial (Iba-1), or CD8 T cell (CD8) areas significantly altered in FIG. 3 or Fig. S7 (**P<0.01, *P<0.05; 2-sided T-test. relative to PBS control) were then correlated with 4G8$^+$ plaque burden within each group, with r and P values from linear regressions and Pearson's correlations shown (C). Numbers of mice per group are listed in FIG. 12.
Figure 10B:
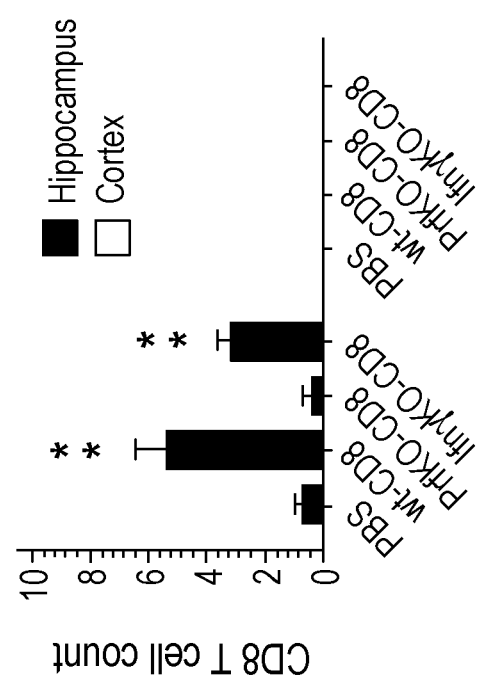
Figure 10C:
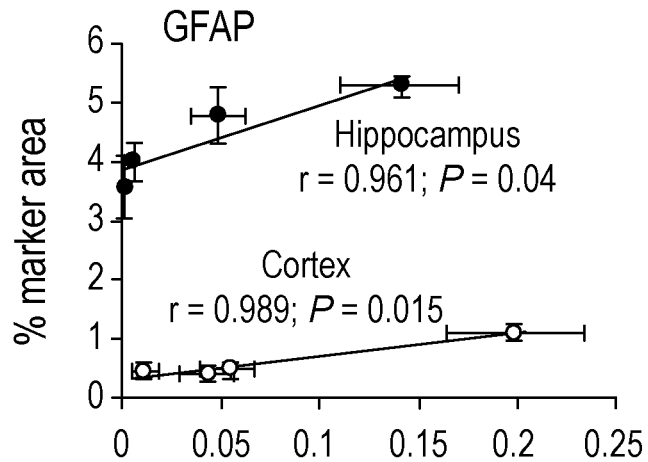
Figure 10C:
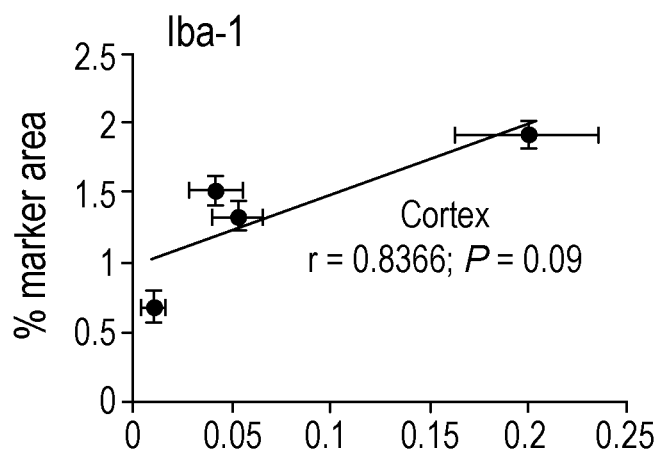
Figure 10C:
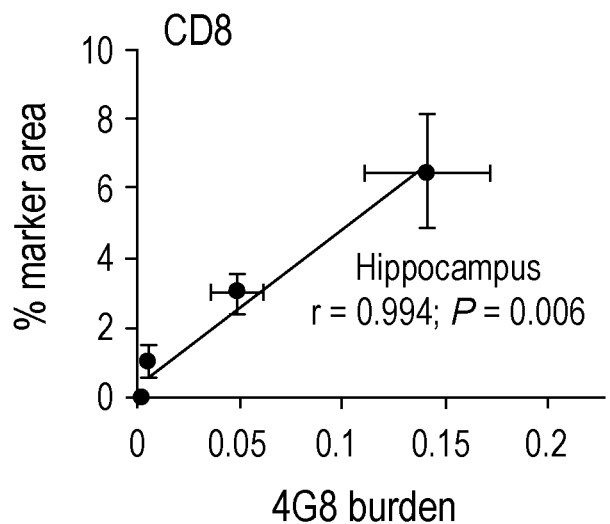

Although not apparent earlier by flow cytometry, CD8 T cell counts were significantly elevated in hippocampus of wt-CD8 and IfnγKO-CD8 groups 15 months after injection (FIG. 10A, 10B). CD8 T cell counts were not demonstrably elevated outside of hippocampus, a pattern of distribution reported in AD patients (10). Cortical and hippocampal Iba1+ microglia, and activated GFAP+ astrocytes, were also significantly elevated in the wt-CD8 group relative to all others (FIG. 5I, 5J). Thus, while wt-CD8 and IfnγKO-CD8 group mice exhibited similar CD8 T cell infiltration and proteinopathy, they differed in their extent of neuroinflammation. Aβ plaque burden correlated best with hippocampal CD8 T cell numbers, but was also significantly correlated with cortical and hippocampal astrogliosis (FIG. 10C).

Example 5. Neuronal Loss & Cerebral Atrophy

Figure 11F:
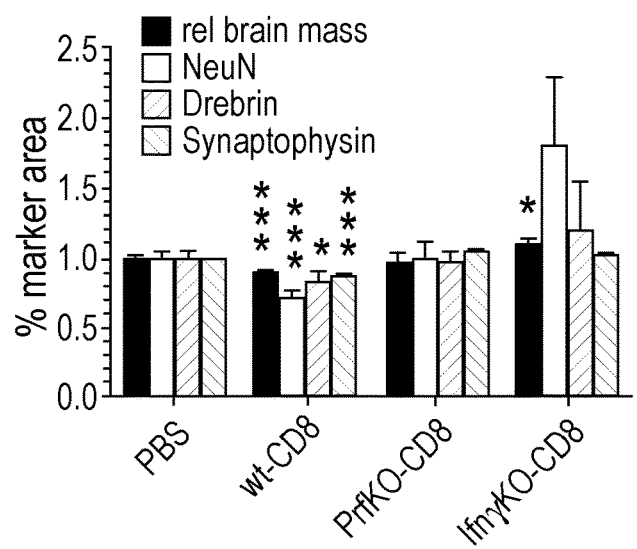
FIG. 11 depicts in accordance with various embodiments of the invention, neurodegenerative metrics and cognition in nude mice harboring hiT cells. Cell/control recipients in all panels are B6.Foxn1 exclusively. NeuN and GFAP staining (A, B), and cell counts in CA2, 15 mos after cell/control injection (C). Brain atrophy over time in PBS and wt-CD8 groups (mass normalized to PBS controls at each time point; D). Representative forebrain Westerns (E), and GAPDH-normalized NeuN, Drebrin, and Synaptophysin Western signals (F). Correlation of NeuN with brain weight (G). Representative Open Field test at 13 mos (H). Fear Conditioning performance over time (I), and Spontaneous Alternation (SA) at 12 months (J). Barnes Maze learning (K; P from 2-sided ANOVA), retention (L), and reversal (M, N) phases, at 14 mos (black, colored symbols=P relative to PBS, wt-CD8, respectively). *P<0.005, P<0.01, *P<0.05, +P<0.1 by 2-tailed T-test, except where other tests are indicated.
Figure 11G:
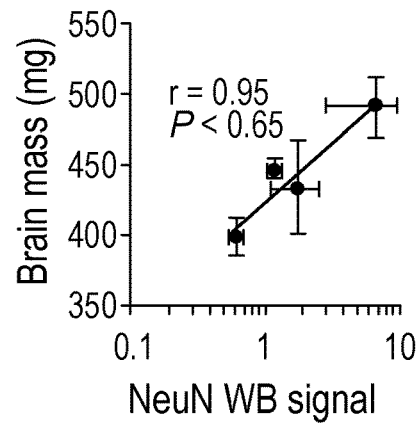

NeuN+ cell counts in hippocampus were decreased in wt-CD8 relative to PBS group brains 15 months after T cell injection (FIG. 11A-C). Moreover, brain mass was decreased 5% in wt-CD8 group mice 6 months after T cell injection, and 10% at 15 months (FIG. 11D). Significant neuronal and synaptic loss in the wt-CD8 group was confirmed by NeuN, Drebrin, and Synaptophysin Western blots, which each exhibited the same trend of a 10% decrease at 15 months (FIG. 11E, F). NeuN Western signal also correlated significantly with brain mass among treatment groups, suggesting that the observed brain atrophy was associated with neuronal loss (FIG. 11G). Curiously, the IfnγKO-CD8 group exhibited a surprising increase in brain mass and NeuN, without corresponding increases in synaptic markers (FIG. 11F, G). While the basis for this is unclear, they underscore that donor Perforin and Ifnγ deficiency distinctly impact neuropathology in hiT cell-bearing nude mice.

Example 6. Severe Cognitive Impairment

Figure 11H:
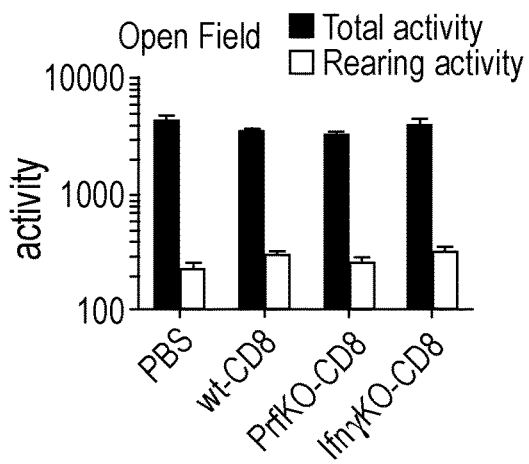
Figure 11I:
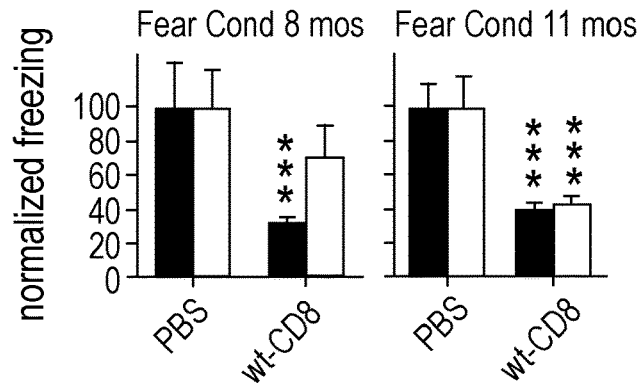
Figure 12A:
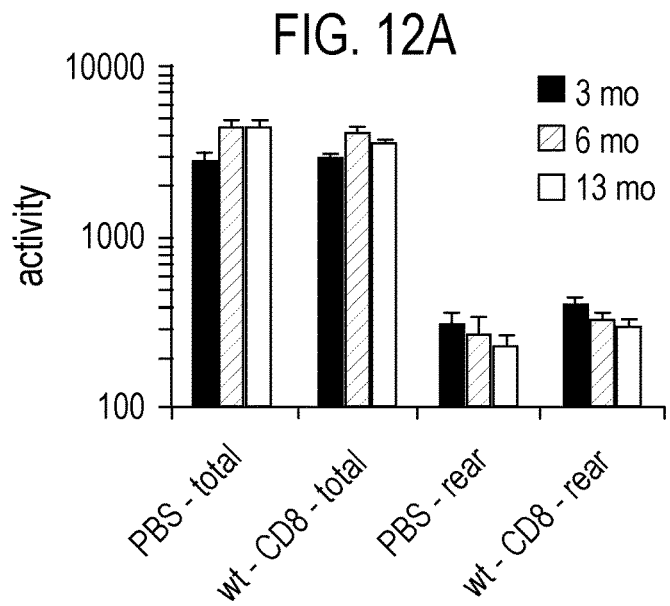
Figure 12B:
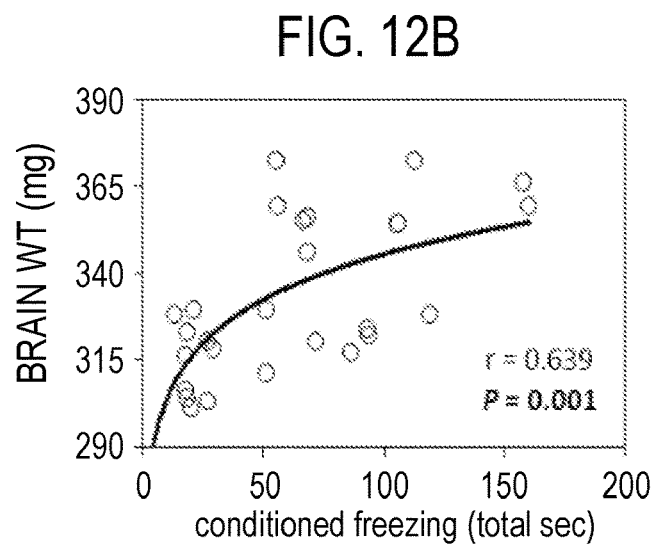

Overall motor and rearing activity in Open Field testing was not significantly different between treatment and control groups of nude recipients 3, 6, or 13 months after T cell injection (FIG. 11H; FIG. 12A). In contrast, Fear Conditioning performance for contextual learning was specifically reduced in wt-CD8 relative to PBS group 6 months after T cell injection, while both contextual and cued learning was impaired at 11 months (FIG. 11I). These results suggest that the cognitive impairment in wt-CD8 group is functionally localized to hippocampus early (required for contextual learning), but progresses to impair amygdala function later (required for cued learning). A similar pattern of impaired cognition occurs in human AD (23). Contextual learning performance at 6 months was also strongly correlated with brain mass (FIG. 12B). Thus, progressive cognitive impairment was initiated concomitant with soluble Aβ and pTau/PHF accumulation.

Figure 11J:
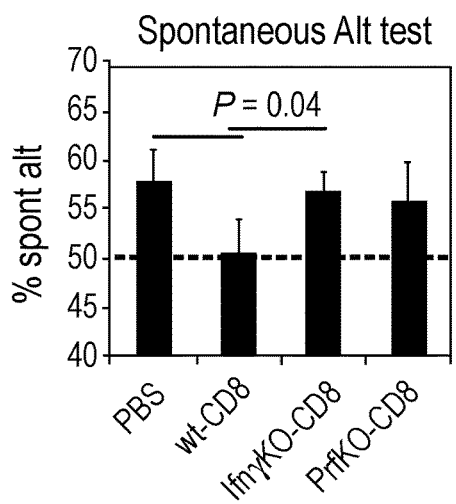
Figure 11K:
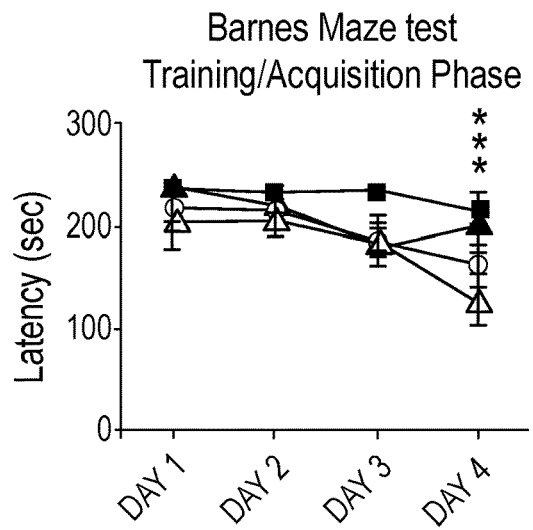
Figure 11L:
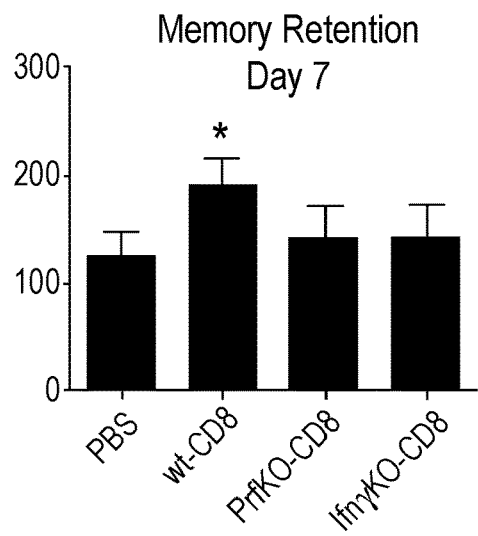
Figure 11M:
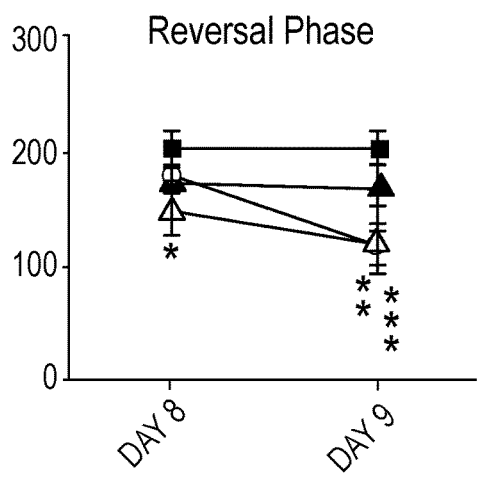
Figure 11N:
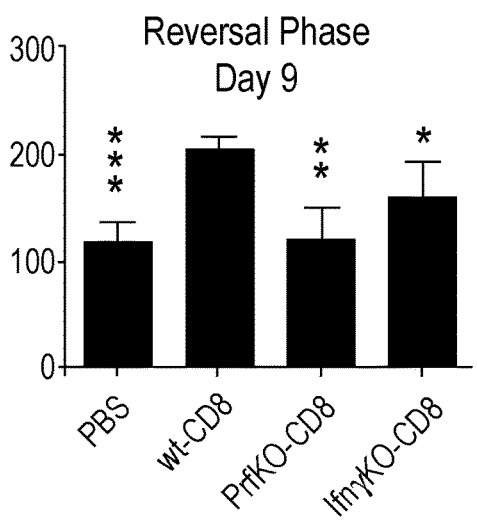
Figure 12C:
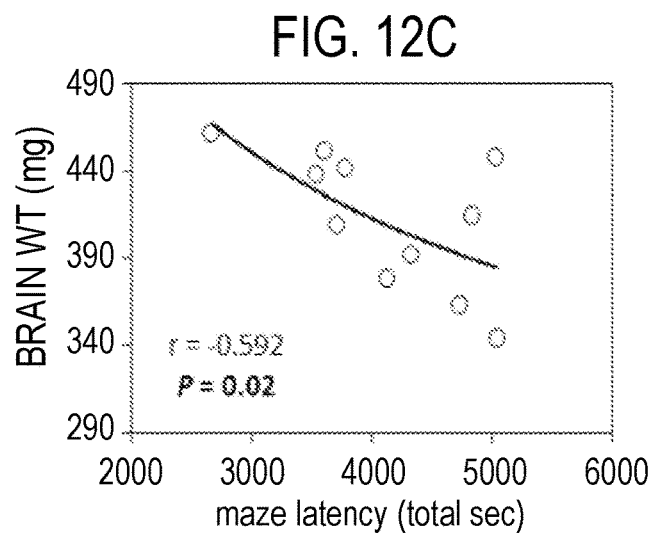

Spontaneous Alternation (SA) was measured 12 months post-injection to independently confirm cognitive deficits. This test is based on the predilection of mice to alternately explore two alleys, provided they recall the alley they previously entered. The lowest possible score is 50% indicating random alley choice, which suggests essentially no short-term memory. Most groups' SA scores were comparable to published values for wild-type mice at 55-56% (24), except for the wt-CD8 group's at 50% (FIG. 11J). To rule out the possibility of aversion to novelty, we further conducted the Barnes Maze test at 14 months, a more definitive measure of hippocampus-dependent learning and memory. Wt-CD8 group nude recipients showed no improvement in learning the maze over the initial 4-day training period, whereas all other groups did (FIG. 11K). Given this initial deficit, wt-CD8 mice were expectedly impaired on the memory retention and reversal learning phases of the maze as well (FIG. 11L-11N). As with Fear-Conditioning, there was a significant correlation between brain mass and performance in the Barnes Maze (FIG. 12C). Thus, by three distinct behavioral tests, wt-CD8 group nude mice exhibited progressive, severe and lasting impairment of learning and memory without overt motor deficits.

Figure 12D:
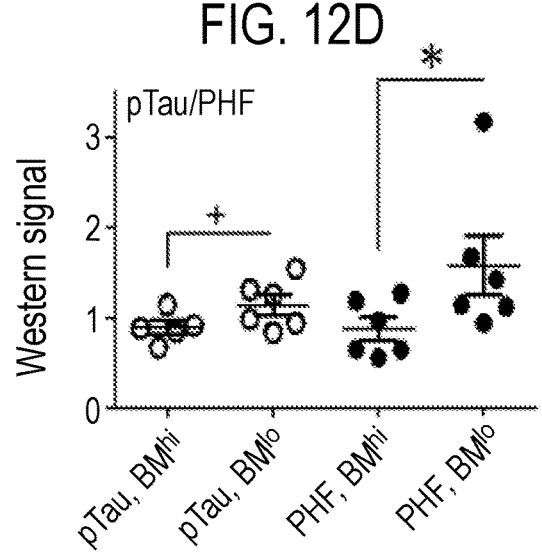
Figure 12E:
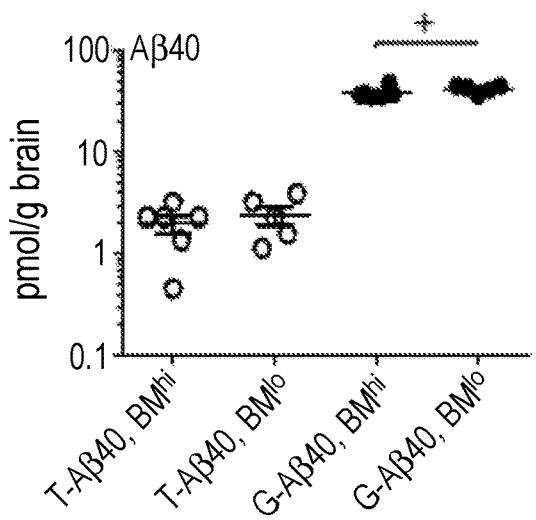
Figure 12F:
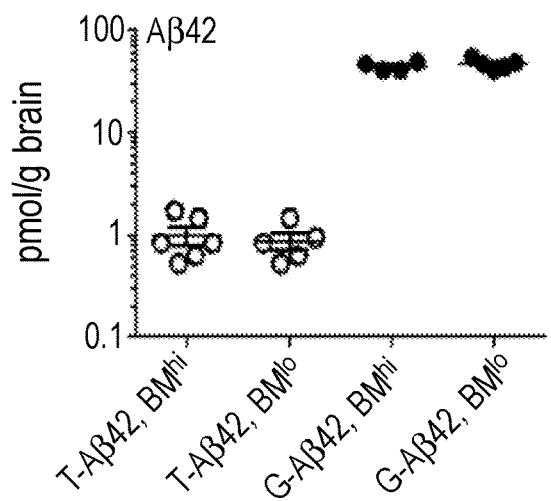

Cognitive impairments in the wt-CD8 group nude mice were associated with brain loss, further suggesting behavioral and structural parallels to human AD. Expanding on this, we addressed whether cognitive performance in the Barnes Maze was associated elevated tau and/or Aβ metrics. Poor performance on Barnes Maze (total latency time lower than median=$BM^{lo}$) exhibited a non-significant association with increased soluble pTau, and a significant association with increased tau PHFs on Westerns (FIG. 12D). By contrast, poor maze performance was not significantly associated with either Triton-soluble or Guanidium-soluble Aβ40 and Aβ42 by ELISA, although a non-significant and slight association emerged for increased Guanidium-soluble Aβ40 (FIG. 12E, 12F). Thus, cognitive impairment in wt-CD8 group nude mice was exclusively associated with elevated fibrillar tau deposition, as has been reported in human AD(25).

Example 7. hiT Cells in Wild-Type Mice Synergize with TBI

We next sought to determine if hiT cells initiated neuropathological effects in wild-type, with or without additional risk factors. We subjected cohorts of wild-type (B6) mice to sham- or single-impact brain injury, one day before injecting them with PBS or pre-expanded hiT cells (FIG. 13A). We then examined Aβ by ELISA, and pTau/PHF and NeuN signals by Westerns, as biomarkers of AD-like proteinopathy and neurodegeneration over a 10-week time frame. As expected, control CD8 T cell injection into B6.Foxn1 hosts significantly increased Triton-soluble Aβ40 and pTau/PHF in brain (FIG. 13B, C). NeuN signal, however, was not yet decreased in nude controls at 10 weeks (FIG. 13D). By contrast, hiT cells transferred into B6 hosts did not alter Aβ40 or pTau, but significantly reduced NeuN signal (FIG. 13A-13D). Thus, the nude strain background promoted early AD-like proteinopathy mediated by hiT cells, yet appeared to inhibit their anti-neuronal properties.

Single-impact traumatic brain injury (TBI) alone reduced Aβ and increased PHF in wild-type mice 10 weeks later, mirroring published studies (26, 27). Adding hiT cells, however, substantially enhanced Aβ40, pTau, and PHF accumulation following TBI. Thus, hiT cells induced human-like amyloidopathy following TBI in mice. TBI also induced measurable expansion of donor KLRG1$^+$ hiT cells in blood (FIG. 13E), which may be related to its synergy with hiT cells. This validates the notion that, in addition to initiating similar neurodegeneration in nude and wild-type mice, hiT cells synergize with a known risk factor to enhance AD-like neuropathology. This also establishes useful short-term metrics in wild-type mice that may facilitate analysis of host-specific factors modulating the effects of hiT cells, as well as aid in drug screening efforts.

Example 8. hiT Cell Phenotype & Effector Protein in Human AD Brain

Figure 14A:
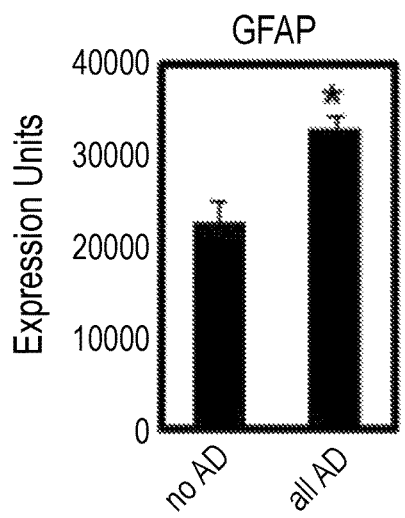
Figure 14B:
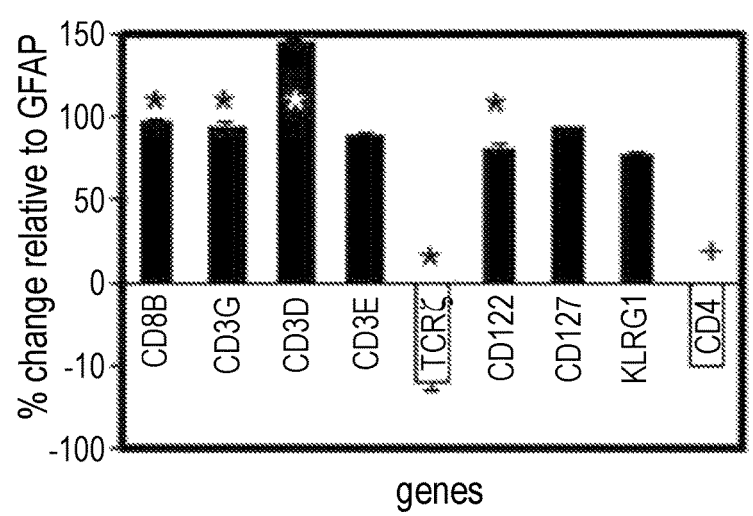

To examine if altered hiT cell-associated metrics were detectable in human LOAD, we first focused on hiT cell-associated gene expression. To establish a benchmark for increased cellular content, we initially quantified the increase in GFAP gene expression in AD brain, an established hallmark of astrogliosis in AD (FIG. 14A). We then normalized hiT cell marker gene expression relative to this benchmark (FIG. 14B). Interestingly, T cell genes (CD3, CD8, and TCR) as well as signature hiT cell markers (CD122, CD127, and KLRG1), were up-regulated to the same extent as GFAP, in AD relative to normal-aging controls (+100%=47% increased gene expression in AD relative to normal aging controls, as with GFAP). Probesets for T cell effector genes, IFNG, PRF1, and CD107, were also upregulated in severe AD (FIG. 14 legend). In contrast, probesets for CD4 and TCRζ, as well as those for housekeeping genes, tended to be down-regulated in severe AD (FIG. 14 legend). This parallels down-regulation of TCRζ under pro-inflammatory conditions (28), and indicates specific upregulation of hiT cell genes in AD brain.

Figure 14C:
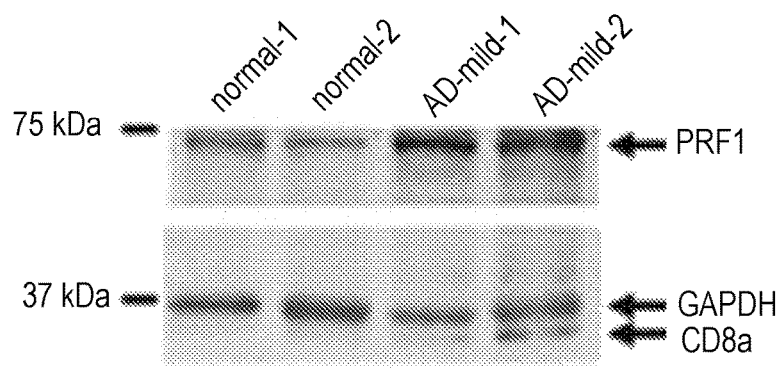
Figure 14C:
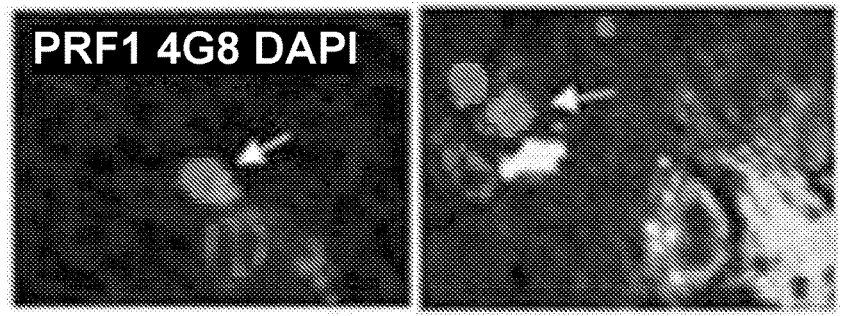
Figure 14D:
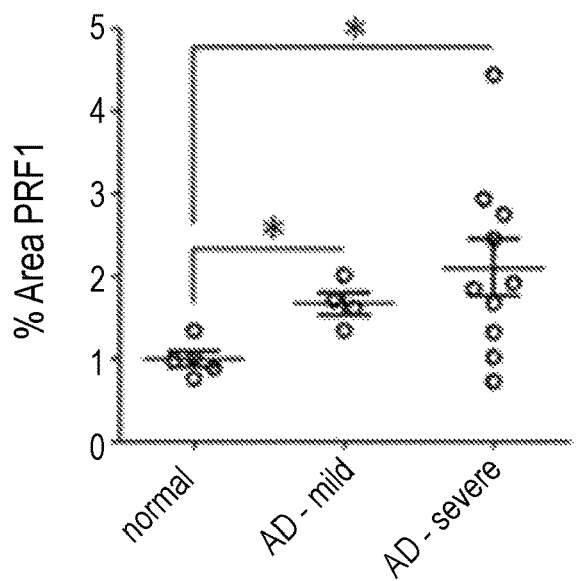
Figure 14E:
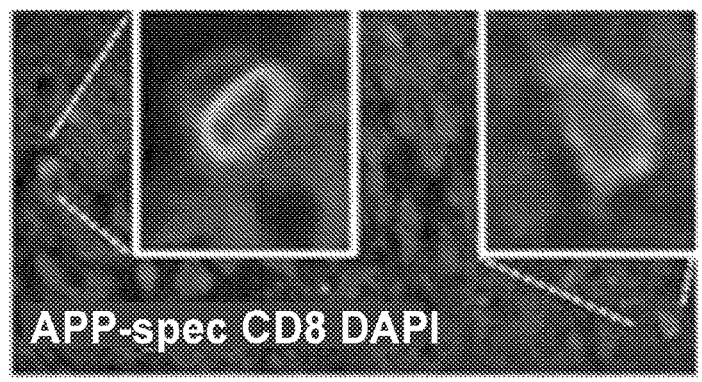
Figure 14F:
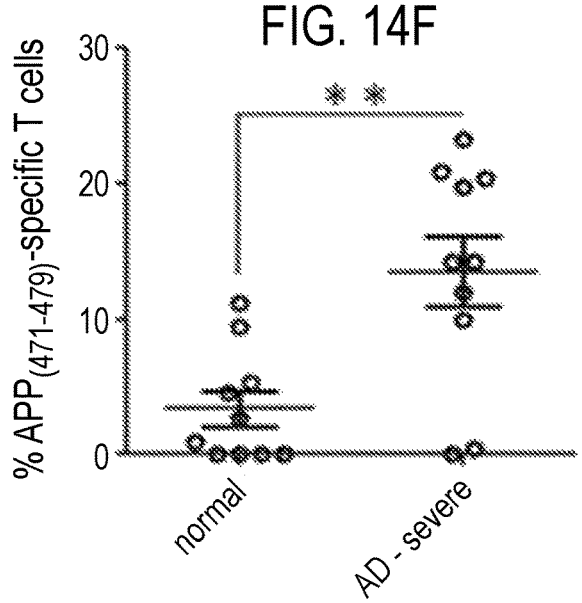

We further tested if a key hiT cell effector protein is elevated in human AD brain. Since IFNγ is not specific for lytic lymphocytes, and is already known to be associated with AD risk (3, 29), we focused on Perforin1, a protein restricted to natural killer and memory CD8 T cells. Western analysis of brain homogenates rendered the expected antibody specificity (68-75 kDa species), and stained lymphocytic nuclei in brain tissue with the expected punctate pattern, in addition to larger vesicles (FIG. 14C). Perforin and CD8 signals were correlated on Westerns (n=6; r=0.8155, P=0.048), and Perforin levels were significantly increased in combined cortex and hippocampus from patients with mild or severe AD pathology (FIG. 14D). Thus, a hiT cell effector protein critical for AD-like neurodegeneration in mice was also elevated in AD brain.

Finally, we next generated human pHLA-A2 multimers to a human APP epitope analogous to that recognized by hiT cells in mice [APP$_{(471-479)}$]. We co-stained hippocampus from human AD and normal aging patients with these multimers plus anti-CD8, to quantify epitope-reactive CD8 T cells. Overall CD8 T cell levels in AD brain were not significantly higher than in controls (n=10; 1.6±0.29 vs. 2.3±0.55, P=0.31), but CD8 T cells reactive to APP$_{(471-479)}$ were significantly elevated in AD (FIG. 6E, F; P=0.002). Thus, CD8 T cells that recognize a particular epitope on APP are elevated in human AD brain, as they are in hiT cell-bearing mice.

Nude mice harboring hiT cells exhibited several similarities with human neurodegenerative disorders, and with AD in particular. Specifically, early Aβ and later plaque accumulation was evident in them. So was neuroinflammation, silver-stained neurons, synaptic and neuronal loss with related brain atrophy, and profound cognitive impairment. Of these features, several are not typically seen in mouse models based on familial AD (FAD) mutations, notably neuronal loss, silver-stained cells, and brain atrophy related to neurodegeneration. There were, however, distinctions between AD or FAD-based mouse model neuropathology, and that of nude mice harboring hiT cells: Aβ40 alone was increased without apparent involvement of Aβ42, and plaques were predominantly diffuse rather than hard-core. Nude mice also did not exhibit the acellular "ghost tangles" typically seen in human AD.

Although rare familial forms of AD exhibit a pattern of mainly Aβ40 elevation (30, 31), we suspect that its predominance without Aβ42 involvement in nude mice harboring hiT cells is more likely due to a combination of factors. First, Aβ42 is less stable and more difficult to accurately quantify than Aβ40, although we believe the following additional factors more likely conspire to obscure Aβ42 involvement in our studies: the inclusion of vascular amyloid, which is comprised mainly of Aβ40 in ELISA analysis (32); the reduced efflux rate of mouse Aβ40 over Aβ42, which is opposite to that of the human species (33); and factors that specifically inhibit Aβ42 fibrillar assembly in rodent brain (34). Ghost tangles, on the other hand, are remains of dead neuronal material, and unlike other neurofibrillary structures are comprised mainly of 3R tau (35, 36). Their absence in nude mice harboring hiT cells is thus easily explained by the near absence of 3R tau in adult mice. Hence, a combination of technical and mouse-specific factors likely account for apparent discrepancies between nude mouse and human AD proteinopathy. It is nevertheless clear that hiT cell functions mediate an AD-like neurodegenerative syndrome in nude recipients.

Both lytic and proinflammatory T cell effector functions were required for neurodegeneration in nude mice harboring hiT cells, but they affected neuropathological features differently. Perforin1 was required for CD8 T cells to accumulate in brain and mediate any and all neuropathological features. Although critical for this earliest of events, the involvement of Perforin1 in controlling CD8 T cell interaction with brain could also help explain why cell death pathways are associated with AD (37), as Perforin initiates caspase-mediated apoptosis in target cells. Indeed, sizes of the early APP cleavage products observed in nude mice were most consistent with combined caspase-secretase cleavage (FIG. 5A).

In contrast to Perforin1, Ifnγ in hiT cells was required to selectively promote neuroinflammation, although it also appeared to moderately delay brain proteinopathy. Indeed, the restricted distribution of amyloid and neurofibrillary structures in the IfnγKO-CD8 group is reminiscent of an early preclinical stage of AD (38), and corroborates previous reports that IFNγ accelerates AD pathology (39). The impaired astrogliosis and microgliosis in this group is also consistent with previous findings that IFNγ activates neuroinflammation in FAD mutation-based mouse models (4). The unexpected increase in NeuN, Drebrin, and brain mass in IfnγKO-CD8 group mice, however, suggests that IFNγ may also regulate neurodegeneration independent of neuroinflammation, possibly by suppressing neurogenesis and/or synaptogenesis. Given their distinct effects, it will be interesting to determine if Perforin1$^+$ or IFNγ$^+$CD8 T cells represent biomarkers for initiation and progression, respectively, in human neurodegenerative conditions. Further dissection of the mechanisms through which Perforin1 and Ifnγ promote neuropathology in hiT-bearing mice may also unmask novel functions of these two effectors.

Certain aspects of pathophysiology in mice harboring hiT cells were affected by general T cell-deficiency. For example, hiT cells alone induced significant Aβ and pTau/PHF increases after 10 weeks in nude, but not in wild-type, recipients. Conversely, hiT cells did not decrease neuronal metrics after 10 weeks in nude mice, but they did so in wild-type recipients. This suggests that AD-like proteinopathy induced by hiT cells is enhanced by the modification of other cells in the nude environment, whereas neurodegeneration mediated by hiT cells is inhibited by such modification. This may be related to the inhibitory effects of CD4 T cells and/or monocytes on amyloid accumulation and cognitive impairment (40) (41), as both cell populations are significantly altered in nude mice. Nevertheless, at least some strain effects were overridden by the addition of TBI, as Aβ and especially pTau/PHF were elevated in hiT cell-bearing wild-type mice subjected to brain injury. Thus, although multiple immune factors may influence the degree or timing of neuropathology and neurodegeneration in hiT-bearing mice, some may be nullified by strong risk factors.

The existence of HLA-DR risk alleles in Parkinson's as well as AD suggest that T cells may be generally involved in neurodegenerative etiology (42, 43). Moreover, the surprising recent discovery of lymphatic vasculature in brain demonstrates a potential structural basis for general T cell involvement in brain pathophysiology (44). Some, but not all studies have reported increased CD8 T cells (9, 10, 45-48), or more general autoimmune features in AD (49), but the nature of T cell involvement has been unclear and relatively understudied. Given reactivity of hiT cells to self-antigens in the current study, as well as the involvement of Perforin1, it is reasonable to speculate that lytic self-reactivity may contribute to hiT cell-induced neuropathology. Nevertheless, hiT-mediated pathology differed markedly from the classical autoimmune neurodegeneration seen in human multiple sclerosis (MS) or mouse experimental autoimmune encephalomyelitis (EAE) in several ways. First, it was dependent on CD8 rather than CD4 T cells. It was also improved rather than impaired by IFNγ deficiency, and did not involve robust immune infiltrates. Further, hiT-bearing mice completely lacked the motor deficits that define MS and EAE. Finally, hiT-bearing mouse pathology was accompanied by plaque and neurofibrillary deposits, and a pattern of hippocampus- to amygdala-dependent cognitive deficits, each of which are more typical of AD than MS (23). Taken together, this strongly suggests that hiT cells do not mediate MS-like autoimmune neurodegeneration, but rather critically contribute to AD-like neurodegeneration.

Our findings also constitute the first evidence that aberrant CD8 T cells promote tissue degeneration in an age-related pathological condition. Because this degeneration appeared related to reactivity to an epitope on APP, it is conceivable that hiT cells reactive to distinct tissue antigens may damage other areas of the brain or body. The hiT model and age-related CD8 T cell dysfunction in general may thus be relevant to other age-related disorders, and perhaps to the widespread tissue degeneration observed during healthy aging.

Example 9. ELISPOT Assay Protocol for PBMC Immune Response

Material: Human IFN-γ ELISPOT Kit (BD Biosciences, cat #: 552138); 6-Well-Plate (non-tissue culture treated plate, BD Falcon, 351146); RPMI1640 (Life Technologies, gibco, 21870-076); FBS (Omega, Cat #: FB-02); IL-2: BD Biosciences, Cat #356043 reconstituted to working stock $4×10^4$ IU/ml (1000×) stored at −20° C.; IL-7: R & D Systems, Cat #207-IL-025 reconstituted to working stock $2×10^4$ ng/ml (1000×) stored at −20° C.; PBMC: AD and normal control patients' PBMCs from blood draws, frozen in liquid nitrogen; each vial contains $1-2×10^7$ cells; Antigenic peptide: synthetic, APP-derived epitopes.

Reagent Preparation: (1) Detection Antibody Solution: According to instructions on the Certificate of Analysis or lot specific data sheet, add required quantity of Detection Antibody to Assay Diluent (1:250 dilute), vortex or mix. For best performance, prepare Detection Antibody Solution immediately prior to use. (2) Strepavidin-HRP (SAv-HRP) Solution: According to instructions on the Certificate of Analysis, add required quantity of SAv-HRP to Assay Diluent (1:100), vortex or mix. For best performance, prepare SAv-HRP Solution immediately prior to use. (3) Wash Buffer: Dilute require quantity of 20× Wash Concentrate immediately with deionized water, mix. (4) PBS; Dilute required quantity of 10×PBS with deionized water, mix. (5) AEC Substrate Solution: No more than 15 minutes prior to use, mix 20 ul of AEC Chromogen with each 1 ml of AEC Substrate Buffer, vortex or mix. Discard any remaining prepared AEC Substrate Solution after use. (6) R10 medium: Make fresh RPMI1640+10% FBS medium prior to use. (7) Stimulating medium: R10 with IL-2 (40 IU/ml final concentration), IL-7 (20 ng/ml final concentration) and Gentamicin (Gibco Cat: 15710-072).

Cell Treatment: Day 1—All steps need to be sterile. Thaw the frozen PBMCs at 37° C. water bath, each sample vial contains 1-2×10*7 PBMCs. Transfer cells to 15 ml centrifuge tubes, add warm fresh R10 medium to total volume 5 ml and mix. Then centrifuge cells at 1300 rpm for 3 minutes. Re-suspend cells with 6 ml warm R10, mix well and incubate at 37° C. in a 5% $CO_2$ incubator for 20 minutes. Keep the tube caps loose. Centrifuge cells at 1300 rpm for 3 minutes, discard the supernatant. Re-suspend the cells with 6 ml stimulating medium. Mix well. Transfer 3 ml cells to two 6-well-plate wells, respectively. Add 0.3 mg antigenic peptide(s) to one well (stimulating well) at final concentration of 100 μg/ml. The other well remains no peptide added as negative comparison. Replace the plate lid and incubate at 37° C. in a 5% $CO_2$ incubator for 6 days.

Cell Treatment: Day 6—All steps need to be sterile. Transfer cells into 15 ml centrifuge tubes. Wash the plate once with PBS. Centrifuge cells at 1300 rpm for 3 minutes, discard the supernatant. Re-suspend cells with 1 ml R10 medium. Count cell number. Spin down cells at 1300 rpm for 3 minutes, discard the supernatant. According to the cell number, add appropriate volume of stimulating medium to corresponding tube and re-suspend the cells at concentration of $2\times10*6$ cells/ml. Prepare cell suspensions at 3 different densities ($2\times10*6$/ml, $1\times10*6$/ml and $4\times10*5$/ml). Add 100 μl/well stimulating medium to BD™ Elispot plate. Add 100 μl/well cell suspensions to the Elispot plate, so the final cell concentration gradients are $1\times10*6$/ml, $5\times10*5$/ml and $2\times10*5$. Add patient's autologous antigenic peptide to stimulating samples at final concentration of 100 μg/ml. No peptide will be added to negative comparison sample. Add 200 μl/well stimulating medium to Elispot microwells as negative control. Add 200 μl/well stimulating medium to Elispot microwells, then add PHA as Positive control (PHA final concentration 5 μg/ml). Replace the plate lid and incubate at 37° C. in a 5% $CO_2$ incubator overnight.

Day 7—Detection Antibody: Aspirate cell suspension. Wash wells 2× with 200 ul/ml deionized(DI) water. Allow wells to soak for 3-5 minutes at each wash step. Wash wells 3× with 200 ul/well prepared Wash Buffer (see Reagent Preparation, step 3). Discard Wash Buffer. Add prepared Detection Antibody Solution at 100 ul per well (see Reagent Preparation above). Replace lid and incubate for 2 hours at room temperature.

Enzyme—Discard Detection Antibody solution. Wash wells 3× with 200 μl/well prepared. Wash Buffer. Allow wells to soak 1-2 minutes at each wash step. Add prepared Streptavidin-HRP Solution at 100 μl/well (see Reagent Preparation above). Replace lid and incubate for 1 hours at room temperature.

Substrate—Discard Streptavidin-HRP solution. Wash wells 4× with 200 μl/well prepared Wash Buffer. Allow wells to soak 1-2 minutes at each wash step. Wash wells 2× with 200 ul/well prepared PBS (see Reagent Preparation above). Add 100 μl of prepared AEC Substrate Solution to each well (see Reagent Preparation above). Monitor spot development from 5-20 minutes. Do not let color overdevelop as this will lead to high background. Stop substrate reaction by washing wells with DI water. Air-dry plate at room temperature for 2 hours to overnight until it is completely dry. Removal of plastic tray supporting the 96-well plate will facilitate drying. Store plate in a sealed plastic bag, in the dark, until it is analyzed. The plate can be stored un-analyzed as long as 3 months.

Analysis—To enumerate spots, the plate will be mailed out to a third party facility and inspected automatically using an Elispot plate reader.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

REFERENCES

1. Duyckaerts, C, Potier, M C, and Delatour, B. 2008. Alzheimer disease models and human neuropathology: similarities and differences. Acta Neuropathol 115:5-38.
2. Paris, D, Humphrey, J, Quadros, A, Patel, N, Crescentini, R, Crawford, F, and Mullan, M. 2003. Vasoactive effects of A beta in isolated human cerebrovessels and in a transgenic mouse model of Alzheimer's disease: role of inflammation. Neurol Res 25:642-651.
3. Blasko, I, Marx, F, Steiner, E, Hartmann, T, and Grubeck-Loebenstein, B. 1999. TNFalpha plus IFNgamma induce the production of Alzheimer beta-amyloid peptides and decrease the secretion of APPs. FASEB J 13:63-68.
4. Browne, T C, McQuillan, K, McManus, R M, O'Reilly, J A, Mills, K H, and Lynch, M A. 2013. IFN-gamma Production by amyloid beta-specific Th1 cells promotes microglial activation and increases plaque burden in a mouse model of Alzheimer's disease. J Immunol 190: 2241-2251.
5. Talbot, K, and Wang, H Y. 2014. The nature, significance, and glucagon-like peptide-1 analog treatment of brain insulin resistance in Alzheimer's disease. Alzheimers Dement 10:S12-25.
6. Clambey, E T, van Dyk, L F, Kappler, J W, and Marrack, P. 2005. Non-malignant clonal expansions of CD8+ memory T cells in aged individuals. Immunol Rev 205: 170-189.
7. den Braber, I, Mugwagwa, T, Vrisekoop, N, Westera, L, Mogling, R, de Boer, A B, Willems, N, Schrijver, E H, Spierenburg, G, Gaiser, K, et al. 2012. Maintenance of peripheral naive T cells is sustained by thymus output in mice but not humans. Immunity 36:288-297.
8. Qi, Q, Zhang, D W, Weyand, C M, and Goronzy Jö, J. 2014. Mechanisms shaping the naïve T cell repertoire in the elderly—Thymic involution or peripheral homeostatic proliferation? Exp Gerontol 54:71-74.
9. Lueg, G, Gross, C C, Lohmann, H, Johnen, A, Kemmling, A, Deppe, M, Groger, J, Minnerup, J, Wiendl, H, Meuth, S G, et al. 2014. Clinical relevance of specific T-cell activation in the blood and cerebrospinal fluid of patients with mild Alzheimer's disease. Neurobiol Aging.
10. Togo, T, Akiyama, H, Iseki, E, Kondo, H, Ikeda, K, Kato, M, Oda, T, Tsuchiya, K, and Kosaka, K. 2002. Occurrence of T cells in the brain of Alzheimer's disease and other neurological diseases. J Neuroimmunol 124:83-92.
11. Zotova, E, Bharambe, V, Cheaveau, M, Morgan, W, Holmes, C, Harris, S, Neal, J W, Love, S, Nicoll, J A, and Boche, D. 2013. Inflammatory components in human Alzheimer's disease and after active amyloid-beta42 immunization. Brain 136:2677-2696.
12. Schindowski, K, Eckert, A, Peters, J, Gorriz, C, Schramm, U, Weinandi, T, Maurer, K, Frö"lich, L, and Mu"ller, W E. 2007. Increased T-cell Reactivity and Elevated Levels of CD8+ Memory T-cells in Alzheimer's Disease-patients and T-cell Hyporeactivity in an Alzheimer's Disease-mouse Model: Implications for Immunotherapy. Neuromol Med 9:340-354.
13. Jouanneau, E, Black, K L, Veiga, L, Cordner, R, Goverdhana, S, Zhai, Y, Zhang, X, Panwar, A, Mardiros, A, Wang, H Q, et al. 2014. Intrinsically de-sialyated CD103+ CD8 T cells mediate beneficial anti-glioma immune responses. Cancer Immunol Immunother 63:911-924.
14. Prins, R M, Graf, M R, Merchant, R E, Black, K L, and Wheeler, C J. 2003. Deficits in thymic function and output of recent thymic emigrant T cells during intracranial glioma progression. J Neurooncol 64:45-54.
15. Nishimura, S, Manabe, I, Nagasaki, M, Eto, K, Yamashita, H, Ohsugi, M, Otsu, M, Hara, K, Ueki, K, Sugiura, S, et al. 2009. CD8+ effector T cells contribute to macrophage recruitment and adipose tissue inflammation in obesity. Nat Med 15:914-920.
16. Trott, D W, Thabet, S R, Kirabo, A, Saleh, M A, Itani, H, Norlander, A E, Wu, J, Goldstein, A, Arendshorst, W J, Madhur, M S, et al. 2014. Oligoclonal CD8+ T cells play a critical role in the development of hypertension. Hypertension 64:1108-1115.
17. Zanni, F, Vescovini, R, Biasini, C, Fagnoni, F, Zanlari, L, Telera, A, Di Pede, P, Passeri, G, Pedrazzoni, M, Passeri, M, et al. 2003. Marked increase with age of type 1 cytokines within memory and effector/cytotoxic CD8+ T cells in humans: a contribution to understand the relationship between inflammation and immunosenescence. Exp Gerontol 38:981-987.
18. LeMaoult, J, Messaoudi, I, Manavalan, J S, Potvin, H, Nikolich-Zugich, D, Dyall, R, Szabo, P, Weksler, M E, and Nikolich-Zugich, J. 2000. Age-related dysregulation in CD8 T cell homeostasis: kinetics of a diversity loss. J Immunol 165:2367-2373.
19. Messaoudi, I, Lemaoult, J, Guevara-Patino, J A, Metzner, B M, and Nikolich-Zugich, J. 2004. Age-related CD8 T cell clonal expansions constrict CD8 T cell repertoire and have the potential to impair immune defense. J Exp Med 200:1347-1358.
20. Messaoudi, I, Warner, J, and Nikolich-Zugich, J. 2006. Age-related CD8+ T cell clonal expansions express elevated levels of CD122 and CD127 and display defects in perceiving homeostatic signals. J Immunol 177.
21. Badovinac, V P, Tvinnereim, A R, and Harty, J T. 2000. Regulation of antigen-specific CD8+ T cell homeostasis by perforin and interferon-gamma. Science 290:1354-1358.

22. Cohen, R M, Rezai-Zadeh, K, Weitz, T M, Rentsendorj, A, Gate, D, Spivak, I, Bholat, Y, Vasilevko, V, Glabe, C G, Breunig, J J, et al. 2013. A transgenic Alzheimer rat with plaques, tau pathology, behavioral impairment, oligomeric abeta, and frank neuronal loss. J Neurosci 33:6245-6256.
23. Serrano-Pozo, A, Frosch, M P, Masliah, E, and Hyman, B T. 2011. Neuropathological alterations in Alzheimer disease. Cold Spring Harb Perspect Med 1:a006189.
24. Ma, Q L, Yang, F, Rosario, E R, Ubeda, O J, Beech, W, Gant, D J, Chen, P P, Hudspeth, B, Chen, C, Zhao, Y, et al. 2009 Beta-amyloid oligomers induce phosphorylation of tau and inactivation of insulin receptor substrate via c-Jun N-terminal kinase signaling: suppression by omega-3 fatty acids and curcumin. J Neurosci 29:9078-9089.
25. Brier, M R, Gordon, B, Friedrichsen, K, McCarthy, J, Stern, A, Christensen, J, Owen, C, Aldea, P, Su, Y, Hassenstab, J, et al. 2016. Tau and Abeta imaging, CSF measures, and cognition in Alzheimer's disease. Sci Transl Med 8:338ra366.
26. Nakagawa, Y, Nakamura, M, McIntosh, T K, Rodriguez, A, Berlin, J A, Smith, D H, Saatman, K E, Raghupathi, R, Clemens, J, Saido, T C, et al. 1999. Traumatic brain injury in young, amyloid-beta peptide overexpressing transgenic mice induces marked ipsilateral hippocampal atrophy and diminished Abeta deposition during aging. J Comp Neurol 411:390-398.
27. Nakagawa, Y, Reed, L, Nakamura, M, McIntosh, T K, Smith, D H, Saatman, K E, Raghupathi, R, Clemens, J, Saido, T C, Lee, V M, et al. 2000. Brain trauma in aged transgenic mice induces regression of established abeta deposits. Exp Neurol 163:244-252.
28. Zhang, Z, Gorman, C L, Vermi, A C, Monaco, C, Foey, A, Owen, S, Amjadi, P, Vallance, A, McClinton, C, Marelli-Berg, F, et al. 2007. TCRzetadim lymphocytes define populations of circulating effector cells that migrate to inflamed tissues. Blood 109:4328-4335.
29. Blasko, I, Veerhuis, R, Stampfer-Kountchev, M, Saurwein-Teissl, M, Eikelenboom, P, and Grubeck-Loebenstein, B. 2000. Costimulatory effects of interferon-gamma and interleukin-lbeta or tumor necrosis factor alpha on the synthesis of Abeta1-40 and Abeta1-42 by human astrocytes. Neurobiol Dis 7:682-689.
30. Grabowski, T J, Cho, H S, Vonsattel, J P, Rebeck, G W, and Greenberg, S M. 2001. Novel amyloid precursor protein mutation in an Iowa family with dementia and severe cerebral amyloid angiopathy. Ann Neurol 49:697-705.
31. Hellstrom-Lindahl, E, Viitanen, M, and Marutle, A. 2009. Comparison of Abeta levels in the brain of familial and sporadic Alzheimer's disease. Neurochem Int 55:243-252.
32. Mann, D M, Iwatsubo, T, Ihara, Y, Cairns, N J, Lantos, P L, Bogdanovic, N, Lannfelt, L, Winblad, B, Maat-Schieman, M L, and Rossor, M N. 1996. Predominant deposition of amyloid-beta 42(43) in plaques in cases of Alzheimer's disease and hereditary cerebral hemorrhage associated with mutations in the amyloid precursor protein gene. Am J Pathol 148:1257-1266.
33. Banks, W A, Robinson, S M, Verma, S, and Morley, J E. 2003. Efflux of human and mouse amyloid beta proteins 1-40 and 1-42 from brain: impairment in a mouse model of Alzheimer's disease. Neuroscience 121:487-492.
34. Shin, R W, Ogino, K, Kondo, A, Saido, T C, Trojanowski, J Q, Kitamoto, T, and Tateishi, J. 1997. Amyloid beta-protein (Abeta) 1-40 but not Abeta1-42 contributes to the experimental formation of Alzheimer disease amyloid fibrils in rat brain. J Neurosci 17:8187-8193.
35. Lace, G, Savva, G M, Forster, G, de Silva, R, Brayne, C, Matthews, F E, Barclay, J J, Dakin, L, Ince, P G, and Wharton, S B. 2009. Hippocampal tau pathology is related to neuroanatomical connections: an ageing population-based study. Brain 132:1324-1334.
36. Uchihara, T, Hara, M, Nakamura, A, and Hirokawa, K. 2012. Tangle evolution linked to differential 3- and 4-repeat tau isoform deposition: a double immunofluorolabeling study using two monoclonal antibodies. Histochem Cell Biol 137:261-267.
37. de Calignon, A, Fox, L M, Pitstick, R, Carlson, G A, Bacskai, B J, Spires-Jones, T L, and Hyman, B T. 2010. Caspase activation precedes and leads to tangles. Nature 464:1201-1204.
38. Liang, K Y, Mintun, M A, Fagan, A M, Goate, A M, Bugg, J M, Holtzman, D M, Morris, J C, and Head, D. 2010. Exercise and Alzheimer's disease biomarkers in cognitively normal older adults. Ann Neurol 68:311-318.
39. Cho, H J, Kim, S K, Jin, S M, Hwang, E M, Kim, Y S, Huh, K, and Mook-Jung, I. 2007. IFN-gamma-induced BACE1 expression is mediated by activation of JAK2 and ERK1/2 signaling pathways and direct binding of STAT1 to BACE1 promoter in astrocytes. Glia 55:253-262.
40. Ethell, D W, Shippy, D, Cao, C, Cracchiolo, J R, Runfeldt, M, Blake, B, and Arendash, G W. 2006. Abeta-specific T-cells reverse cognitive decline and synaptic loss in Alzheimer's mice. Neurobiol Dis 23:351-361.
41. Koronyo-Hamaoui, M, Ko, M K, Koronyo, Y, Azoulay, D, Seksenyan, A, Kunis, G, Pham, M, Bakhsheshian, J, Rogeri, P, Black, K L, et al. 2009. Attenuation of AD-like neuropathology by harnessing peripheral immune cells: local elevation of IL-10 and MMP-9. J Neurochem 111:1409-1424.
42. Lambert, J C, Ibrahim-Verbaas, C A, Harold, D, Naj, A C, Sims, R, Bellenguez, C, Jun, G, Destefano, A L, Bis, J C, Beecham, G W, et al. 2013. Meta-analysis of 74,046 individuals identifies 11 new susceptibility loci for Alzheimer's disease. Nat Genet 45:1452-1458.
43. Nalls, M A, Pankratz, N, Lill, C M, Do, C B, Hernandez, D G, Saad, M, DeStefano, A L, Kara, E, Bras, J, Sharma, M, et al. 2014. Large-scale meta-analysis of genome-wide association data identifies six new risk loci for Parkinson's disease. Nat Genet 46:989-993.
44. Louveau, A, Smirnov, I, Keyes, T J, Eccles, J D, Rouhani, S J, Peske, J D, Derecki, N C, Castle, D, Mandell, J W, Lee, K S, et al. 2015. Structural and functional features of central nervous system lymphatic vessels. Nature 523:337-341.
45. Baglio, F, Saresella, M, Preti, M G, Cabinio, M, Griffanti, L, Marventano, I, Piancone, F, Calabrese, E, Nemni, R, and Clerici, M. 2013. Neuroinflammation and brain functional disconnection in Alzheimer's disease. Front Aging Neurosci 5:81.
46. Larbi, A, Pawelec, G, Witkowski, J M, Schipper, H M, Derhovanessian, E, Goldeck, D, and Fulop, T. 2009. Dramatic shifts in circulating CD4 but not CD8 T cell subsets in mild Alzheimer's disease. J Alzheimers Dis 17:91-103.
47. Monsonego, A, Zota, V, Karni, A, Krieger, J I, Bar-Or, A, Bitan, G, Budson, A E, Sperling, R, Selkoe, D J, and Weiner, H L. 2003. Increased T cell reactivity to amyloid beta protein in older humans and patients with Alzheimer disease. J Clin Invest 112:415-422.
48. Pellicano, M, Larbi, A, Goldeck, D, Colonna-Romano, G, Buffa, S, Bulati, M, Rubino, G, Iemolo, F, Candore, G, Caruso, C, et al. 2012. Immune profiling of Alzheimer patients. J Neuroimmunol 242:52-59.

49. Dinkins, M B, Dasgupta, S, Wang, G, Zhu, G, He, Q, Kong, J N, and Bieberich, E. 2015. The 5xFAD Mouse Model of Alzheimer's Disease Exhibits an Age-Dependent Increase in Anti-Ceramide IgG and Exogenous Administration of Ceramide Further Increases Anti-Ceramide Titers and Amyloid Plaque Burden. J Alzheimers Dis.

50. Kuzushima, K, Hayashi, N, Kimura, H, Tsurumi, T. 2001. Efficient identification of HLA-A*2402-restricted cytomegalovirus-specific CD8(+) T-cell epitopes by a computer algorithm and an enzyme-linked immunospot assay. Blood 98:1872-81.

Embodiments in which an exclusive property or privilege is claimed are defined as follows:

1. A method for determining the likelihood of late onset Alzheimer's disease (LOAD) in a subject in need thereof, comprising:
   (i) obtaining a sample from the subject;
   (ii) assaying the sample to determine the level of amyloid precursor protein (APP) specific CD8+ T cells; and
   (iii) determining that the subject has an increased likelihood of LOAD if the level of the APP-specific CD8+ T cells is higher relative to a reference sample, and
   (iv) treating the subject with an immunomodulating agent when the subject has an increased likelihood of LOAD.

2. The method of claim 1, wherein assaying the sample comprises quantitating the number of APP-specific CD8+ T cells in the sample.

3. The method of claim 2, wherein the APP-specific CD8+ T cells in the sample are quantitated using MHC multimers specific to peptides of APP.

4. The method of claim 3, wherein the peptides of APP comprise the amino acid sequence ALENYITAL (SEQ ID NO: 2), KLVFFAEDV (SEQ ID NO: 3), LMVGGWIA (SEQ ID NO: 4), GLMVGGWI (SEQ ID NO: 5), or VIVITLVML (SEQ ID NO: 6).

5. The method of claim 3, wherein the APP peptide-specific MHC multimers are MHC dimers, MHC tetramers, MHC pentamers or MHC dextramers.

6. The method of claim 3, wherein the APP peptide-specific MHC multimers are labeled with a detection agent.

7. The method of claim 6, wherein the APP peptide-specific MHC multimers labeled with the detection agent are quantitated using FACS, MACS or ELISPOT assays.

8. The method of claim 1, wherein the subject exhibits risk factors associated with LOAD.

9. The method of claim 8, wherein the risk factors are one or more of mild cognitive impairment (MCI), traumatic brain injury, diabetes mellitus, and APOE_epsilon_4 allele expression.

10. The method of claim 1, wherein the subject does not exhibit risk factors associated with LOAD and is at least 50 years old.

11. The method of claim 1, wherein the sample is brain tissue,
   and wherein the level of the APP-specific CD8+ T cells is higher relative to the reference sample.

12. The method of claim 1, wherein the subject is human.

13. The method of claim 1, wherein the reference value is the mean or median level of APP-specific CD8+ T cells in a population of subjects that do not have LOAD.

14. The method of claim 1, wherein the reference sample is the mean or median level of APP-specific CD8+ T cells in multiple samples obtained from the subject at different time points.

15. The method of claim 1, wherein the immunomodulating agent is a steroid.

16. The method of claim 1, wherein the immunomodulating agent is an APP peptide-specific MHC multimer conjugated to a cytotoxic agent.

17. The method of claim 16, wherein the cytotoxic agent is a toxin, an antibody, a heavy metal, a radioisotope or a hapten.

18. The method of claim 1, wherein the reference sample is a value determined from the mean or median level of APP-specific CD8+ T cells in a population of subjects that do not have a non-AD neurodegenerative disease.

19. The method of claim 18, wherein the non-AD neurodegenerative disease is Parkinson's Disease, a systemic autoimmune disease, a cerebral autoimmune disease or Multiple Sclerosis.

* * * * *